(12) United States Patent
Zhong

(10) Patent No.: US 8,846,863 B2
(45) Date of Patent: Sep. 30, 2014

(54) HEAT STABLE PROTEIN INGREDIENTS

(75) Inventor: Qixin Zhong, Knoxville, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 602 days.

(21) Appl. No.: 13/098,694

(22) Filed: May 2, 2011

(65) Prior Publication Data

US 2011/0268680 A1 Nov. 3, 2011

Related U.S. Application Data

(60) Provisional application No. 61/329,931, filed on Apr. 30, 2010.

(51) Int. Cl.
*C07K 1/107* (2006.01)
*A23J 3/08* (2006.01)

(52) U.S. Cl.
USPC ............................. 530/345; 530/322; 514/5.6

(58) Field of Classification Search
USPC .................................... 530/345, 322; 514/5.6
See application file for complete search history.

(56) References Cited

U.S. PATENT DOCUMENTS

| | | | |
|---|---|---|---|
| 2006/0159805 | A1 | 7/2006 | Funda et al. |
| 2006/0165990 | A1 | 7/2006 | Curtis et al. |

FOREIGN PATENT DOCUMENTS

| | | |
|---|---|---|
| WO | WO 97/41897 | 11/1997 |
| WO | WO 2006/090110 | 8/2006 |
| WO | WO 2007/120500 | 10/2007 |
| WO | WO 2008/017962 | 2/2008 |
| WO | WO 2009/117572 | 9/2009 |

OTHER PUBLICATIONS

Zhu, D. et al. "Formation of Whey Protein Isolate (WPI)—Dextran Conjugates in Aqueous Solutions" *Journal of Agricultural and Food Chemistry*, 2008, pp. 7113-7118, vol. 56.

Zhu, D. et al. "Physicochemical and Emulsifying Properties of Whey Protein Isolate (WPI)—Dextran Conjugates Produced in Aqueous Solution" *Journal of Agricultural and Food Chemistry*, 2010, pp. 2988-2994, vol. 58.

Akhtar, M. et al. "Whey protein-maltodextrin conjugates as emulsifying agents: An alternative to gum arabic," *Food Hydrocolloids*, 2007, pp. 607-616, vol. 21.

Alting, A.C. et al. "Acid-induced Cold Gelation of Globular Proteins: Effects of Protein Aggregate Characteristics and Disulfide Bonding on Rheological Properties," *Journal of Agricultural and Food Chemistry*, 2004, pp. 623-631, vol. 52.

Eissa, A.S. et al. "Acid-Induced Gelation of Enzymatically Modified, Preheated Whey Proteins," *Jounral of Agricultural and Food Chemistry*, 2005, pp. 5010-5017, vol. 53.

McGarrahan, E.T. "Considerations necessary to provide for sterilized milk and milk products in hermetically sealed, nonrefrigerated containers," *Journal of Dairy Science*, 1982, pp. 2023-2034, vol. 65, No. 10.

Vardhanabhuti, B. et al. "Interactions between β-lactoglobulin and dextran sulfate at near neutral pH and their effect on thermal stability," *Food Hydrocolloids*, 2009, pp. 1511-1520, vol. 23, No. 6.

Yong, Y.H.Y. et al. "Effects of Caseins on Thermal Stability of Bovine β-Lactoglobulin," *Journal of Agricultural and Food Chemistry*, 2008, pp. 10352-10358, vol. 56.

Zhang, W. et al. "Microemulsions as Nanoreactors to Produce Whey Protein Nanoparticles with Enhanced Heat Stability by Sequential Enzymatic Cross-Linking and Thermal Pretreatments," *Journal of Agricultural and Food Chemistry*, 2009, pp. 9181-9189, vol. 57, No. 19.

Zhang, W. et al. "Microemulsions as Nanoreactors to Produce Whey Protein Nanoparticles with Enhanced Heat Stability by Thermal Pretreatment," *Food Chemistry*, 2010, pp. 1318-1325, vol. 119, No. 4.

*Primary Examiner* — David Lukton
(74) *Attorney, Agent, or Firm* — Saliwanchik, Lloyd & Eisenschenk

(57) ABSTRACT

The subject invention pertains to methods of making crosslinked protein-carbohydrate conjugates (CPCCs) and uncrosslinked protein-carbohydrate conjugates (PCCs) that are heat, pH and salt stable. Methods of stabilizing CPCCs and PCCs are also provided. The PCCs and CPCCs formed according to the methods disclosed herein are useful in the food industry and for loading with substances of interest.

16 Claims, 63 Drawing Sheets

FIG. 27

HEAT STABLE PROTEIN INGREDIENTS

CROSS-REFERENCE TO RELATED APPLICATION

This application claims the benefit of U.S. Provisional Patent Application 61/329,931, filed Apr. 30, 2010, the disclosure of which is hereby incorporated by reference in its entirety.

BACKGROUND OF THE INVENTION

Molecular bases of thermal denaturation and aggregation of whey protein have been extensively researched. When heated to a temperature above about 65° C., whey protein denatures and exposes hydrophobic amino acids originally imbedded at the globular state, facilitating intermolecular attraction. The possibility of intermolecular aggregation depends mostly on electrostatic interactions, hydrophobic interactions, and intra- and intermolecular disulfide bonds via sulfhydryl-disulfide interchange. The significance of these physical and chemical forces to protein aggregation is manipulated by the thermodynamic state (native, partially or completely denatured molecular structures), pH, and ionic strength and type. In addition, thermal aggregation of whey protein is influenced by cosolutes such as glycerol, sorbitol, and sucrose that may also co-exist in certain food matrices. Co-solutes may enhance or compromise heat stability of whey proteins, depending on pH, ionic strength and type, and co-solute concentration. Protein aggregation may result in opaque appearance and even gelation when proteins form a three-dimension network within a container. These are undesirable qualities to applications such as transparent beverages.

Improving heat stability of why protein for transparent food products such as functional beverages has been a research topic and problem within the food industry for decades. Preheating whey protein, usually at 80-90° C. for 15 min or longer, at neutral pH and a low ionic strength produces filament-like aggregates (also called polymers in some papers). Preheated whey protein has much enhanced heat stability at neutral pH when reheated, resulting from some irreversible physical and chemical bonds. The denatured protein can be used to produce "cold-set gels" that are formed after addition of salt or acidification without additional heating.

It is also known that preheating or denaturation by a reducing agent such as dithiothreitol exposes amino acids originally embedded in globular structures of native α-lactalbumin and β-lactoglobulin, and this allows the cross-linking by transglutaminase (TGase). Excellent heat stability of enzymatically cross-linked whey protein at a concentration of 1% or lower was observed more than two decades ago and was later repeated by others. However, heat stability at a protein content of 5% or higher however remained a challenge, especially when added with salt.

High protein beverages have an average of 6% protein (Vardhanabhuti et al., 2009). Several strategies to improve heat stability of whey protein at relatively high concentrations have been developed. Caseins are chaperones that can reduce the degree of protein unfolding, aggregation, and precipitation. 2% w/v of high purity (>90%) β-casein was observed to be capable of stabilizing 6% w/v β-lactoglobulin solutions at pH 6.0 without salt addition during heating at 90° C. for a period as long as 90 min (Yong and Foegeding, 2009). Lower purity β-casein however was not able to stabilize β-lactoglobulin. Addition of dextran sulfate at an approximate ratio to β-lactoglobulin (6% w/v) improved heat stability of protein at pH 5.6-6.2 when there was no NaCl (Vardhanabhuti et al., 2009). However, all samples formed gels when the ionic concentration and was increased to 30 mM at pH 6.0. Our recent work (Zhang and Zhong, 2009, 2010) utilized microemulsions as templates to form nanoparticles of whey protein by heat or sequential enzymatic cross-linking and heat. The produced nanoparticles had much improved stability when dispersed at 5% w/v in 50 mM sodium phosphate buffer at pH 6.8 and 100 mM NaCl. The production capacity for nanoparticles however was limited.

The subject application provides a solution to the problem of improving heat stability of proteins, such as whey protein, for use in transparent food products such as functional beverages and provides protein-carbohydrate (e.g., whey protein-carbohydrate) conjugates that are heat stable at high protein content (e.g. around 15% (w/v) in both the presence and absence of salt.

BRIEF SUMMARY OF THE INVENTION

The subject application provides methods of making carbohydrate-protein conjugates. The methods include: combining proteins and sugars/carbohydrates comprising a reducing sugar in an aqueous solution at a ratio of about 10:1 to about 1:10 and then heating the combined elements at a temperature of about 40° C. to about 180° C. to produce sugar/carbohydrate-protein conjugates [PCC(s)]. The combined protein carbohydrate composition can be heated within the aqueous solution or heated by dry heat. Where dry heat is used, the composition can be freeze- or spray dried to obtain a powdered product which can then be heated, for example, in an oven, for a period of about 0.5 to about 48 hours in order for the carbohydrate to be conjugated to the protein via a Maillard reaction. Powdered compositions comprising protein and carbohydrate can also be formed by freeze drying the protein/carbohydrate solutions which can then be heated, for example, in an oven to form a protein-carbohydrate conjugate via a Maillard reaction. In various aspects of the invention, the initial protein carbohydrate solution can be maintained at a pH from about 3.0 to about 9.0.

After recovery of the powdered protein-carbohydrate conjugate, the PCC can be dissolved or suspended in an aqueous solution. To this solution, one or more enzyme capable of cross-linking the protein and/or the carbohydrate elements of the conjugate can be added to the solution to facilitate the crosslinking of one or both elements of the PCC. The methods may further include recovering of the PCC from the solutions in various ways, for example including membrane filtration, chromatography, or simply drying to remove solvent. In certain aspects of the invention, aqueous solutions into which the powdered PCC has been dissolved/suspended are heated prior to enzymatic treatment with one or more enzyme capable of cross-linking the protein and/or the carbohydrate elements of the conjugate. Where this aspect of the invention is practiced, the aqueous solutions are heated at a temperature of between about 50° C. and about 150° C. for a period of about 5 seconds to about 120 minutes, cooled and then treated with one or more enzyme capable of cross-linking the protein and/or the carbohydrate elements of the conjugate.

In any aspect of the invention, the proteins used in the methods can be, for example, soy proteins, caseinates or whey protein.

Sequential treatments were performed by preheating at 80° C. for 15 min followed by 55 U/g WPI of transglutaminase. Sample pH was 7.0 for (A) and (B) and 3.0 for (C) and (D). Samples labeled with a letter "G" indicate formation of gels. Error bars are standard deviations from two replicates.

Figure 17A:
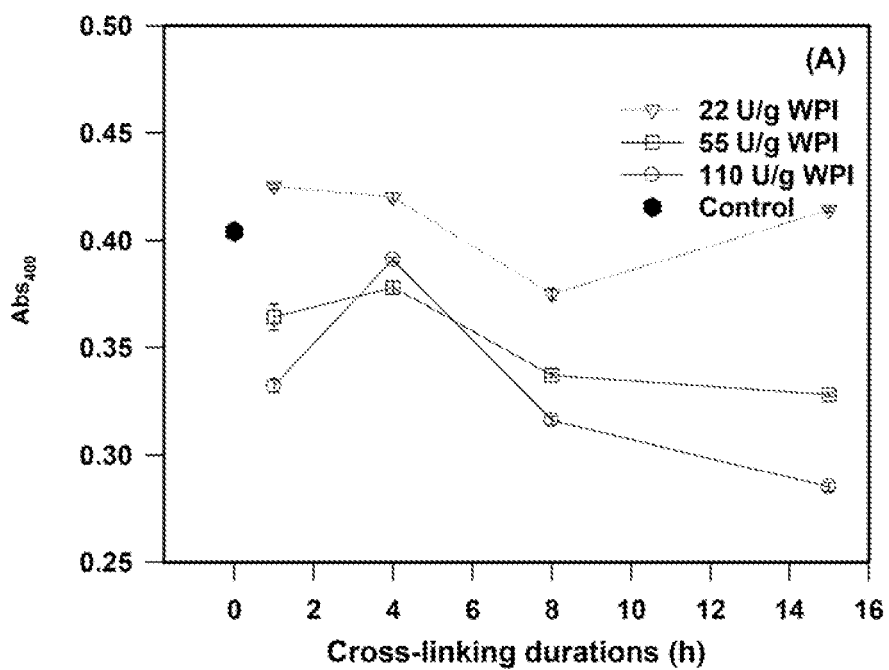
Figure 17B:
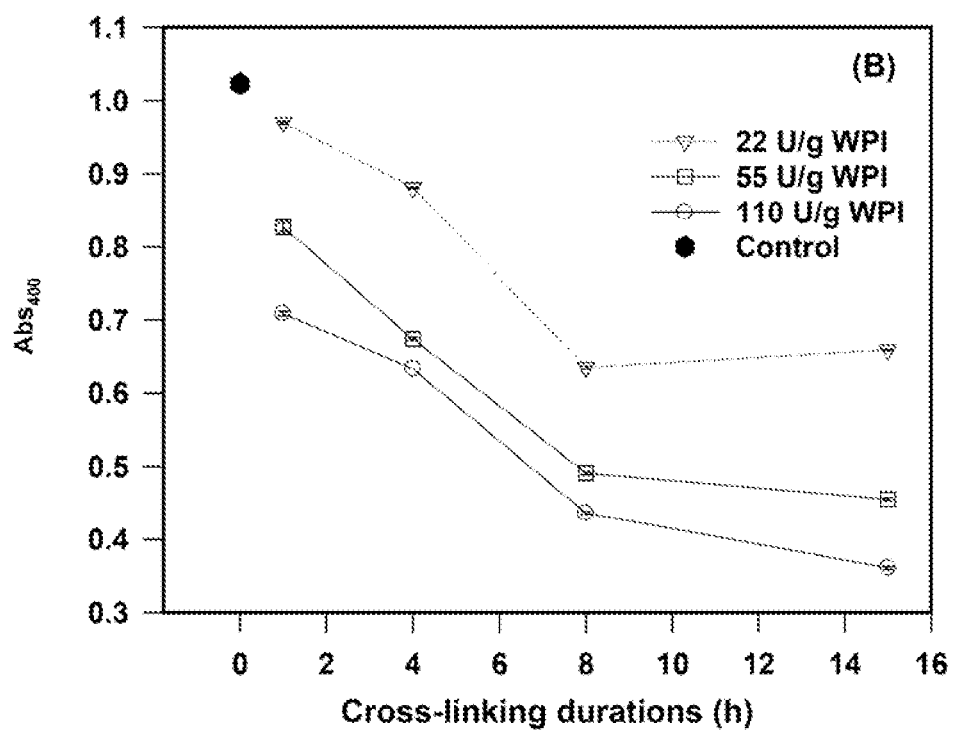
Figure 17C:
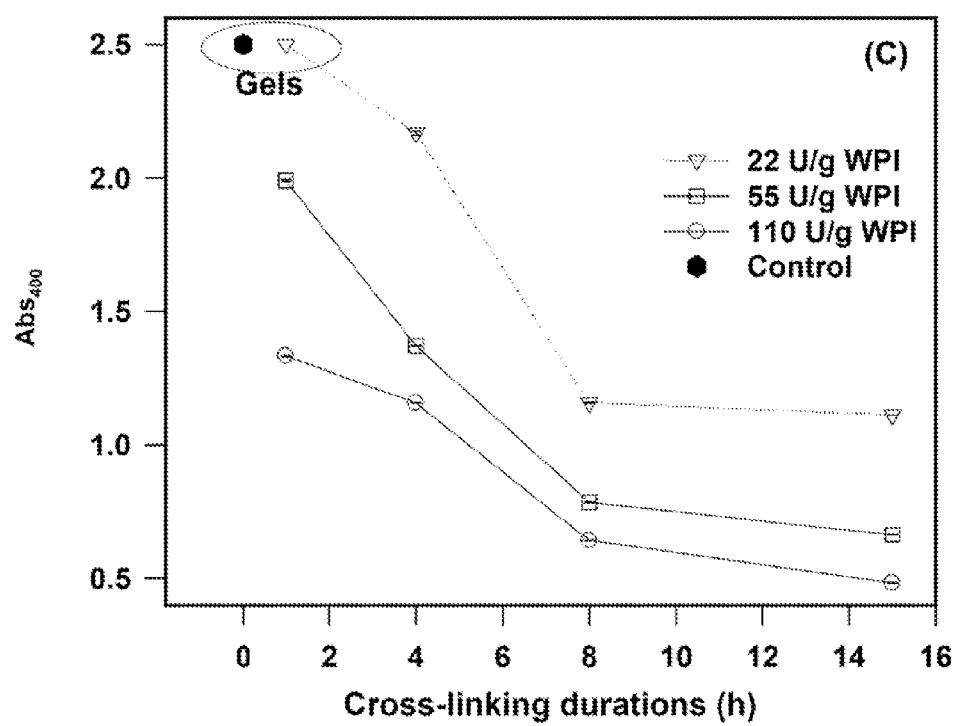

FIGS. 17A-17C. Absorbance of samples at 400 nm after heating at 80° C. for 15 min. 5% w/v WPI samples were adjusted to pH 7.5 and cross-linked by different concentrations of transglutaminase for 1-15 h before adjusting pH 7.0 and (A) 0, (B) 50, and (C) 100 mM NaCl for heat stability tests. Error bars are standard deviations from three replicates.

Figure 18:
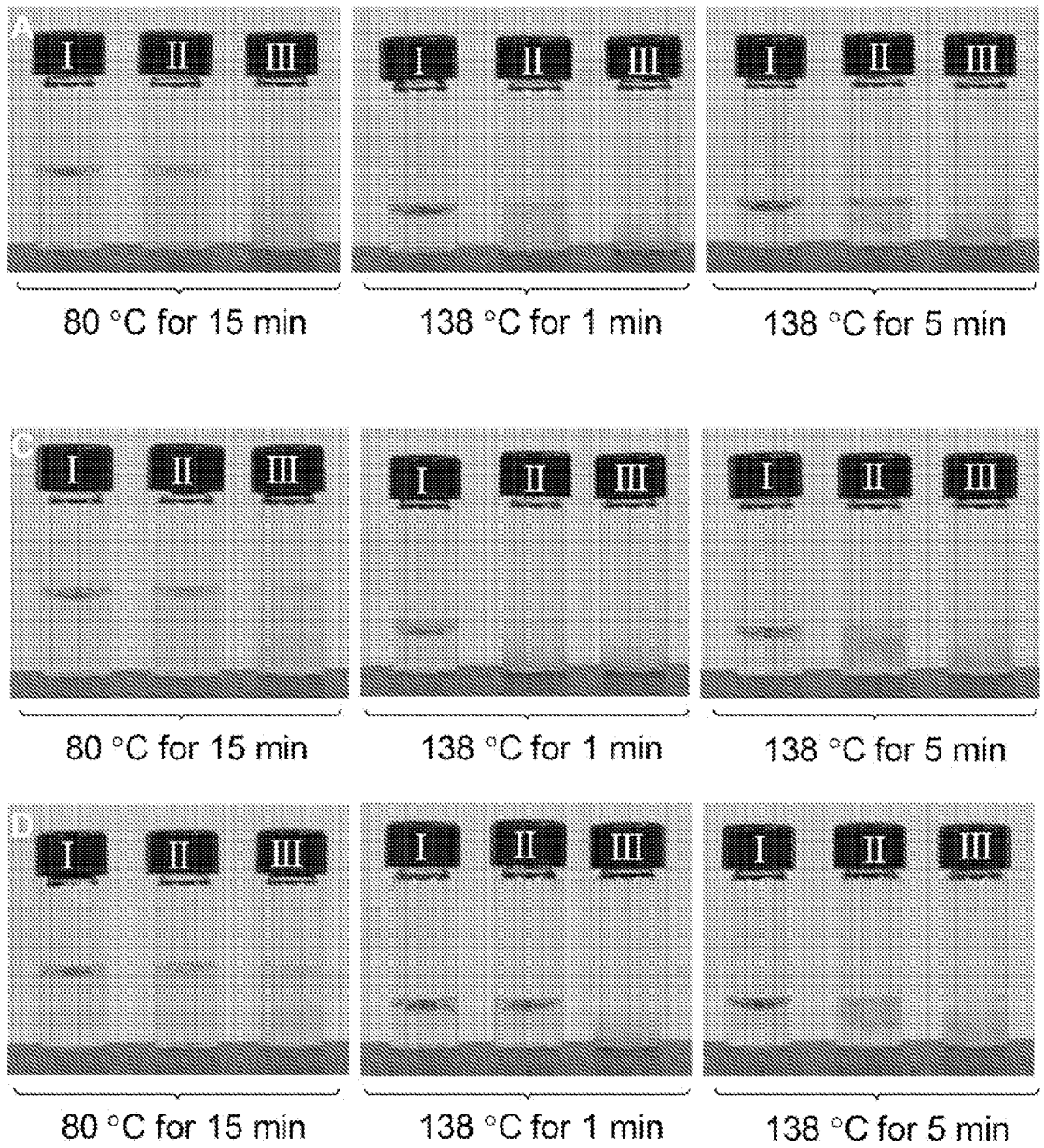
Figure 18:
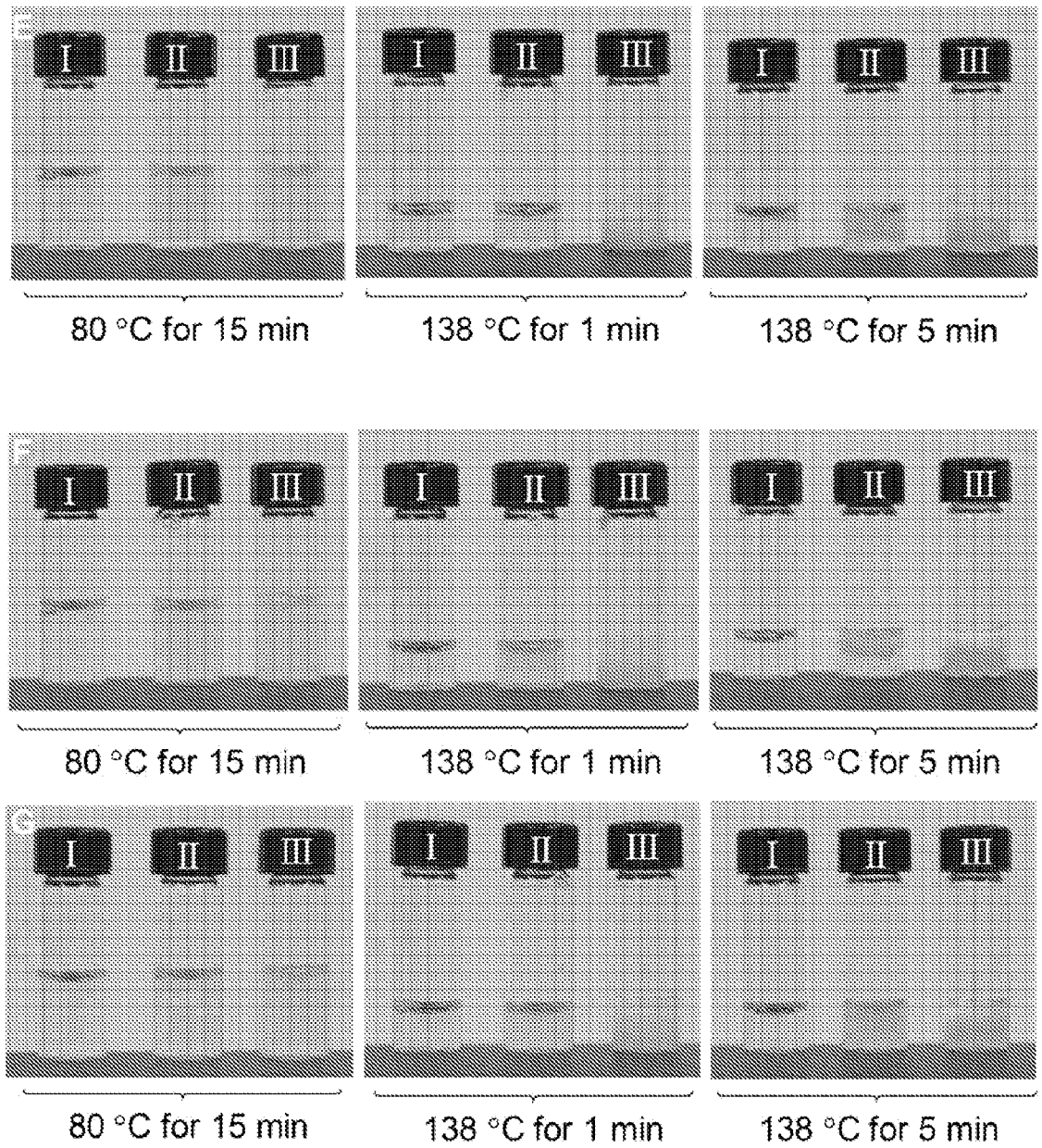
Figure 18:
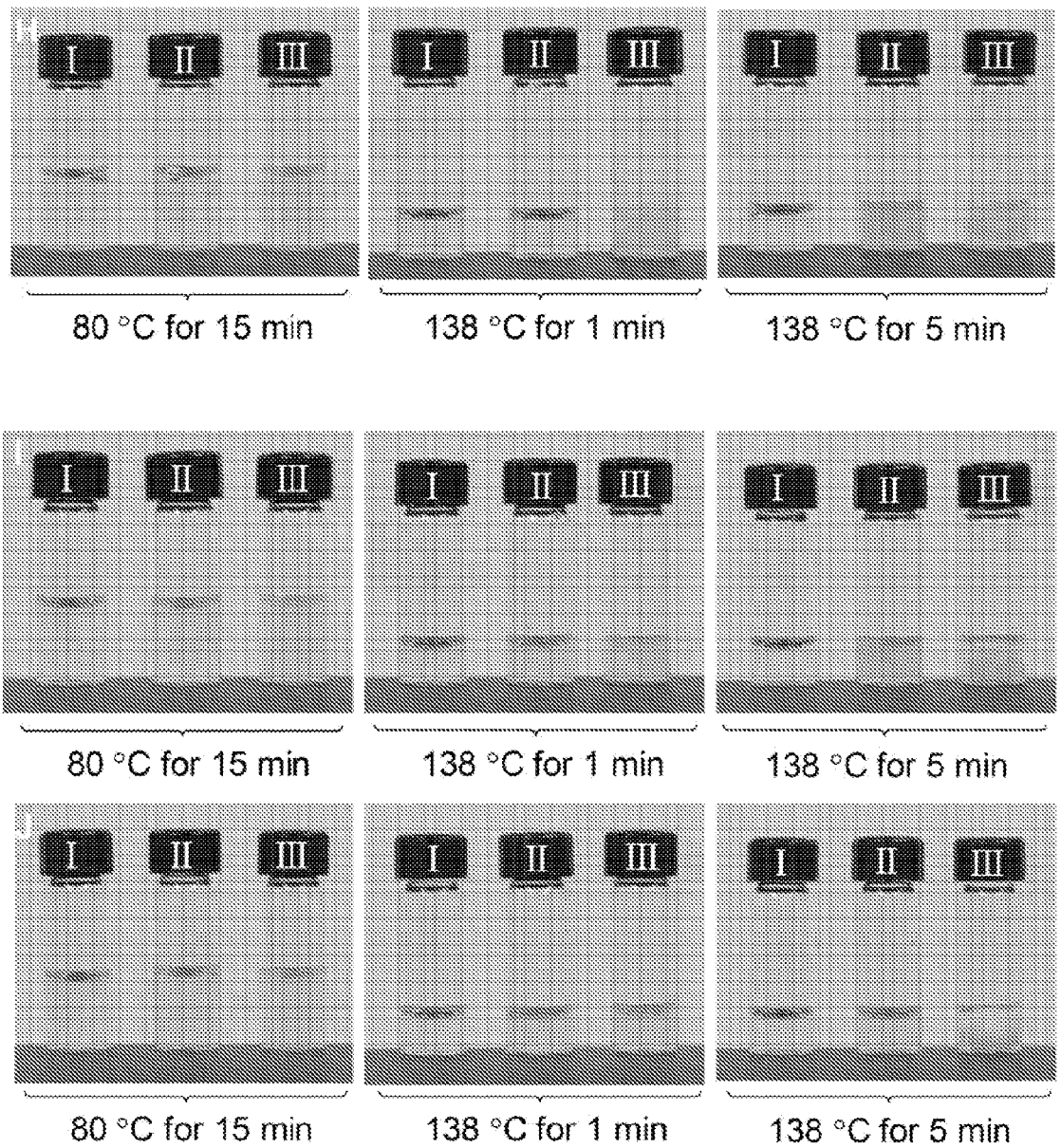
Figure 18:
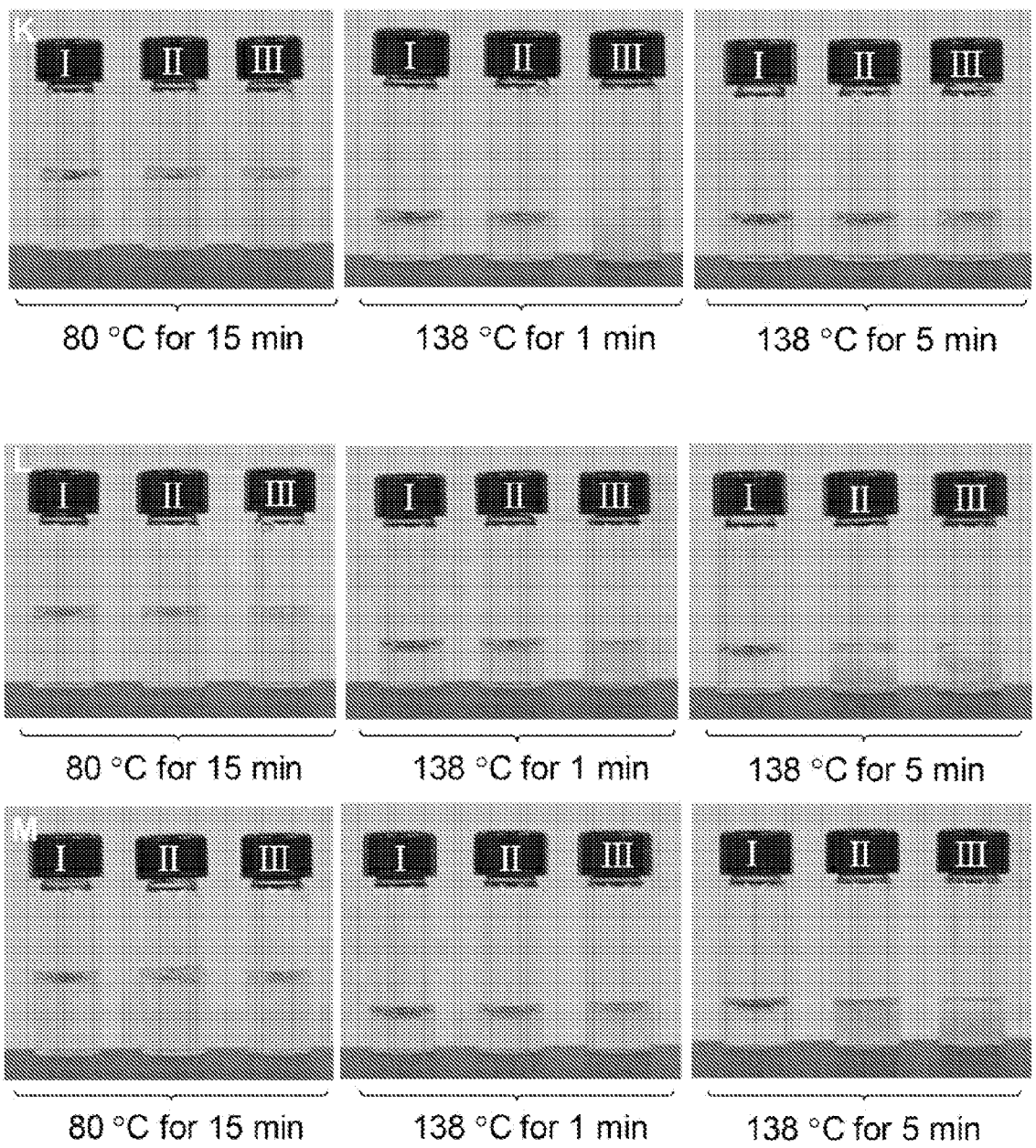
Figure 18:
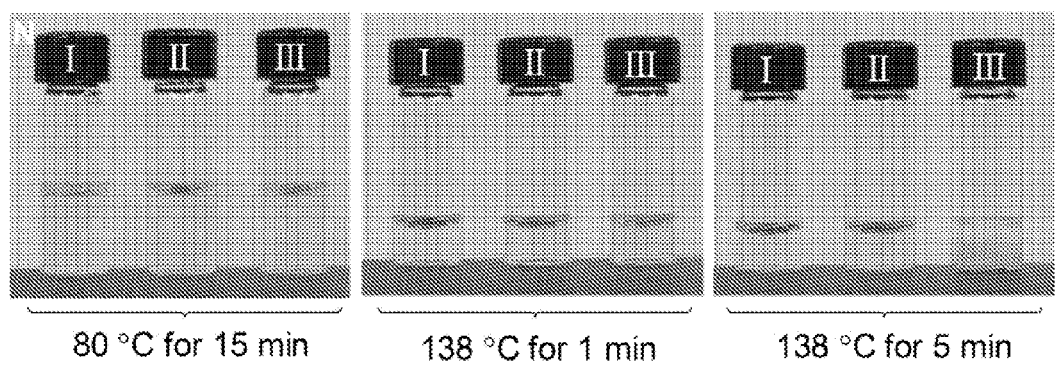

FIG. 18. Photographs of samples after heating at 80° C. for 15 min or 138° C. for 1 or 5 min. 5% w/v WPI samples were adjusted to pH 7.5 and cross-linked by different concentrations of transglutaminase for 1-15 h before adjusting pH 7.0 and NaCl for heat stability tests. Vial labels: I—0 mM NaCl, II—50 mM NaCl, and III—100 mM NaCl. Image codes correspond to treatments in the following Table.

| Code | TGase level | TGase treatment time (h) | Code | TGase level | TGase treatment time (h) |
|---|---|---|---|---|---|
| A | None (control) | | | | |
| C | 22 U/g WPI | 1 | I | 22 U/g WPI | 8 |
| D | 55 U/g WPI | 1 | J | 55 U/g WPI | 8 |
| E | 110 U/g WPI | 1 | K | 110 U/g WPI | 8 |
| F | 22 U/g WPI | 4 | L | 22 U/g WPI | 15 |
| G | 55 U/g WPI | 4 | M | 55 U/g WPI | 15 |
| H | 110 U/g WPI | 4 | N | 110 U/g WPI | 15 |

Figure 19A:
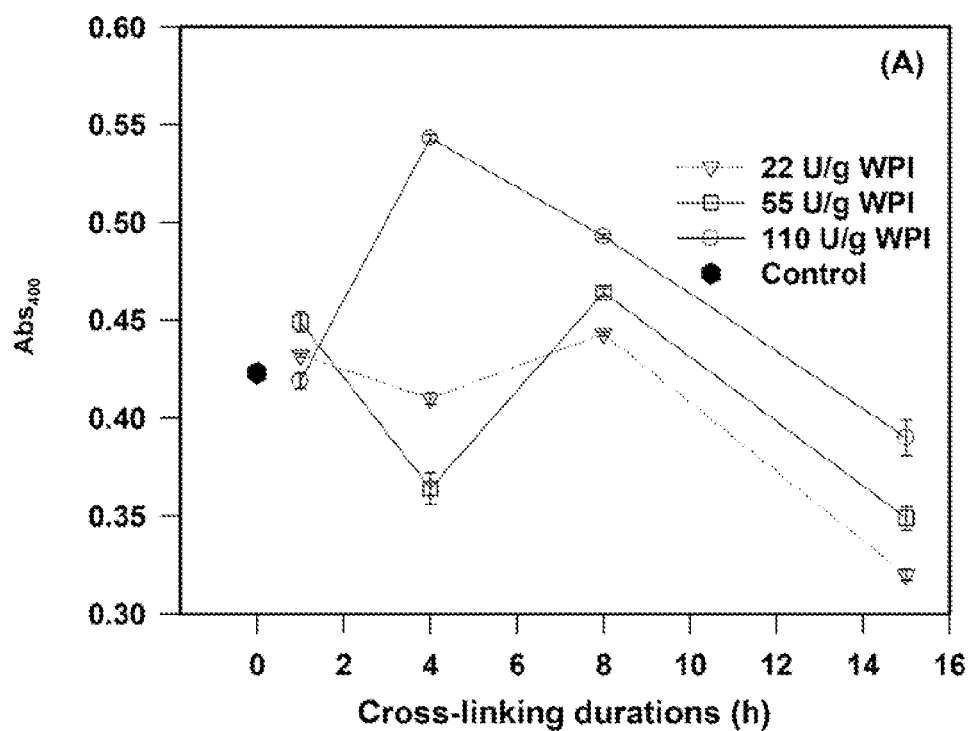
Figure 19B:
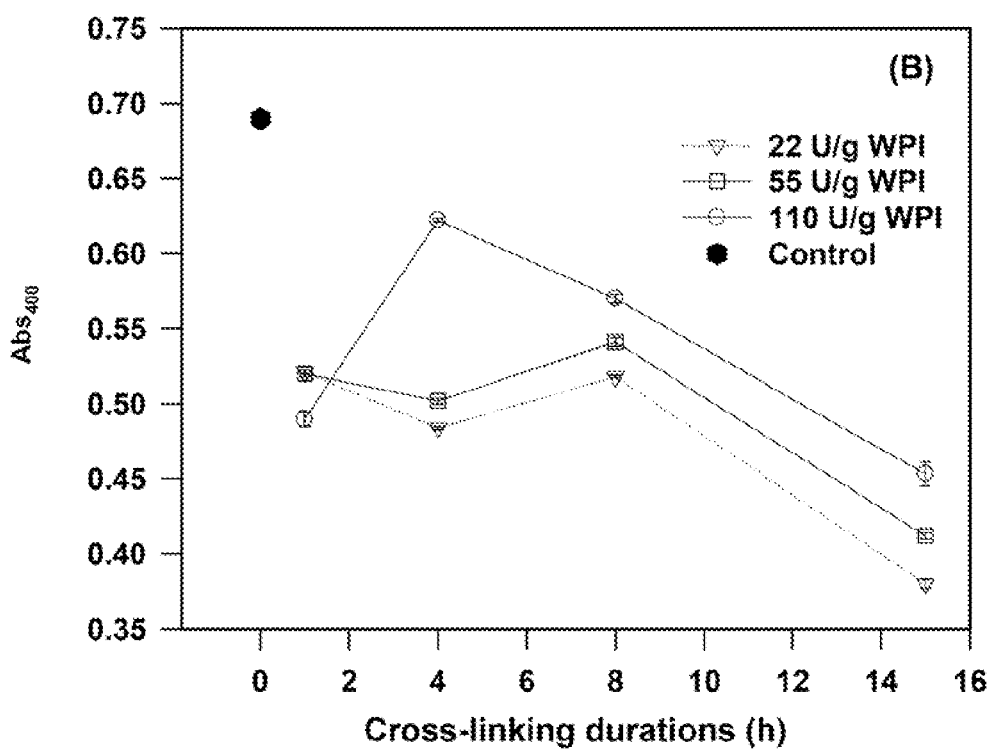
Figure 19C:
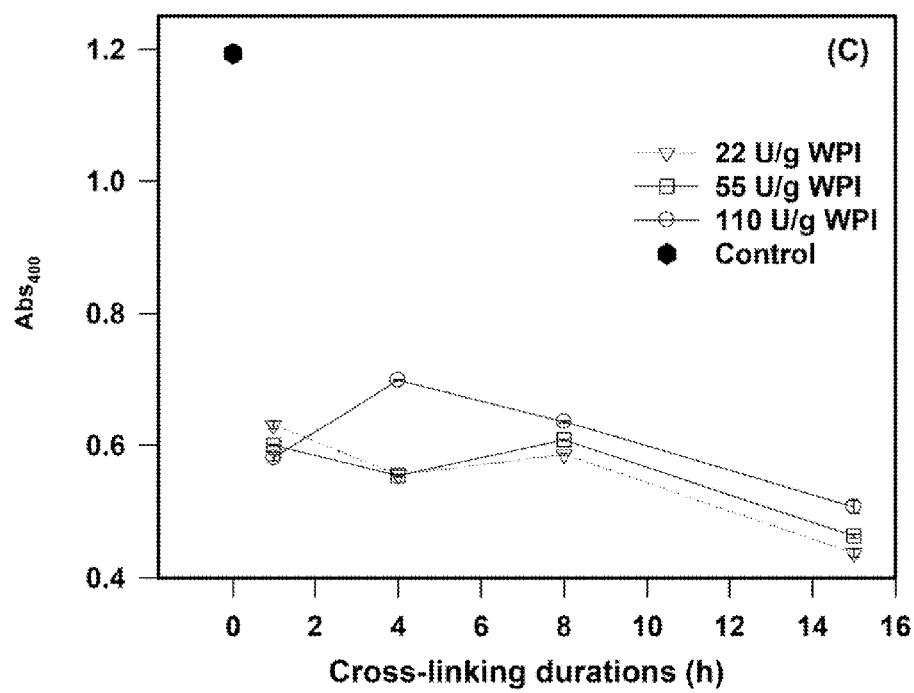

FIGS. 19A-19C. Absorbance of samples at 400 nm after heating at 80° C. for 15 min. 5% w/v WPI samples were adjusted to pH 7.5, preheated at 80° C. for 15 min, and then cross-linked by different concentrations of transglutaminase for 1-15 h before adjusting pH 7.0 and (A) 0, (B) 50, and (C) 100 mM NaCl for heat stability tests. Error bars are standard deviations from three replicates.

Figure 20:
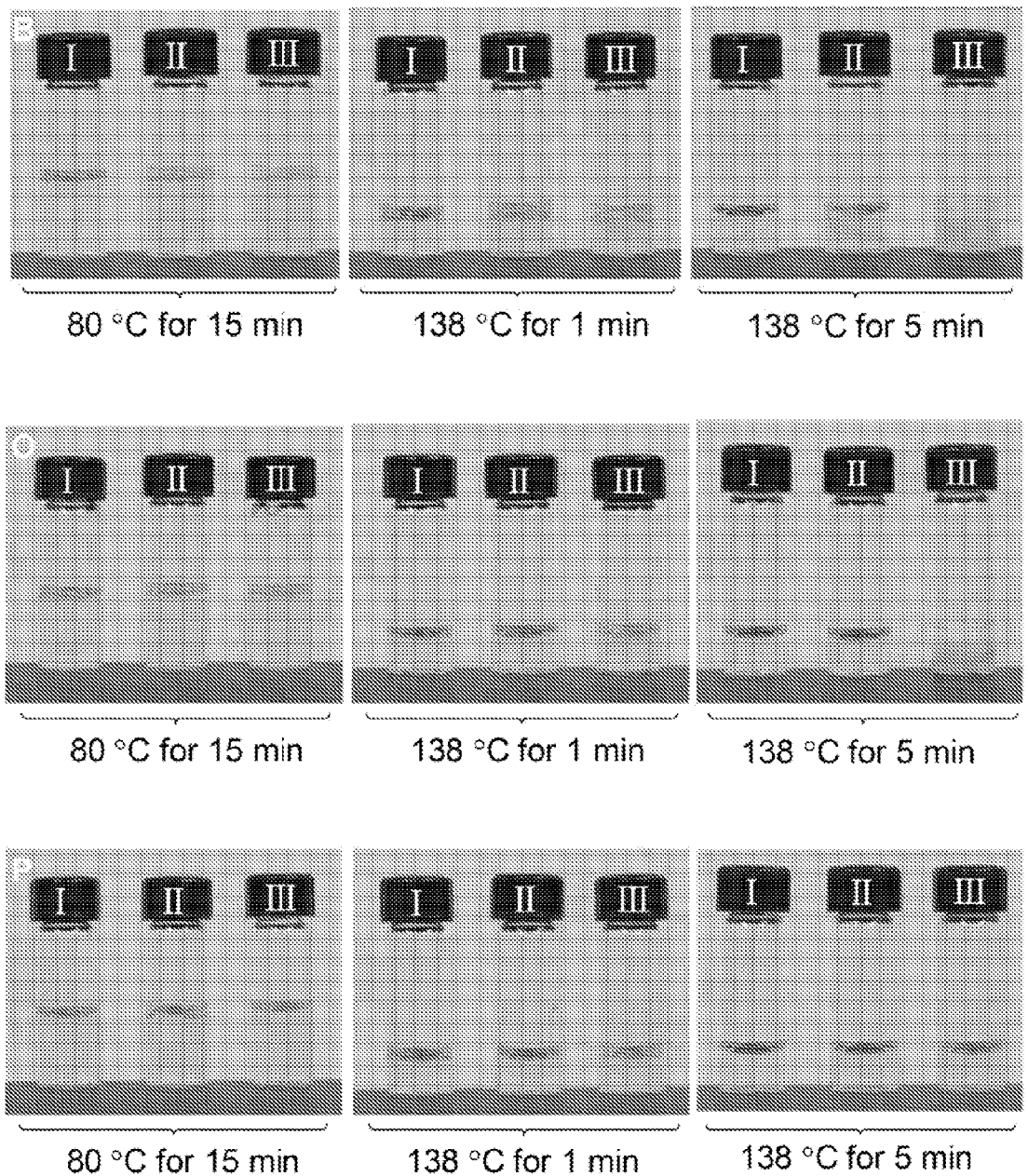
Figure 20:
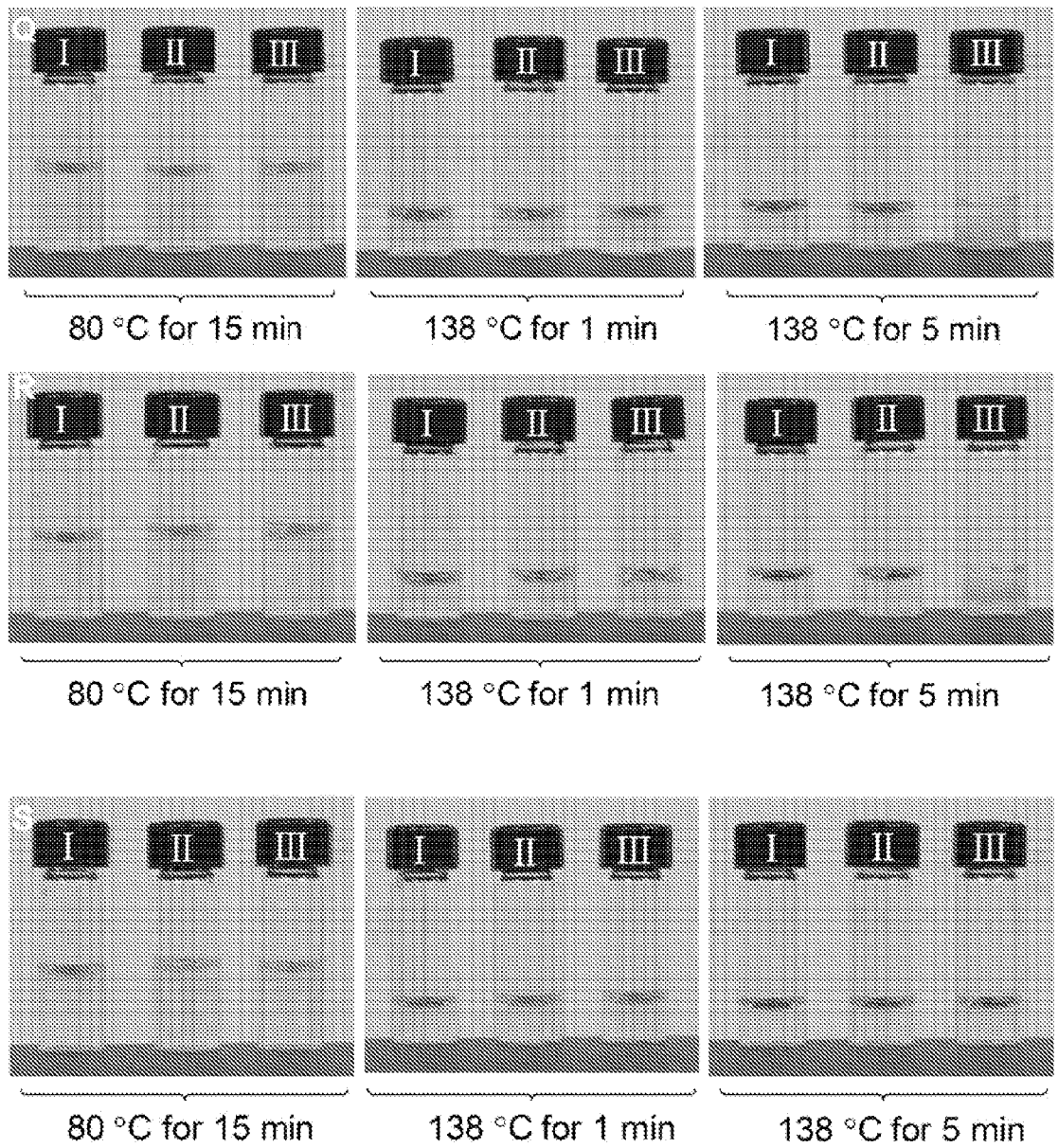
Figure 20:
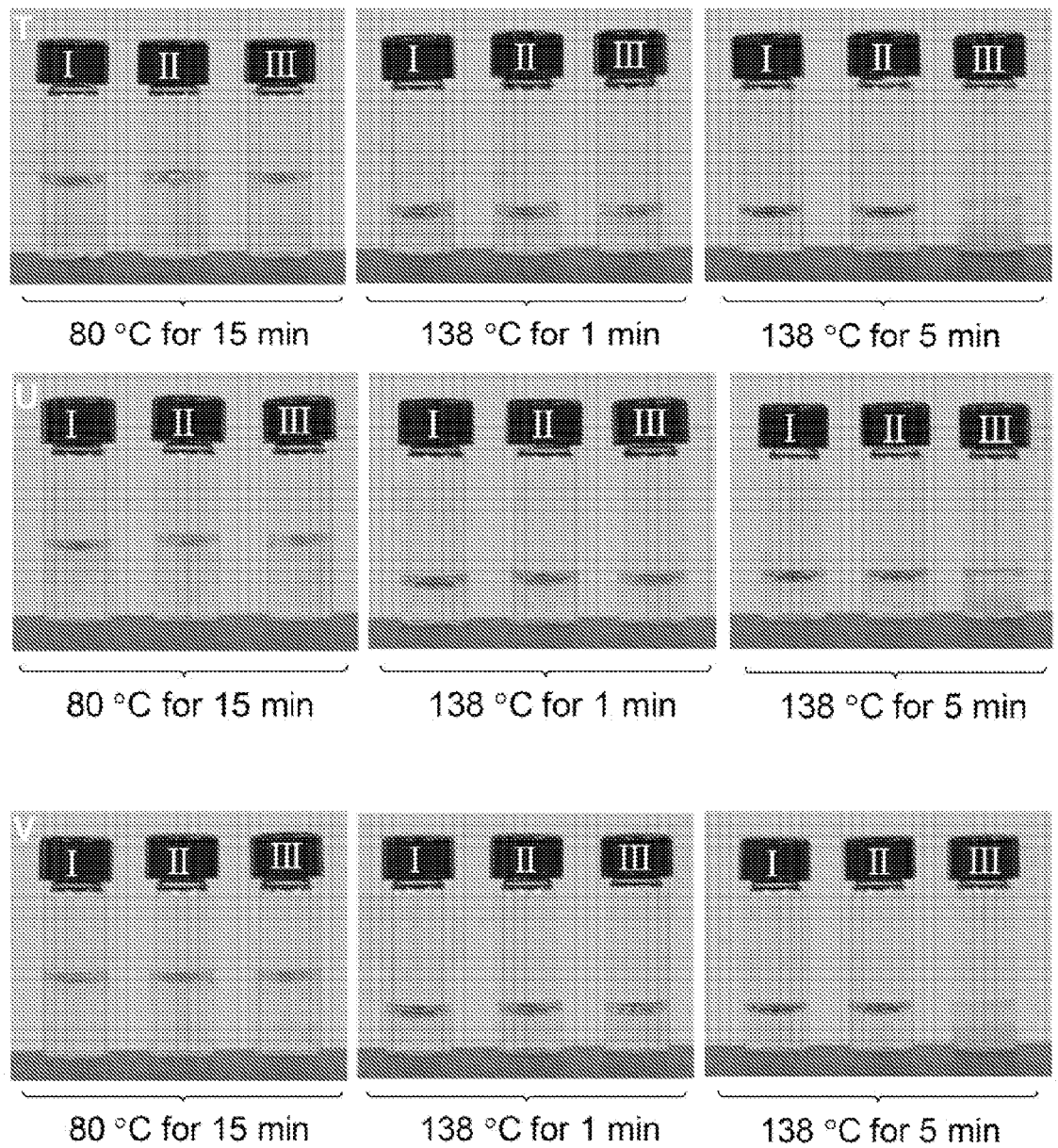
Figure 20:
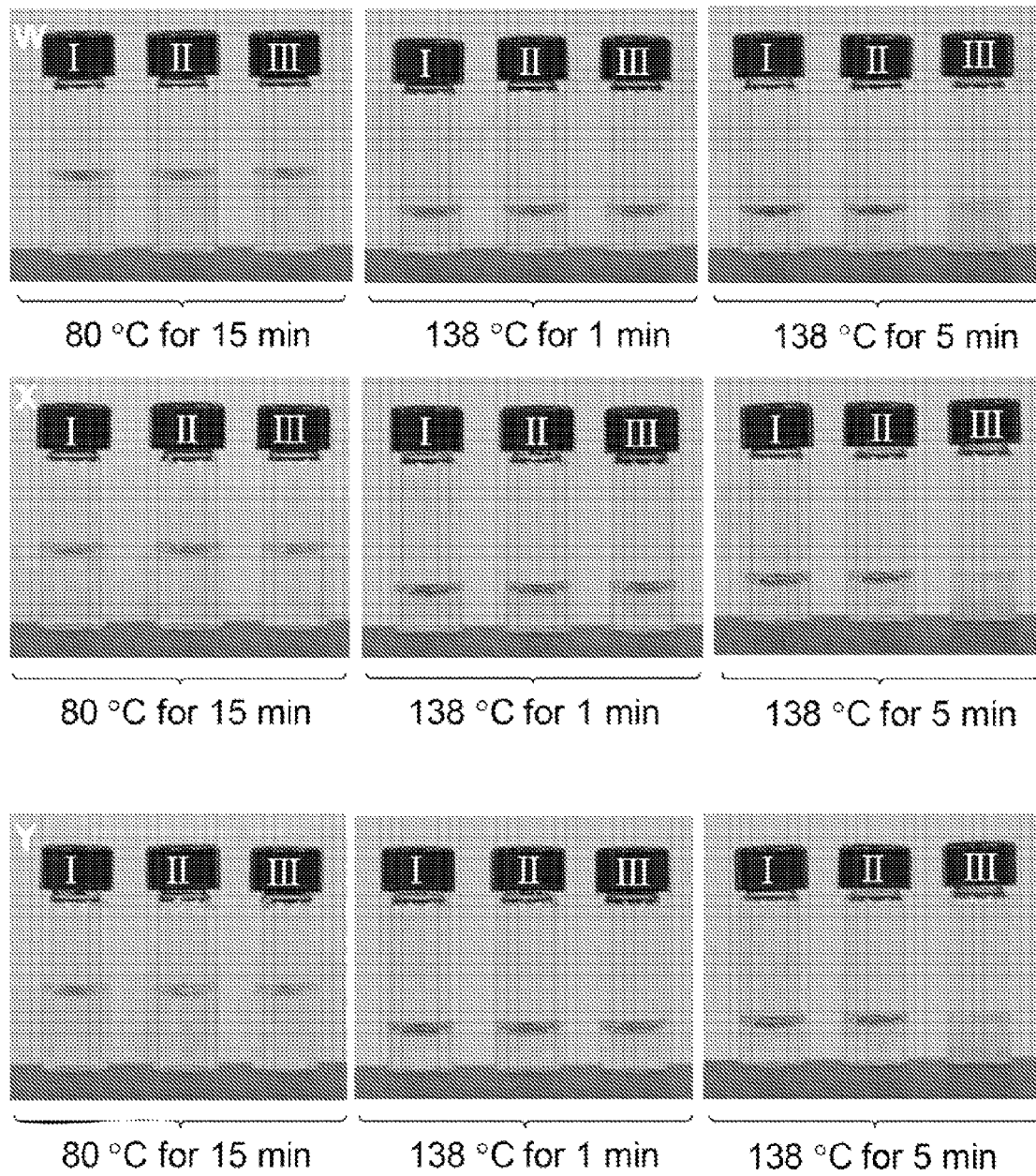
Figure 20:
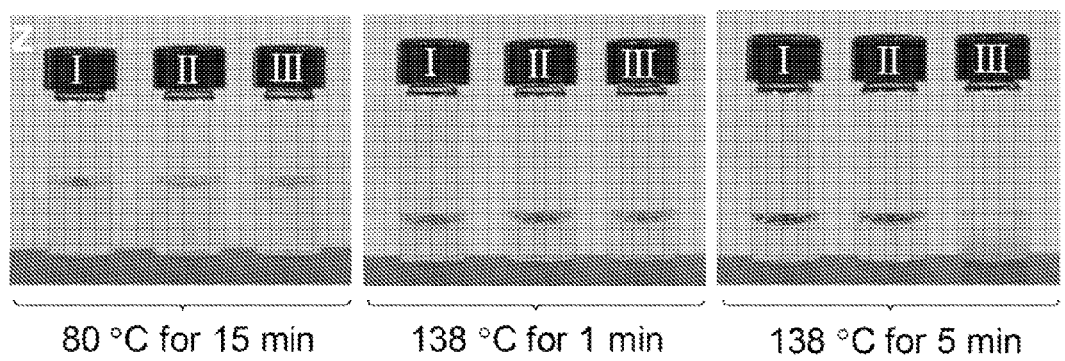
Figure 21A:
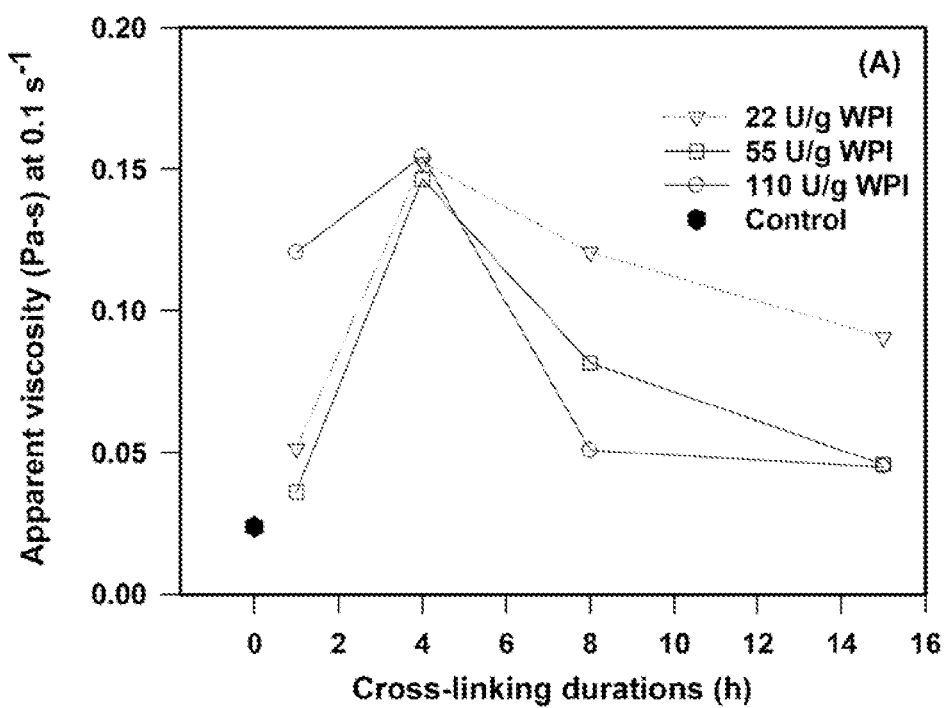
Figure 21B:
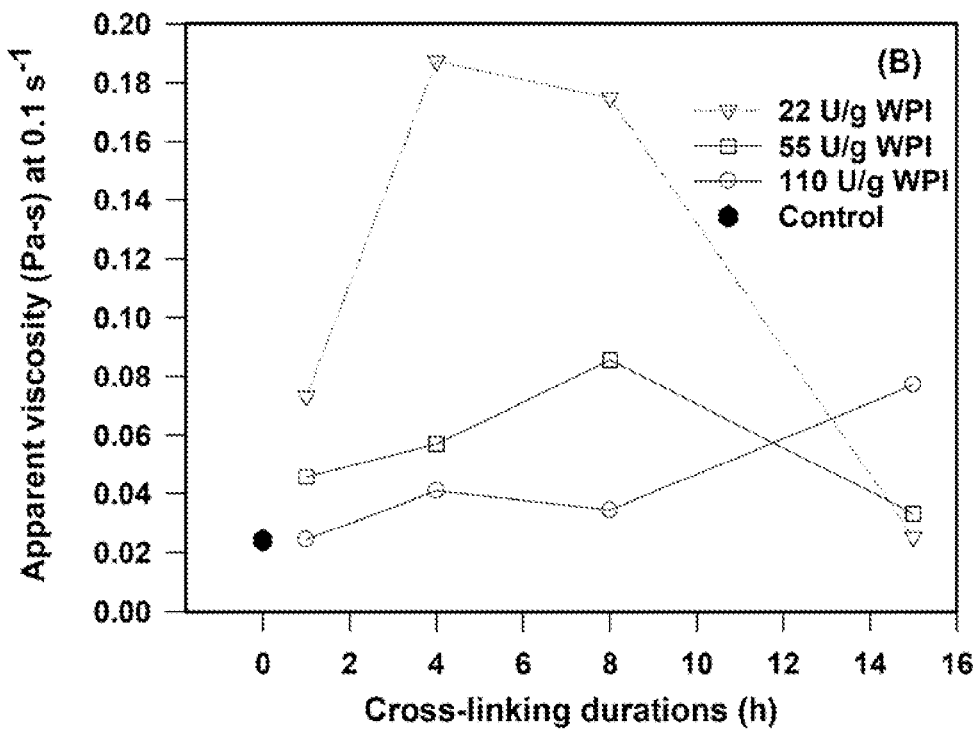
Figure 21C:
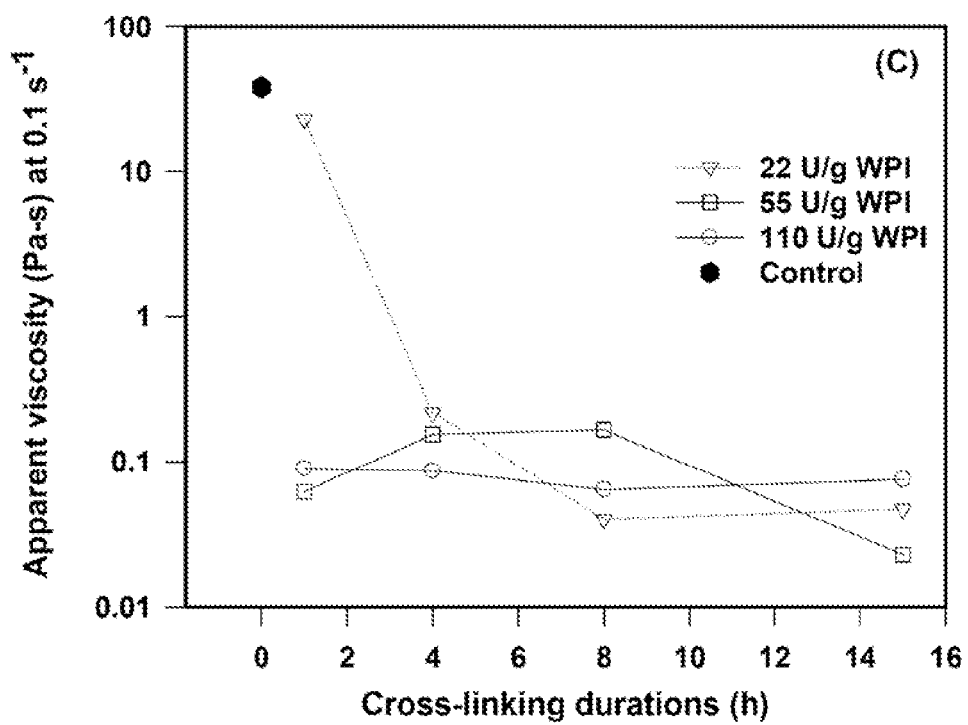
Figure 21D:
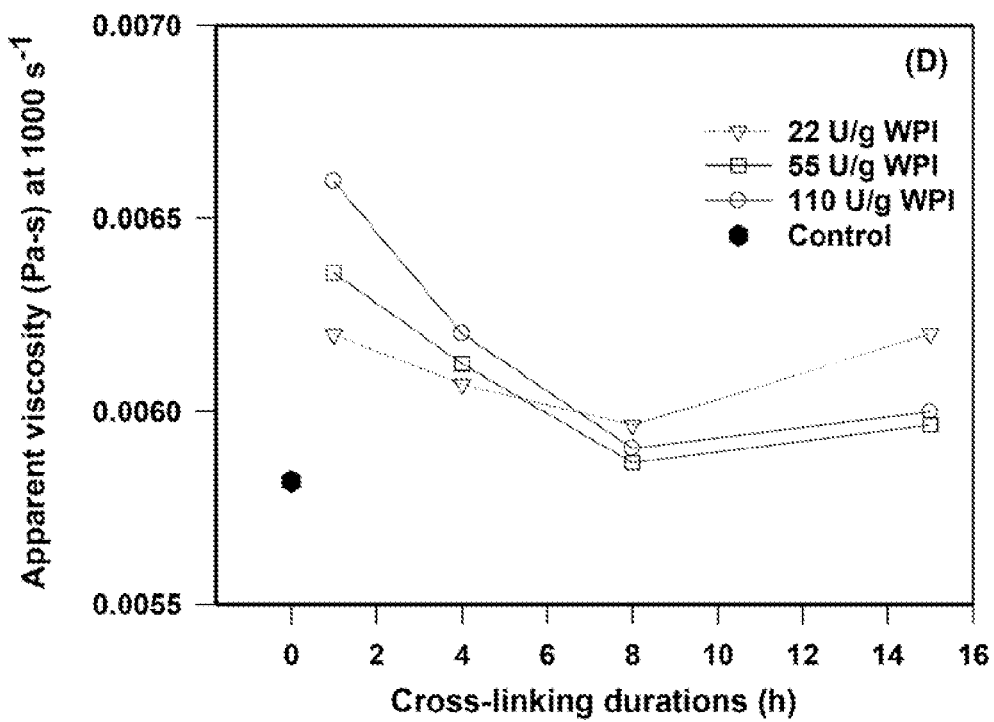
Figure 21E:
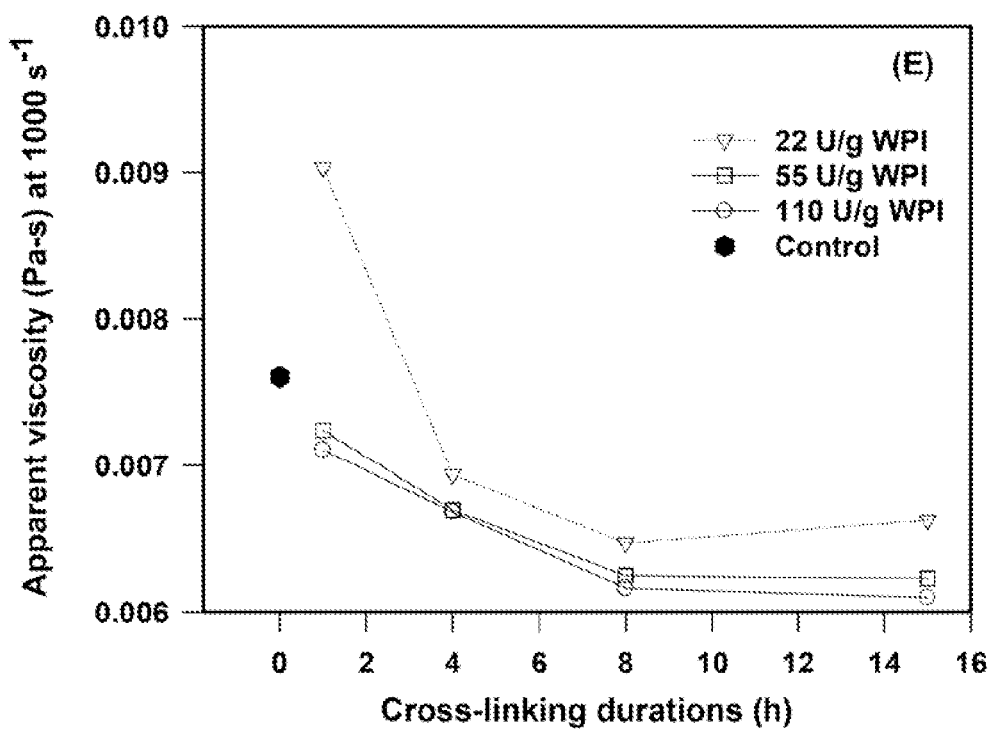
Figure 21F:
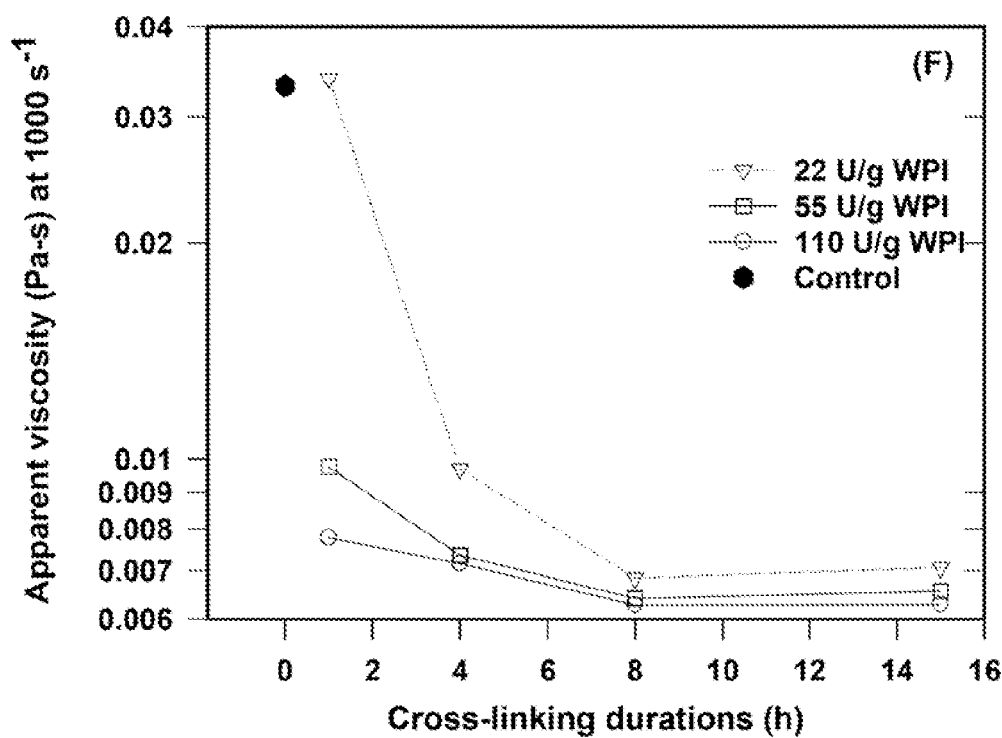
Figure 22A:
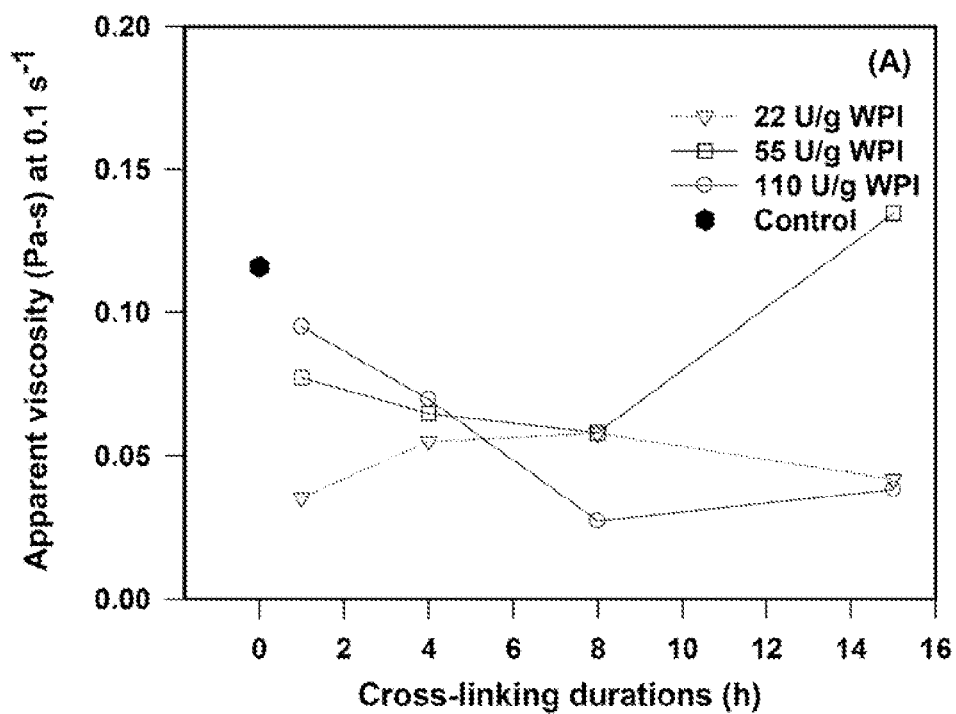
Figure 22B:
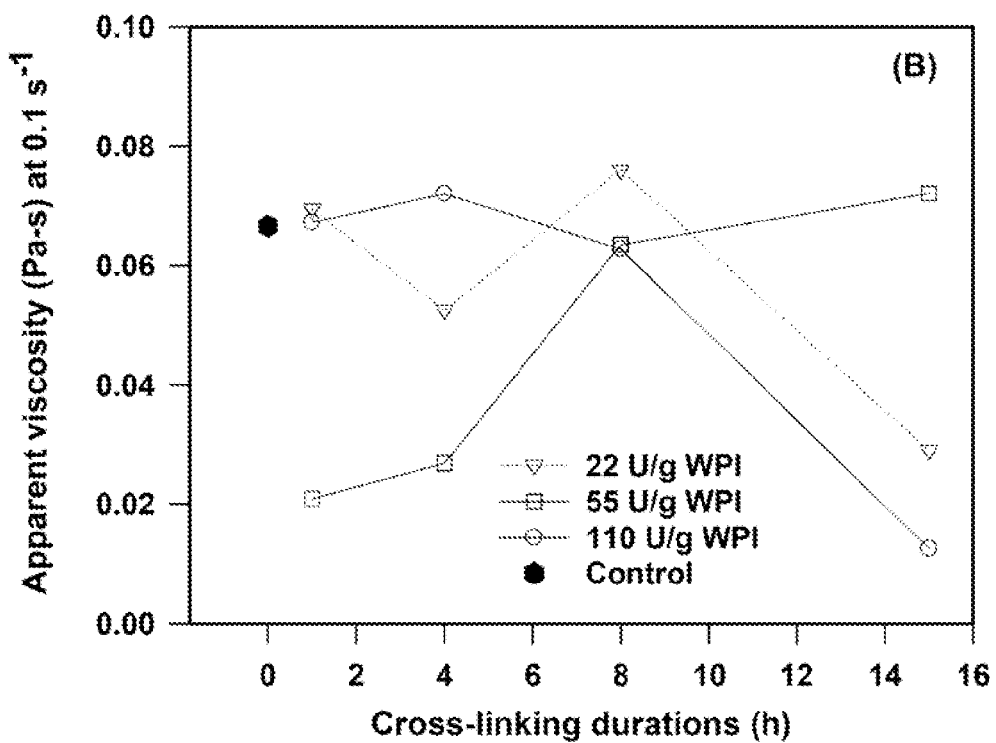
Figure 22C:
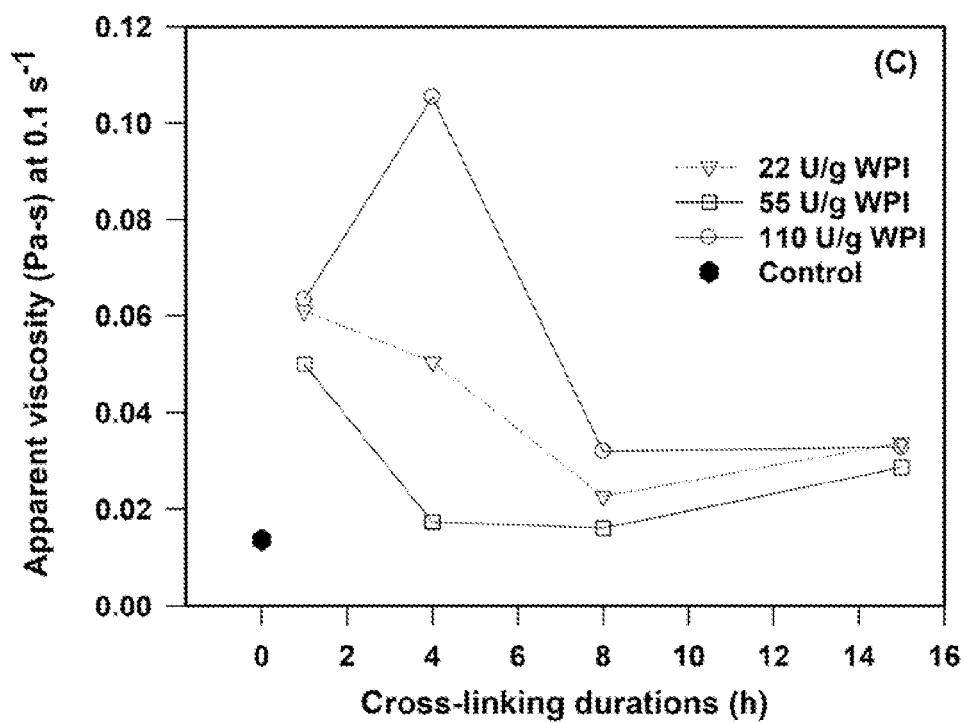
Figure 22D:
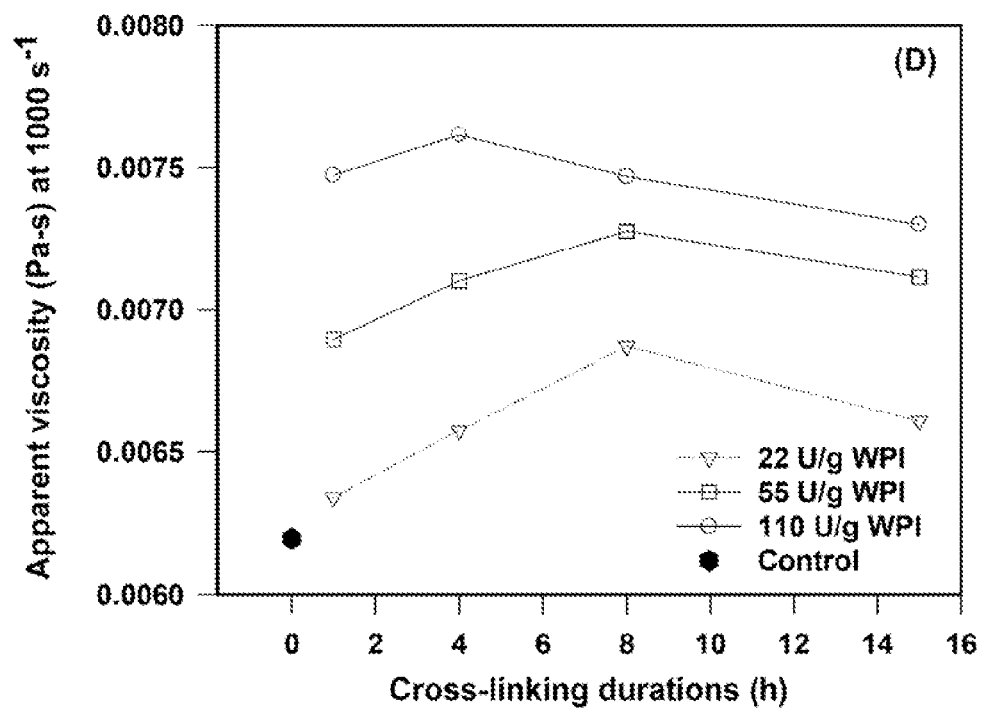
Figure 22E:
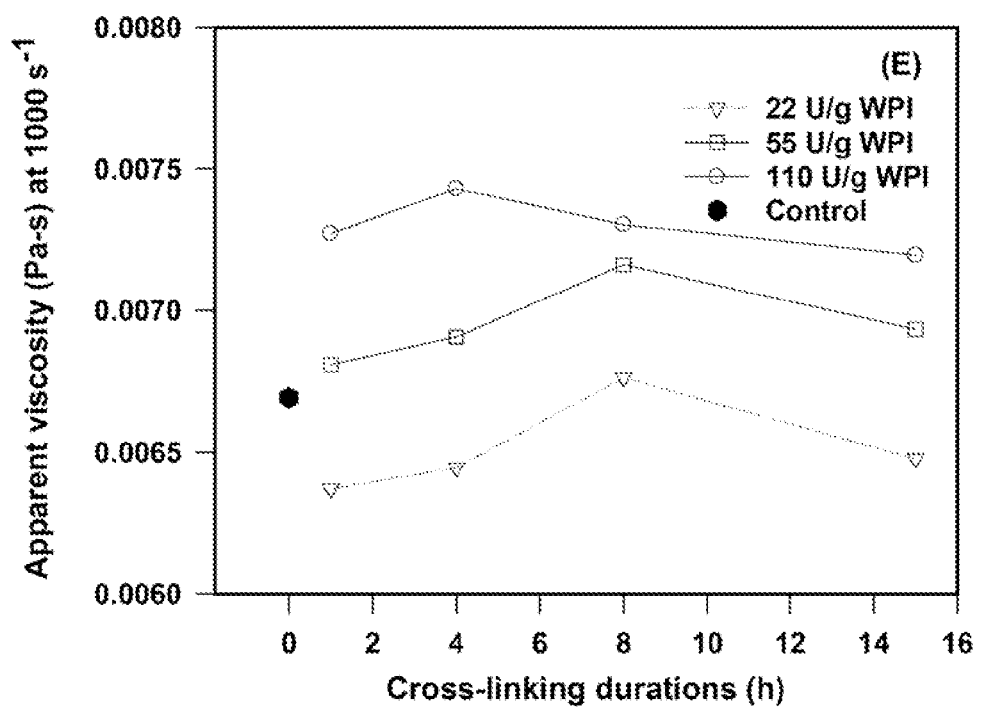
Figure 22F:
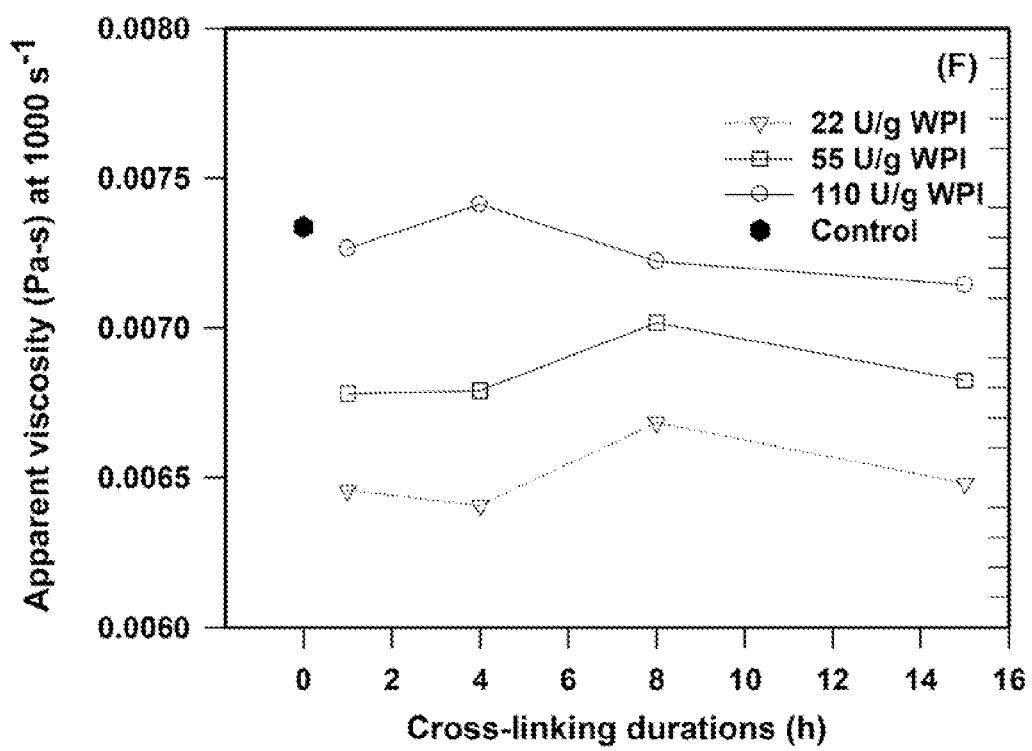

FIG. 20. Photographs of samples after heating at 80° C. for 15 min or 138° C. for 1 or 5 min. 5% w/v WPI samples were adjusted to pH 7.5, preheated at 80° C. for 15 min, and cross-linked by different concentrations of transglutaminase for 0 (native WPI), 1, 4, 8, and 15 h before adjusting pH 7.0 and NaCl for heat stability tests. Vial labels: I—0 mM NaCl, II—50 mM NaCl, and III—100 mM NaCl. Image codes correspond to treatments in the following Table.

| Code | TGase level | TGase treatment time (h) | Code | TGase level | TGase treatment time (h) |
|---|---|---|---|---|---|
| B | None (control) | | | | |
| O | 22 U/g WPI | 1 | U | 22 U/g WPI | 8 |
| P | 55 U/g WPI | 1 | V | 55 U/g WPI | 8 |
| Q | 110 U/g WPI | 1 | W | 110 U/g WPI | 8 |
| R | 22 U/g WPI | 4 | X | 22 U/g WPI | 15 |
| S | 55 U/g WPI | 4 | Y | 55 U/g WPI | 15 |
| T | 110 U/g WPI | 4 | Z | 110 U/g WPI | 15 |

FIGS. 21A-21F. Apparent viscosities of samples at 20° C. presented at two shear rates of 0.1 (A-C) and 1000 (D-F) $s^{-1}$. 5% w/v WPI samples were adjusted to pH 7.5 and cross-linked by different concentrations of transglutaminase for 1-15 h before adjusting to pH 7.0 and 0 (A and D), 50 (B and E), and 100 (C and F) mM NaCl for heating at 80° C. for 15 min.

FIGS. 22A-22F. Apparent viscosities of samples at 20° C. presented at two shear rates of 0.1 (A-C) and 1000 (D-F) $s^{-1}$. 5% w/v WPI samples were adjusted to pH 7.5, preheated at 80° C. for 15 min, and cross-linked by different concentrations of transglutaminase for 1-15 h before adjusting to pH 7.0 and 0 (A and D), 50 (B and E), and 100 (C and F) mM NaCl for heating at 80° C. for 15 min.

Figure 23A:
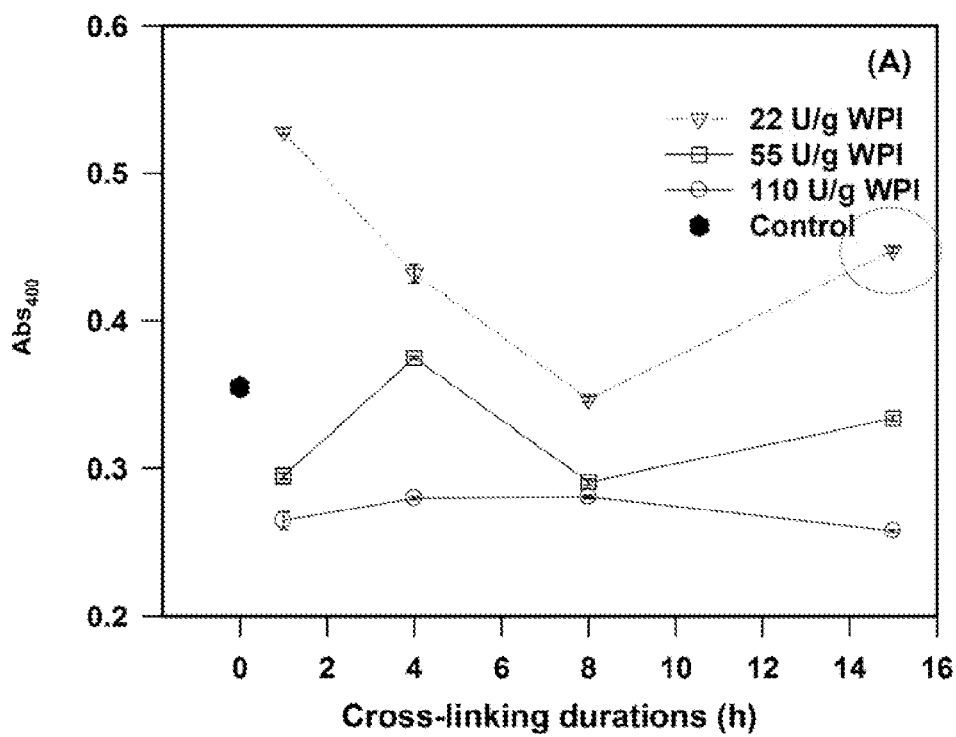
Figure 23B:
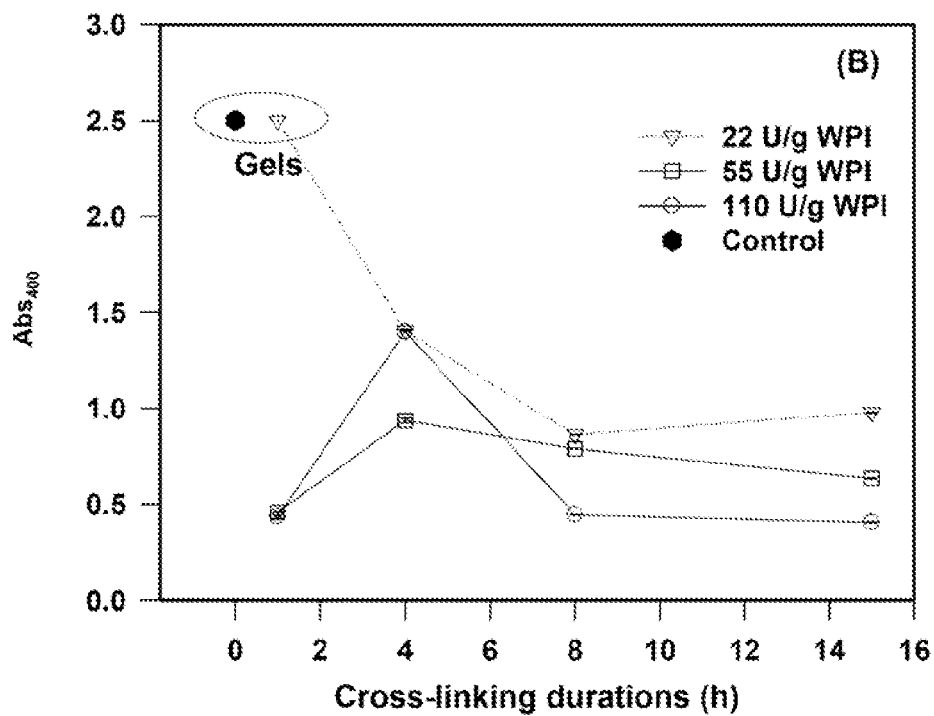
Figure 23C:
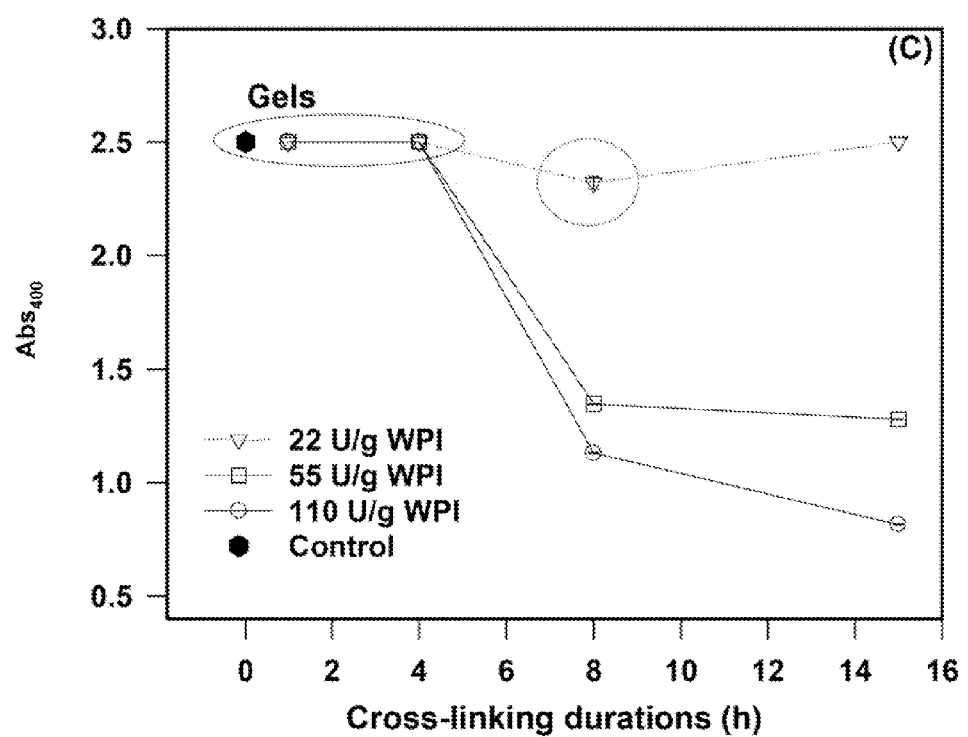

FIGS. 23A-23C. Absorbance of samples at 400 nm after heating at 138° C. for 1 min. 5% w/v WPI samples were adjusted to pH 7.5 and cross-linked by different concentrations of transglutaminase for 1-15 h before adjusting pH 7.0 and (A) 0, (B) 50, and (C) 100 mM NaCl for heat stability tests. Error bars are standard deviations from three replicates.

Figure 24A:
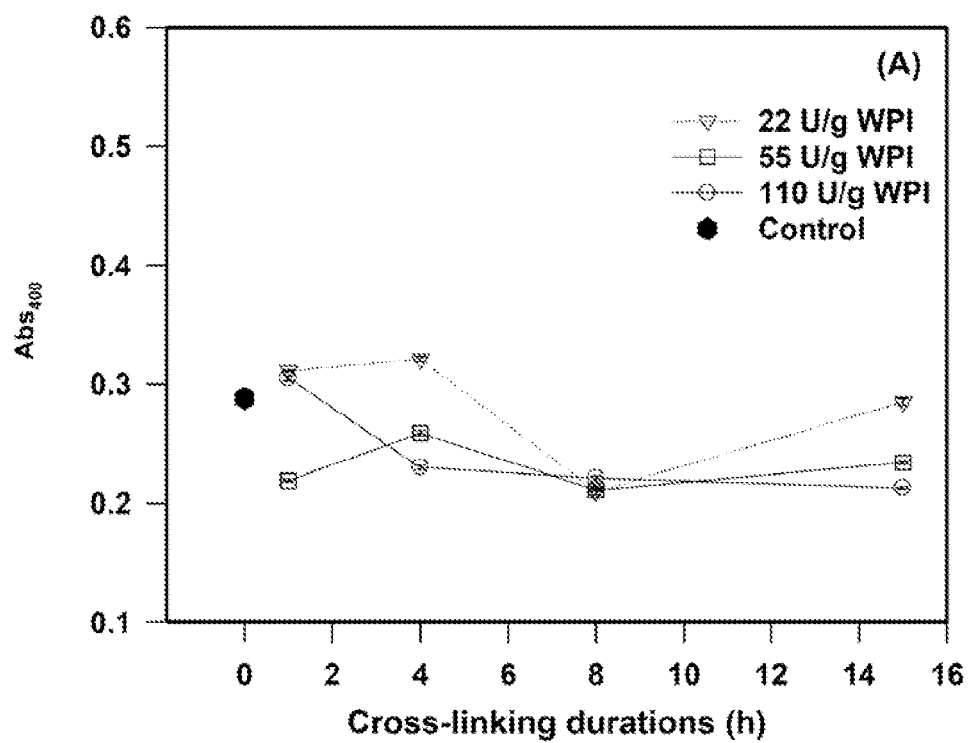
Figure 24B:
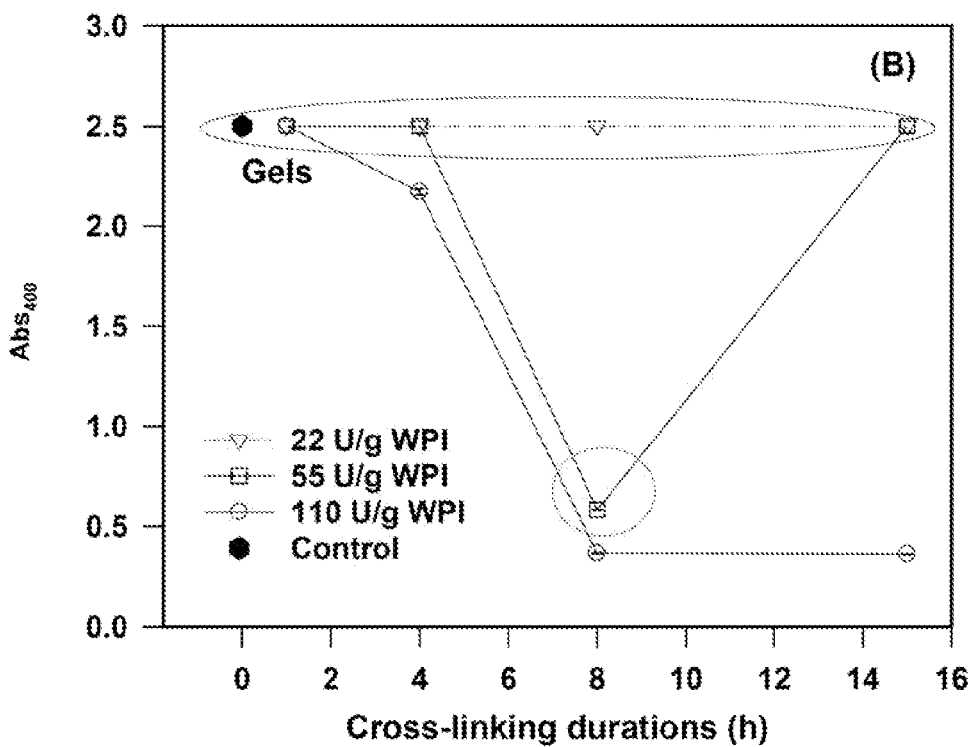
Figure 24C:
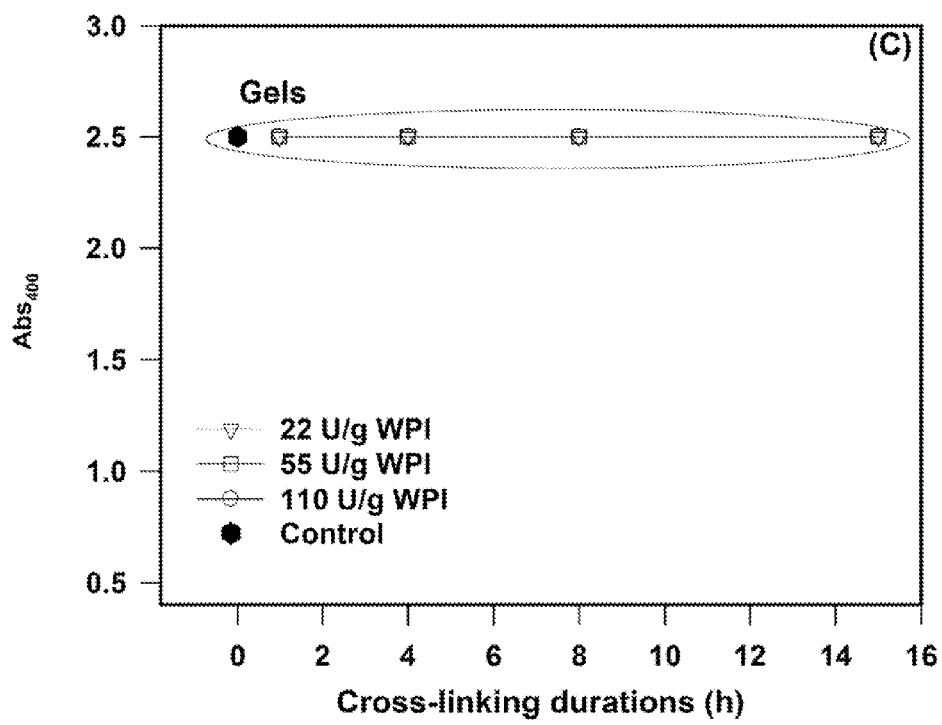

FIGS. 24A-24C. Absorbance of samples at 400 nm after heating at 138° C. for 5 min. 5% w/v WPI samples were adjusted to pH 7.5 and cross-linked by different concentrations of transglutaminase for 1-15 h before adjusting pH 7.0 and (A) 0, (B) 50, and (C) 100 mM NaCl for heat stability tests. Error bars are standard deviations from three replicates.

Figure 25A:
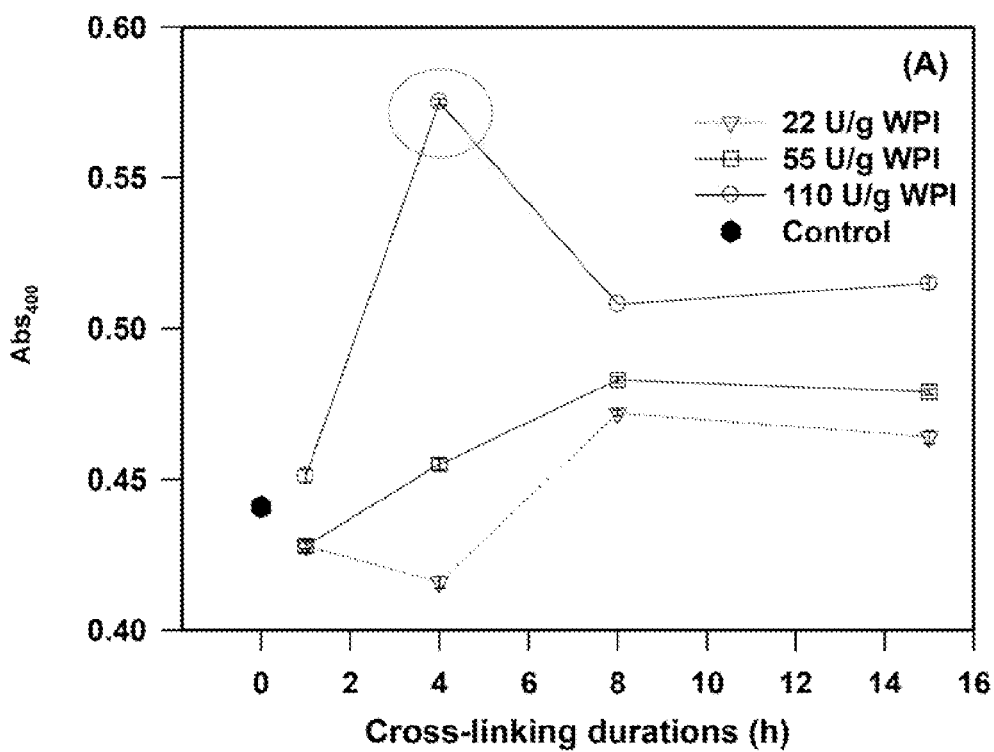
Figure 25B:
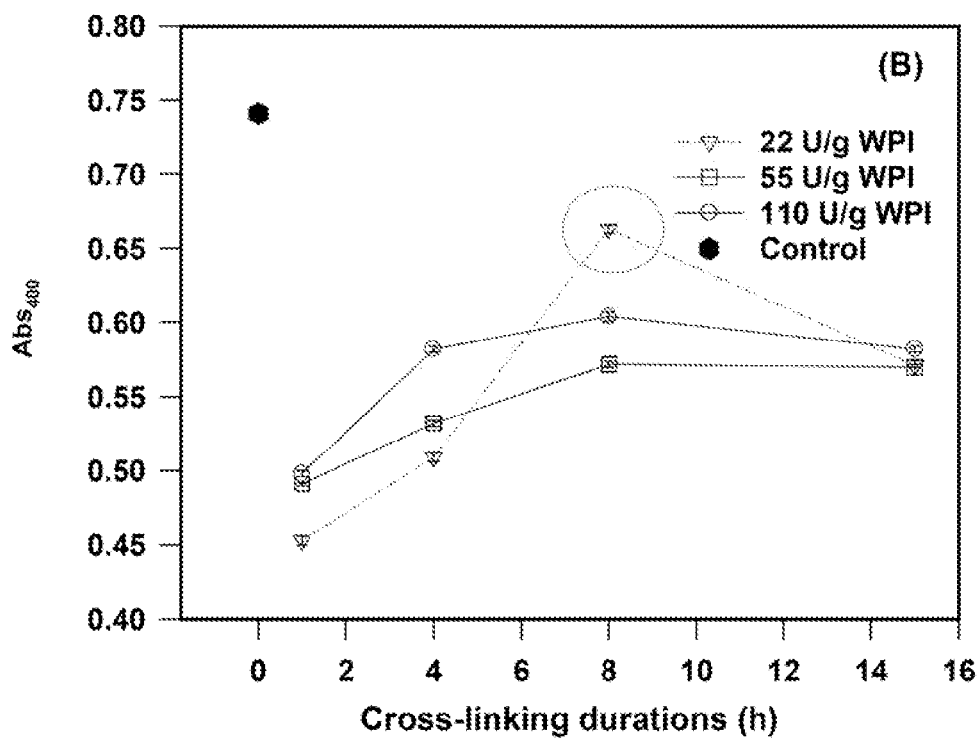
Figure 25C:
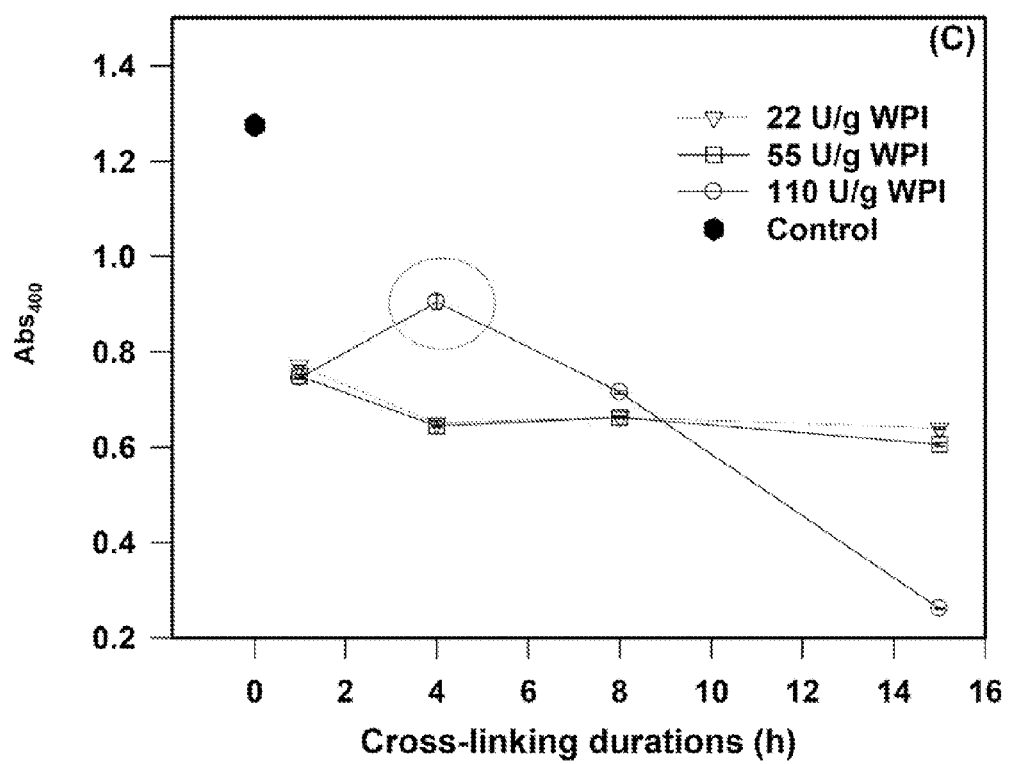

FIGS. 25A-25C. Absorbance of samples at 400 nm after heating at 138° C. for 1 min. 5% w/v WPI samples were adjusted to pH 7.5, preheated at 80° C. for 15 min, and then cross-linked by different concentrations of transglutaminase for 1-15 h before adjusting to pH 7.0 and (A) 0, (B) 50, and (C) 100 mM NaCl for heat stability tests. Error bars are standard deviations from three replicates.

Figure 26A:
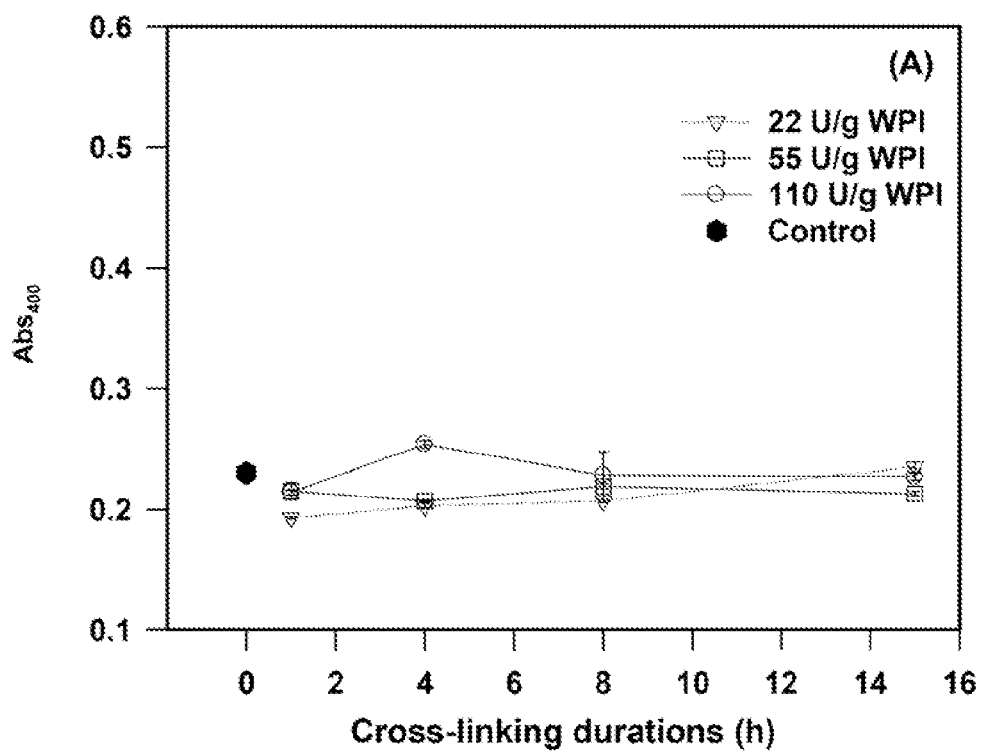
Figure 26B:
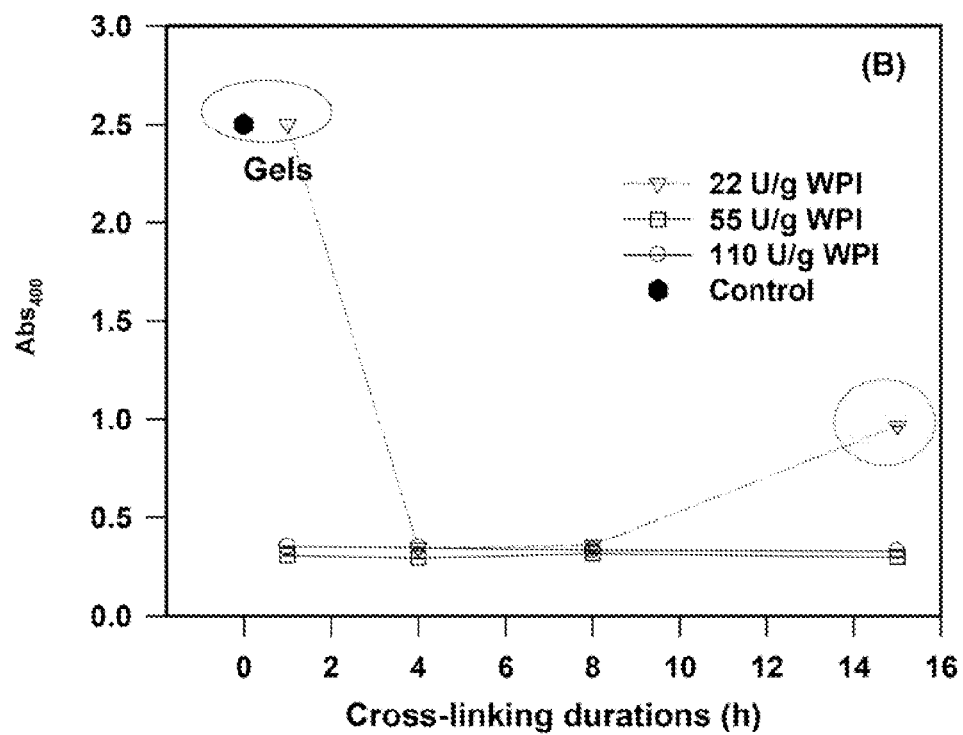
Figure 26C:
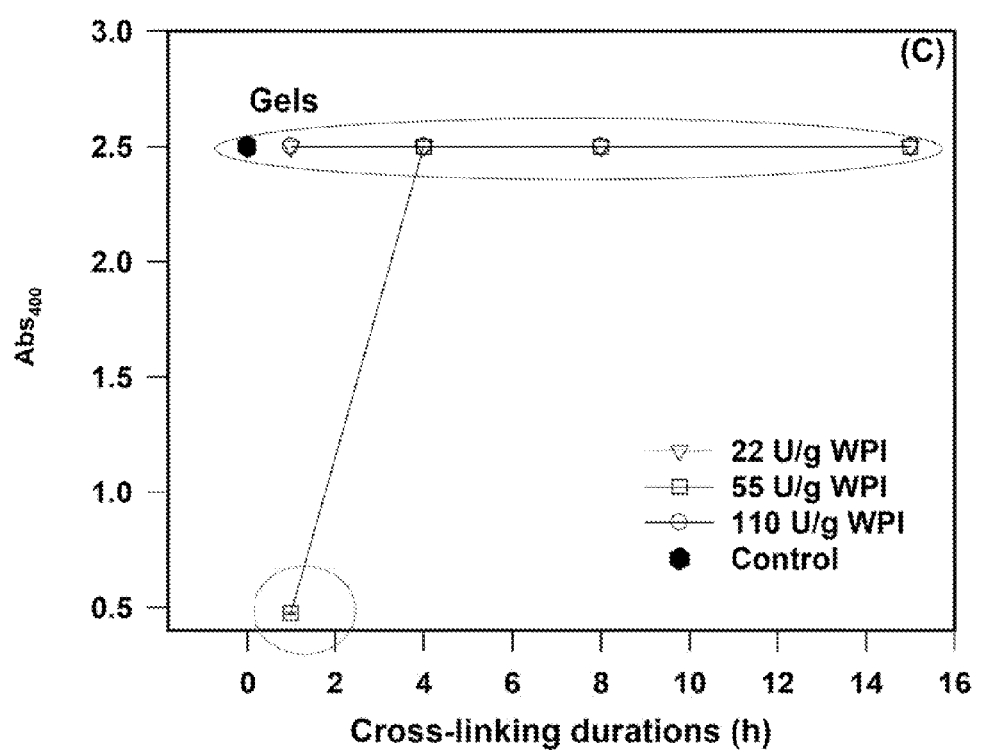

FIGS. 26A-26C. Absorbance of samples at 400 nm after heating at 138° C. for 5 min. 5% w/v WPI samples were adjusted to pH 7.5, preheated at 80° C. for 15 min, and then cross-linked by different concentrations of transglutaminase for 1-15 h before adjusting to pH 7.0 and (A) 0, (B) 50, and (C) 100 mM NaCl for heat stability tests. Error bars are standard deviations from three replicates.

Figure 27:
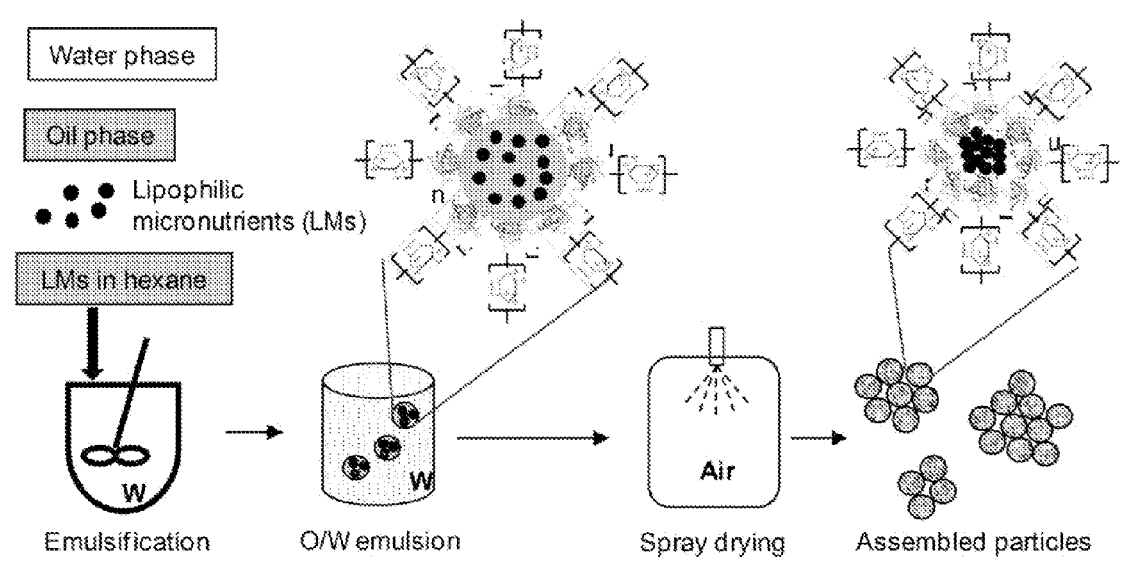

FIG. 27. Principle of emulsion-evaporation using spray drying.

Figure 28:
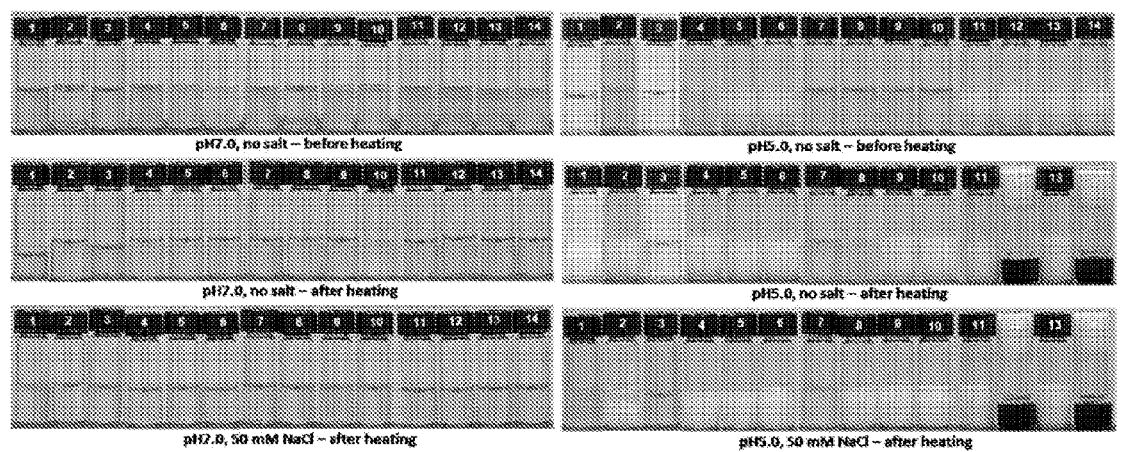

FIG. 28. Photographs of samples 1-14 in Table 1, hydrated at 5% w/v and adjusted to pH 5.0 and 7.0 and 0 and 50 mM NaCl, before and after heating at 85° C. for 15 min.

Figure 29:
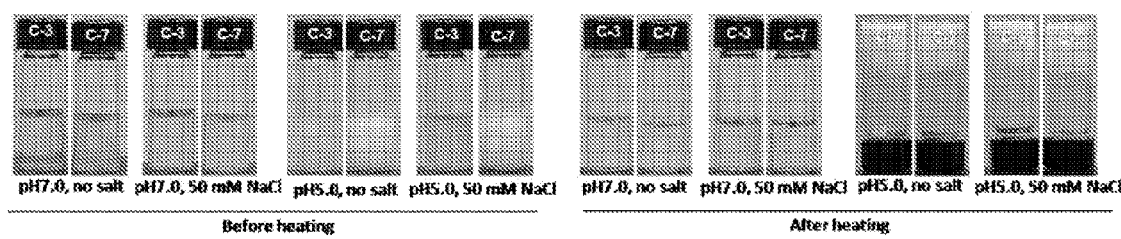

FIG. 29. Photographs of Samples C-3 and C-7 before and after heating at 85° C. for 15 min. Samples C-3 and C-7 were prepared as controls for Samples 3 and 7 in FIG. 2 by using WPI with an amount equivalent to one-third of conjugates.

Figure 30:
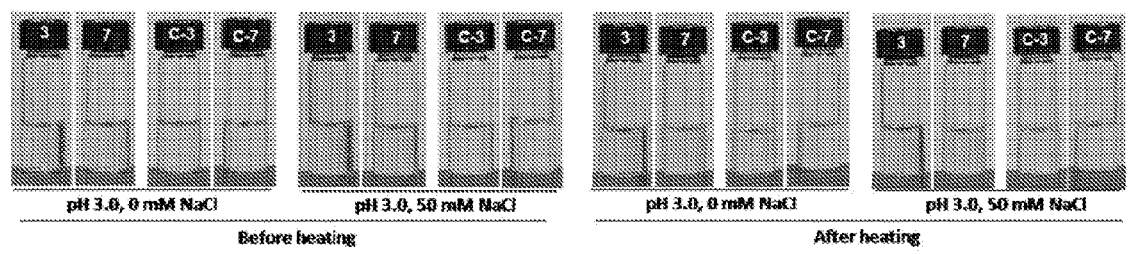

FIG. 30. Photographs of Samples 3 and 7 and their controls (Samples C-3 and C-7) before and after heating at 85° C. for 15 men. Samples C-3 and C-7 were prepared as controls for Samples 3 and 7 in FIG. 28 by using WPI with an amount equivalent to one-third of conjugates.

Figure 31:
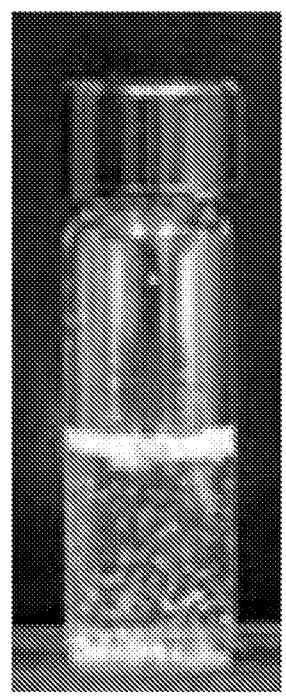

FIG. 31. Sample with 0.53% thymol in water.

Figure 32:
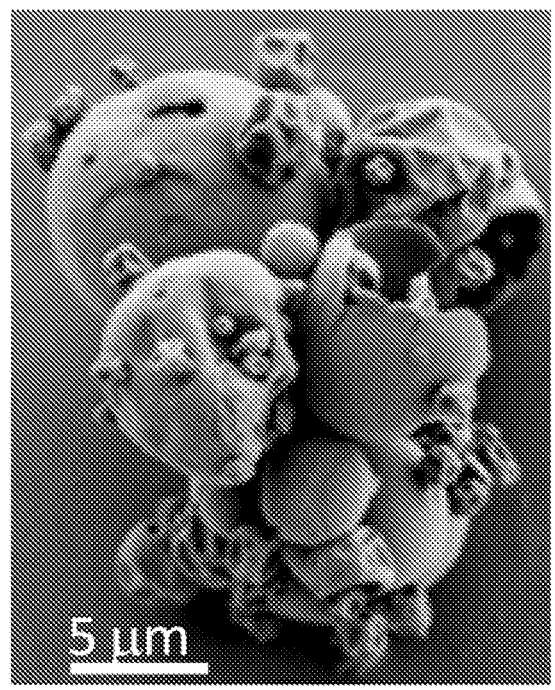

FIG. 32. Scanning electron micrograph (SEM) image of spray-dried powder of Sample 7.

Figure 33A:
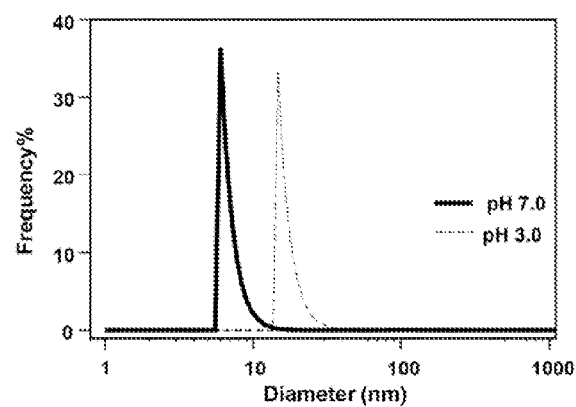
Figure 33B:
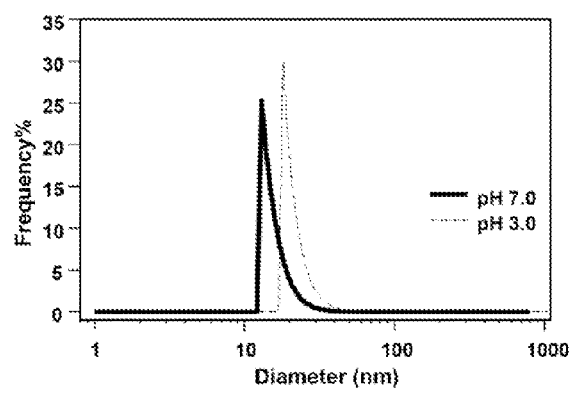

FIGS. 33A-33B. Particle size distributions of Sample 7 at pH 7.0 and 3.0 with 50 mM NaCl before (A) and after (B) heating at 80° C. for 15 min.

Figure 34A:
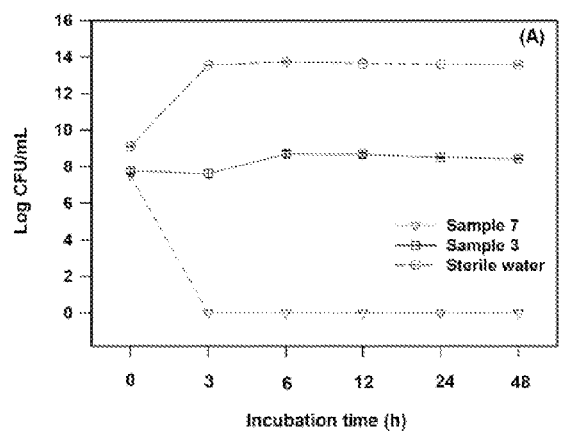
Figure 34B:
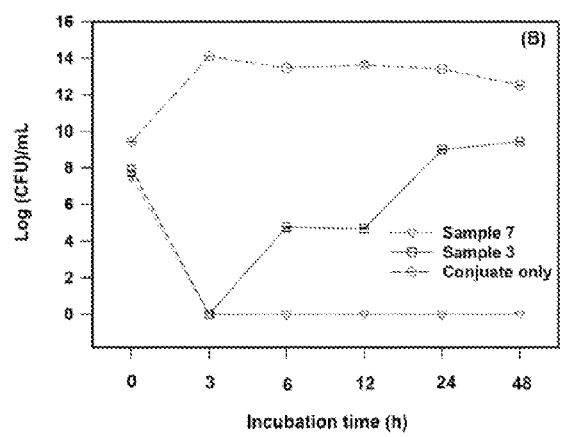

FIGS. 34A-34B. The antimicrobial function of 5% dispersions of Samples 3 and 7 against *E. coli* O157:H7. Comparison of the growth of *E. coli* O157:H7 strain 43894 (A) and 43889 (B) at 35° C. after mixing 2.5 mL culture, 12.5 mL of the Tryptic Soy Agar growth medium and 10 mL of stock solutions prepared with 5% w/v spray-dried powders of Samples 3 and 7 in Table 1. Positive controls are shown for sterile water (in A) and 5% w/v conjugate with no thymol (in B).

Figures 35A, 35B:
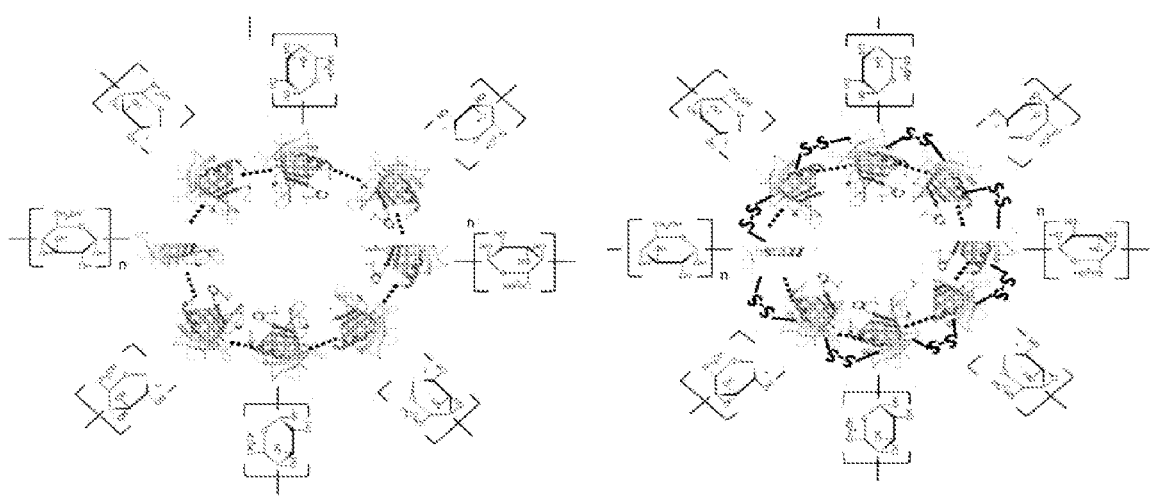

FIGS. 35A-35B. Schematic illustrations of possible structures of the CPCCs produced by the methods disclosed herein.

DETAILED DISCLOSURE OF THE INVENTION

As discussed above, the subject application provides methods of making protein-carbohydrate conjugates that may be crosslinked or uncrosslinked (see, for example, Examples 1-5). The methods include: combining proteins and sugars/carbohydrates comprising a carbohydrate (reducing sugar) in an aqueous solution (e.g., at a ratio of about 10:1 to about 1:10). The combined protein and sugar/carbohydrate composition is then heated to produce protein carbohydrate conjugates (PCC(s)). Where dry heat is used, the composition can be freeze- or spray dried to obtain a powdered product which can then be heated, for example, in an oven, for a period of about 0.5 to about 48 hours in order for the carbohydrate to be conjugated to the protein via a Maillard reaction (forming a protein-carbohydrate conjugate (PCC). In various aspects of the invention, the initial protein carbohydrate solution can be maintained at a pH from about 3.0 to about 9.0.

After recovery of the protein-carbohydrate conjugate, the PCC can be dissolved or suspended in an aqueous solution. To this solution, one or more enzyme capable of cross-linking the protein and/or the carbohydrate elements of the conjugate can be added to the solution to facilitate the crosslinking of one or both elements of the PCC. The methods may further include recovering of the PCC from the solutions in various ways, for example including isoelectric precipitation, ultrafiltration and/or chromatography, or simply drying to remove solvent. In certain aspects of the invention, aqueous solutions into which the powdered PCC has been dissolved/suspended are heated prior to enzymatic treatment with one or more enzyme capable of cross-linking the protein and/or the carbohydrate elements of the conjugate. The aqueous solutions may be heated at a temperature of between about 50° C. and about 150° C. for a period of about 5 to about 120 minutes, cooled and then treated with one or more enzyme capable of cross-linking the protein (or another means of crosslinking said proteins, e.g., linkers) and/or the carbohydrate elements of the conjugate. Alternatively, the aqueous solutions may be heated at a temperature of between about 50° C. and about 150° C. for a period of about 5 seconds to about 120 minutes (or more), cooled and then treated with one or more enzyme capable of cross-linking the protein (or another means of crosslinking said proteins, e.g., linkers) and/or the carbohydrate elements of the conjugate.

Thus, one aspect of the invention provides methods of making a protein-carbohydrate conjugate (PCC) comprising:

a) combining proteins and carbohydrates comprising a carbohydrate (reducing sugar) in an aqueous solution at a ratio (protein:carbohydrate) of about 10:1 to about 1:10 where any ratio between 10:1 and about 1:10 can form an upper or lower endpoint for a range of ratios;

b) freeze drying or spray drying said aqueous solution to form a powder;

c) forming a protein-carbohydrate conjugate (PCC(s));

d) recovering the PCC(s) and preheating the recovered PCC(s) at a temperature of between about 50° C. and about 150° C. for a period of about 5 to about 120 minutes;

e) treating the recovered PCC(s) with one or more enzymes that crosslink the protein and/or carbohydrate component of the PCC(s) to form crosslinked protein carbohydrate conjugates (CPCC(s)); and f) recovering the CPCC(s). In certain aspects of the invention, the CPCC(s) may be deglycated using methods known in the art before or after recovery.

A variety of proteins may be used in the methods disclosed herein. Useful proteins will preferably have one or more amino (e.g., lysine) residues to which the carbohydrate is conjugated. In some aspects of the invention, a variety of proteins with molecular weights in the range of about 11,000 Da to about 500,000 Da can be used to form the CPCCs disclosed herein. The proteins may include whey proteins (e.g. whey protein isolate, WPI), caseins (caseinates), soy proteins, collagen, gelatin, albumin, casein, transferrin, globulin, fibroin, fibrin, laminin, fibronectin, and vitronectin. The amounts of protein may vary, and in some examples the concentration of protein that is used for practicing the disclosed methods are typically in the range of about 1-30% (w/v), 5-20% (w/v) or about 10-17% (w/v). In one example, conjugates are formed in reactions that use starting aqueous solutions of about 10-17% (w/v) protein.

A variety of sugars (carbohydrates), preferably with one or more types of reducing terminal, may be used for practicing the present invention. Examples of sugars that can be used for practicing the present invention include: monosaccharides (e.g., glyceraldehyde; arabinose; ribose; xylose; galactose, glucose, mannose; fructose); disaccharides (e.g., lactose; maltose); polysaccharides (e.g., galactomannans; dextran; maltodextrin; chitosan; alginic acid; agar; carrageenan; dextran sulfate; konjac mannan; xyloglucan; starch; modified starches; pectins; dietary fiber, such as polydextrose, wheat dextrin, oat bran concentrate). In some examples, the polysaccharides useful for practicing the present invention may include aqueous solutions of about 1-40% (w/v) dextran or about 1-40% (w/v) maltodextrin.

The conjugation reactions may be carried out under controlled temperature conditions. For example, the conjugation reaction may be carried out using temperatures in the range of about 40° C. to about 120° C., about 70° C. to about 95° C. In various examples disclosed herein, the conjugation reaction may be carried out using a temperature of about 80-90° C. or about 85° C. Alternatively, sugars/carbohydrates can be conjugated to the proteins with chemical linkers as discussed below.

In some aspects of the invention, a crosslinked or a spacer can be provided on either the protein or the carbohydrate to facilitate attachment of the sugar/carbohydrate to the protein. Because the crosslinker is a smaller molecule, it helps the coupling reaction for the larger protein and carbohydrate molecules proceed more quickly by allowing better access to the large molecules, and thereby enhancing the reactivity. Additionally, the use of a crosslinker allows one to more effectively control the degree of crosslinking and the chemical structure of the resultant conjugate. Various procedures and chemistries are available for activating and attaching spacers to proteins and to carbohydrates, e.g., using CDAP, carbodiimides or NHS esters. Published PCT Patent Application No. WO/1997/041897, incorporated herein by reference, describes the use of vinylsulfones as the reactive group in a crosslinking agent. Instead of enzymatic crosslinking of the proteins in the CPCCs disclosed herein, crosslinkers can also be used to crosslink the proteins and/or sugars/carbohydrates.

Another aspect of the invention provides methods for stabilizing PCCs formed according to methods known in the art. In this aspect of the invention, PCCs are formed according to methods disclosed, for example, in U.S. Patent Application Publication 2006/0165990, U.S. Patent Application Publication 2006/0159805, WO/2006/090110, WO/2007/120500, WO/2009/117572, WO/2008/017962, or Akhtar et al., Food Hydrocolloids, 2007, 21:607-616, the disclosures of which are hereby incorporated by reference in their entirety. The PCCs formed according to these methods may then be formed into a composition comprising PCC(s) in an aqueous solution and preheated at a temperature of about 50° C. to about 150° C. The preheated PCC(s) can then be treated with one or more enzymes that crosslink the protein and/or the sugar/carbohydrate component of the PCC(s) to form crosslinked protein carbohydrate conjugates (CPCC(s)). The CPCCs can then be recovered or loaded with a substance as disclosed herein. In certain embodiments, the enzyme used to treat the preheated PCCs is transglutaminase and the proteins used to form the PCCs can be soy protein, whey protein, whey protein isolate, caseinate, casein and/or gelatin. Where recovery of the CPCCs is desired, the CPCCs are recovered by size exclusion, affinity or anion exchange chromatography, ultrafiltration, isoelectric precipitation or by drying. The composition comprising PCC(s) and an aqueous solution can be preheated to about 80° C. to 90° C. for about 15 minutes or to about 85° C. for about 15 minutes. In any method of making CPCCs, the preheated composition may be, optionally, cooled to room temperature (or lower) before adjusting to conditions functional for one or more enzymes that crosslink the protein and/or the sugar/carbohydrate component of the PCC(s) to form crosslinked protein carbohydrate conjugates (CPCC(s)).

Another aspect of the invention provides CPCCs produced according to the methods disclosed herein. The resulting purified CPCCs provided herein exhibit improved thermal stability and are also stable at variety of pH values, including the ability to form heat stable complexes at pH values of 7 and 3. For example CPCCs are heat stable (when treated at 138° C. for one minute in sterilization processes) and provide clear solutions at a pH of 7 in the presence of 50 mM NaCl or at a pH of about 3 at a protein concentration of 15% (w/v). Substrate loaded CPCCs comprising whey protein and maltodextrin are also stable at a pH of about 5 and 7 in the presence and absence of salt, which to the knowledge of the inventors, is the first system reported to be stable at a pH of about 5 for whey protein systems. Thus, one aspect of the invention provides CPCCs comprising whey protein conjugated to maltodextrin (which may be, optionally, deglycated in a subsequent step).

In various other aspects of the invention, the method further comprises loading CPCCs with a substance. In these aspects of the invention, volatile organic solvents can be used for loading lipophilic substances and forming emulsions comprising the CPCCs disclosed herein. These solvents include, and are not limited to: methanol, ethanol, isopropanol, acetone, pentane, cyclopentane, hexane, cyclohexane, benzene, chloroform, diethyl ether, dichloromethane, tetrahydrofuran, ethyl acetate and/or acetonitrile. In this aspect of the invention, a substance of interest is dissolved in an appropriate solvent, for example, a lipophilic compound(s) in a volatile organic solvent. One then emulsifies the organic solvent into an aqueous phase with dissolved CPCCs and spray drying the emulsion allows one to recover CPCCs loaded with a substance of interest. The process can be similarly applied to substances of interest that are hydrophilic and can be dissolved in an aqueous buffer.

Further, CPCCs can be loaded with a variety of substances. For example, the CPCCs can be loaded with a substance that is a nutritional supplement, a flavoring substance, a polyunsaturated fatty acid like an omega-3 fatty acid, a vitamin, a mineral, a carbohydrate, a steroid, a trace element, and/or a protein (including mixtures and combinations of these substances. Other examples of substances that can be loaded into CPCCs include microbial oils, algal oils, fungal oils, plant oils, lipophilic pharmaceuticals, flavorants and/or essential oils. Other examples of substances that can be loaded into CPCCs include: moisturizers, skin-whitening agents, hair restoration agents, hormone drugs, antiaging agents, an anticancer agent, antiallergic agents, antithrombotic agents, immunosuppressive agents, therapeutic agents for skin diseases, antifungal agents and anti-inflammatory agents. Yet other substances include: lipophilic anti-microbials, nutrients, nutraceuticals, flavorants and colorants. Food grade antimicrobials include lipophilic antimicrobials extracted from natural resources such as various berries (cranberries, blueberries, etc.) and plant essential oils such as carvacrol (5-Isopropyl-2-methylphenol), eugenol (2-Methoxy-4-(2-propenyl)phenol), linalool ((±)-3,7-Dimethyl-1,6-octadien-3-ol), and thymol (2-Isopropyl-5-methylphenol). Lipophilic nutrients include fat-soluble vitamins, while nutraceuticals include lycopene, polyunsaturated fatty acids, etc.

Specific examples of moisturizing agents used in the present invention include, but are not limited to, hyaluronic acid, ceramide, lipidure, isoflavone, amino acids, collagen, mucopolysaccharides, fucoidan, lactoferrin, sorbitol, chitin, chitosan, malic acid, glucuronic acid, placenta extract, seaweed extract, moutan bark extract, sweet hydrangea leaf extract, hypericum extract, coleus extract, *Euonymus japonica* extract, safflower extract, *Rosa rugosa* flower extract, *Polyporus sclerotium* extract, hawthorn extract, rosemary extract, duku extract, chamomile extract, lamium album extract, *Litchi chinensis* extract, *Achillea millefolium* extract, aloe extract, marronnier extract, *Thujopsis dolabrata* extract, Fucus extract, Osmoin extract, oat extract, Tuberosa polysaccharide, *Cordyceps sinensis* extract, barley extract, orange extract, Rehmannia root extract, zanthoxylum fruit extract, and coix seed extract.

Specific examples of skin-whitening agents used in the present invention include, but are not limited to, vitamin. C and a derivative thereof, arbutin, hydroquinone, kojic acid, Lucinol, ellagic acid, tranexamic acid, and glutathione.

Specific examples of hair restoration agents that can be used in the present invention include, but are not limited to, adenosine, cepharanthin, glycyrrhetic acid or a derivative thereof, glycyrrhizin acid or a derivative thereof, isopropyl methyl phenol, pantothenic acid, panthenol, t-flavanone, tocopherols or a derivative thereof, hinokitiol, pentadecanoic acid or a derivative thereof, licorice extract, Lepisorus extract, sophora root extract, swertia herb extract, capsicum extract, *Ampelopsis cantoniensis* var. *grossedentata* extract, carrot extract, Taraxacum extract, tree peony extract, orange extract, blood circulation promoters (e.g., nicotinic acid, benzyl nicotinate, tocopherol nicotinate, nicotinic acid β-butoxy ester, minoxidil or an analog thereof, swertia herb extract, γ-oxazole, alkoxycarbonylpyridine N-oxide, carpronium chloride, and acetylcholine or a derivative thereof).

Specific examples of hormone drugs that can be used in the present invention include, but are not limited to, estradiol, ethinyl estradiol, estron, cortisone, hydrocortisone, prednisone, and prednisolone. Anti-aging agents used in the present invention include, but are not limited to, retinoic acid, retinol, vitamin C and a derivative thereof, kinetin, β-carotene, astaxanthin, and tretinoin.

Specific examples of vitamins that are used in the present invention include, but are not limited to, vitamin A and a derivative thereof, retinoic acid, vitamin B family (e.g., vitamin B1, vitamin B2, vitamin B6, vitamin B12, and folic acid), vitamin C and a derivative thereof, vitamin D, vitamin E, vitamin F, pantothenic acid, and vitamin H.

Specific examples of antioxidants used in the present invention include, but are not limited to, a vitamin C and a derivative thereof, vitamin E, kinetin, α-lipoic acid, coenzyme Q10, polyphenol, SOD and phytic acid.

Specific examples of anticancer agents used in the present invention include, but are not limited to: fluorinated pyrimidine antimetabolites (for example, 5-fluorouracil (5-FU), tegafur, doxifluridine, and capecitabine); antibiotics (for example, mitomycin (MMC) and adriacin (DXR)); purine antimetabolites (for example, folic acid antagonists such as methotrexate and mercaptopurine); active metabolites of vitamin A (for example, antimetabolites such as hydroxy carbamide, tretinoin, and tamibarotene); molecular targeting agents (for example, Herceptin and imatinib mesylate); platinum agents (for example, Briplatin or Randa (CDDP), Paraplatin (CBDC), Elplat (Oxa), and Akupura); plant alkaloids (for example, Topotecin or Campto (CPT), taxol (PTX), Taxotere (DTX), and Etoposide); alkylating agents (for example, busulphan, cyclophosphamide, and ifomide); anti-androgenic agents (for example, bicalutamide and flutamide); estrogenic agents (for example, fosfestrol, chlormadinone acetate, and estramustine phosphate); LH-RH agents (for example, Leuplin and Zoladex); antiestrogenic agents (for example, tamoxifen citrate and toremifene citrate); aromatase inhibitors (for example, fadrozole hydrochloride, anastrozole, and exemestane); progestational agents (for example, medroxyprogesterone acetate); and BCG.

Specific examples of antiallergic agents used in the present invention include, but are not limited to: disodium cromoglycate and tranilast; histamine H1 antagonists, such as ketotifen fumarate and azelastine hydrochloride; thromboxane inhibitors, such as ozagrel hydrochloride; leukotriene antagonists, such as pranlukast; and suplatast tosylate.

Specific examples of antithrombotic agents that are used in the present invention include, but are not limited to, aspirin, ticlopidine hydrochloride, cilostazol, and warfarin potassium.

Specific examples of immunosuppressive agents that are used in the present invention include, but are not limited to, rapamycin, tacrolimus, ciclosporin, prednisolone, methylprednisolone, mycophenolate mofetil, azathioprine, and mizoribine.

Specific examples of therapeutic agents for skin diseases that are used in the present invention include, but are not limited to: therapeutic agents for atopic dermatitis (e.g., steroids, such as hydrocortisone butyrate, clobetasone butyrate, alclometasone propionate, clobetasol propionate, betamethasone dipropionate, and difluprednate, immunosuppressive agents such as tacrolimus, nonsteroids, such as bufexamac, ufenamate, ibuprofen piconol, and bendazac, zinc oxide, azulene, diphenhydramine, crotamiton, and moistening agents); acne medications, such as sulfur, salicylic acid, resorcin, thioxolone, selenium sulfide, nadifloxacin, gentamicin sulfate, tetracycline hydrochloride, clindamycin phosphate, and retinoic acid; and therapeutic agents for eczema.

Specific examples of antifungal agents that are used in the present invention include, but are not limited to, clotrimazole, bifonazole, miconazole nitrate, econazole nitrate, sulconazole nitrate, neticonazole hydrochloride, cloconazole hydrochloride, lanoconazole, ketoconazole, luliconazole, amorolfine hydrochloride, terbinafine hydrochloride, and tolnaftate.

Specific examples of an antiinflammatory agent that can be used in the present invention include, but are not limited to, a compound which is selected from azulene, allantoin, lysozyme chloride, guaiazulene, diphenhydramine hydrochloride, hydrocortisone acetate, prednisolone, glycyrrhizinic acid, glycyrrhetinic acid, glutathione, saponin, methyl salicylate, mefenamic acid, phenylbutazone, indometacin, ibuprofen and ketoprofen, and its derivative and its salt.

Another aspect of the invention provides for compositions comprising a carrier and a CPCC as disclosed herein. In various embodiments, the carrier can be an aqueous solution and/or a clear liquid. Various other embodiments provide for the composition to have a pH that ranges from about 3 to about 8. Yet other embodiments provide for the composition to have a pH of about 3, about 5 or about 7. In any of the aforementioned embodiments, the composition can also have an ionic strength that is substantially similar to a solution comprising (or consisting of) 50 mM NaCl, 75 mM NaCl, 100 mM NaCl or a solution having an ionic strength substantially equal to a solution comprising (or consisting of) between about 1 mM and about 100 mM NaCl.

Additionally, the following non-limiting embodiments are provided:

1. A method of making a protein-carbohydrate conjugate (PCC) comprising:

a) combining proteins and a carbohydrates (reducing sugars) in an aqueous solution;

b) spray drying or freeze drying said aqueous solution to form a powdered composition comprising said proteins and said carbohydrate;

c) forming a bond between said carbohydrate and said protein to form a protein-carbohydrate conjugate (PCC);

d) optionally, forming a composition comprising PCC(s) in an aqueous solution and preheating said composition at a temperature of about 50° C. to about 150° C.;

e) optionally, treating the preheated PCC(s) with one or more enzymes that crosslink the protein and/or the carbohydrate component of the PCC(s) to form crosslinked protein carbohydrate conjugates (CPCC(s)); and f) recovering the PPCs or CPCC(s) or loading said PCCs or CPCCs with a substance.

2. The method according to embodiment 1, wherein said protein is soy protein, whey protein, whey protein isolate, caseinate, casein and/or gelatin.

3. The method according to embodiment 1, wherein said carbohydrate is glyceraldehyde; arabinose; ribose; xylose; galactose, glucose, mannose; fructose; lactose; maltose; galactomannan; dextran; maltodextrin; chitosan; alginic acid; agar; carrageenan; dextran sulfate; konjac mannan; xyloglucan; starch; modified starch; pectin; polydextrose, wheat dextrin or oat bran concentrate.

4. The method according to embodiment 1, wherein step b) comprises spray drying said aqueous solution and recovering the powder that results from said spray drying.

5. The method according to embodiment 1 or embodiment 4, wherein step b) comprises freeze drying said aqueous solution and recovering the powder that results from said spray drying.

6. The method according to embodiment 1 or 4, where in said bond is formed via a Maillard reaction between said carbohydrate and said protein.

7. The method according to embodiment 1 or 4, wherein said bond is formed between said carbohydrate and said protein by a linker molecule.

8. The method according to embodiment 1 or 4, wherein said composition comprising the PCC(s) and an aqueous solution is heated at a temperature of about 50-150° C.

9. The method according to embodiment 1 or 4, wherein said CPCCs are crosslinked with a transglutaminase or another enzyme that crosslinks proteins.

10. The method according to embodiment 1 or 4, wherein said CPCCs are crosslinked with an enzyme that forms bonds between carbohydrates.

11. The method according to embodiment 1 or 4, wherein said CPCCs are crosslinked with chemical linkers that crosslink said proteins.

12. The method according to embodiment 1 or 4, wherein said the ratio of protein to carbohydrate about 10:1 to about 1:10.

13. The method according to embodiment any preceding embodiment, wherein said CPCCs are recovered by size exclusion, affinity or anion exchange chromatography, ultrafiltration, isoelectric precipitation or by drying.

14. The method according to embodiment 1-13, further comprising loading said PCCs or CPCCs with a substance.

15. The method according to embodiment 14, wherein said substance is/are a nutritional supplement, a flavoring substance, a polyunsaturated fatty acid, a vitamin, a mineral, a carbohydrate, a steroid, a trace element, a protein, microbial oils, algal oils, fungal oils, plant oils, lipophilic pharmaceuticals, essential oils, moisturizers, skin-whitening agents, hair restoration agents, hormone drugs, antiaging agents, an anticancer agent, antiallergic agents, antithrombotic agents, immunosuppressive agents, therapeutic agents for skin diseases, antifungal agents anti-inflammatory agents, lipophilic anti-microbials, nutraceuticals or colorants.

16. The method according to embodiment 1-16, wherein the protein:carbohydrate ratio is 10:1, 9:1, 8:1, 7:1, 6:1, 5:1, 4:1, 3:1, 2:1, 1:1, 1:2, 1:3, 1:4, 1:5, 1:6, 1:7, 1:8, 1:9 or 1:10.

17. The method according to embodiment 1-16, wherein protein:carbohydrate ratio is 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10 or a range of ratios between 10:1 and 1:10.

18. The method according to embodiment 1-17, wherein said protein is whey protein and said carbohydrate is maltodextrin.

19. The method according to embodiment 18, wherein the ratio of protein:carbohydrate is about 10:1, 9:1, 8:1, 7:1, 6:1, 5:1, 4:1, 3:1, 2:1, 1:1, 1:2, 1:3, 1:4 or 1:5.

20. The method according to embodiment 1 or 18-19, wherein said composition comprising PCC(s) and an aqueous solution is preheated to about 80° C. to 90° C. for about 15 minutes.

21. The method according to embodiment 20, wherein said composition comprising PCC(s) and an aqueous solution is preheated to about 85° C. for about 15 minutes.

22. A crosslinked protein-carbohydrate conjugate (CPCC) or protein-carbohydrate conjugate (PCC) produced by the method of any one of embodiments 1-21 or any one of embodiments 33-42.

23. The CPCC or PCC according to embodiment 22, wherein said PCCs or CPCC is loaded with a substance.

24. The PCC or CPCC according to embodiment 23, wherein said substance is/are a nutritional supplement, a flavoring substance, a polyunsaturated fatty acid, a vitamin, a mineral, a carbohydrate, a steroid, a trace element, a protein, microbial oils, algal oils, fungal oils, plant oils, lipophilic pharmaceuticals, essential oils, moisturizers, skin-whitening agents, hair restoration agents, hormone drugs, antiaging agents, an anticancer agent, antiallergic agents, antithrombotic agents, immunosuppressive agents, therapeutic agents for skin diseases, antifungal agents anti-inflammatory agents, lipophilic anti-microbials, nutraceuticals or colorants.

25. A composition comprising a CPCC or PCC according to embodiment 22 and a carrier.

26. The composition according to embodiment 25, wherein said carrier is an aqueous solution.

27. The composition according to embodiments 25-26, wherein said composition is a clear liquid.

28. The composition according to embodiment 27, wherein said composition has a pH that ranges from about 3 to about 8.

29. The composition according to embodiment 28, wherein said composition has a pH of about 3.

30. The composition according to embodiment 28, wherein said composition has a pH of about 5.

31. The composition according to embodiment 28, wherein said composition has a pH of about 7.

32. The composition according to embodiments 25-29, wherein said composition contains has an ionic strength substantially equal to a solution comprising 50 mM NaCl, 75 mM NaCl, 100 mM NaCl or a solution having an ionic strength substantially equal to a solution comprising between about 0 mM and about 100 mM NaCl.

33. A method of stabilizing protein-carbohydrate conjugates comprising:
 a) forming a protein-carbohydrate conjugate (PCC);
 b) optionally forming a composition comprising PCC(s) in an aqueous solution and preheating said composition at a temperature of about 50° C. to about 150° C.; and
 c) optionally treating the preheated PCC(s) with one or more enzymes that crosslink the protein and/or the carbohydrate component of the PCC(s) to form crosslinked protein carbohydrate conjugates (CPCC(s)).

34. The method according to embodiment 31, further comprising recovering the CPCC(s) or loading said PCCs or CPCCs with a substance.

35. The method according to embodiment 31-32, wherein said enzyme is a transglutaminase.

36. The method according to embodiment 31, wherein said protein is soy protein, whey protein, whey protein isolate, caseinate, casein and/or gelatin.

37. The method according to embodiment any preceding embodiment, wherein said CPCCs are recovered by size exclusion, affinity or anion exchange chromatography, ultrafiltration, isoelectric precipitation or by drying.

38. The method according to embodiment 33-37, further comprising loading said PCCs or CPCCs with a substance.

39. The method according to embodiment 38, wherein said substance is/are a nutritional supplement, a flavoring substance, a polyunsaturated fatty acid, a vitamin, a mineral, a carbohydrate, a steroid, a trace element, a protein, microbial oils, algal oils, fungal oils, plant oils, lipophilic pharmaceuticals, essential oils, moisturizers, skin-whitening agents, hair restoration agents, hormone drugs, antiaging agents, an anticancer agent, antiallergic agents, antithrombotic agents, immunosuppressive agents, therapeutic agents for skin diseases, antifungal agents anti-inflammatory agents, lipophilic anti-microbials, nutraceuticals or colorants.

40. The method according to embodiment 33, wherein said composition comprising PCC(s) and an aqueous solution is preheated to about 80° C. to 90° C. for about 15 minutes.

41. The method according to embodiment 20, wherein said composition comprising PCC(s) and an aqueous solution is preheated to about 85° C. for about 15 minutes.

42. The method according to embodiment 1-21 or 33-41, wherein said preheated composition is optionally cooled to room temperature or lower prior to treatment with one or more enzymes that crosslink the protein and/or the carbohydrate component of the PCC(s) to form crosslinked protein carbohydrate conjugates (CPCC(s)).

43. The method according to embodiment 14 or 38, wherein said PCCs or CPCCs are loaded with a lipophilic substance and loading of said PCCs or CPCCs comprises forming an emulsion comprising PCCs or CPCCs and said lipophilic substance and spray drying PCCs or CPCCs loaded with said lipophilic substance.

44. A method of making a heat-stable protein conjugate comprising preheating a solution comprising about 5% to about 20% protein (w/v) to a temperature of about 50° C. to about 150° C., cooling said solution and adding composition comprising one or more enzyme capable of cross-linking amino groups within proteins present in said cooled solution to form a combined solution.

45. The method according to embodiment 44, wherein said protein is soy protein, whey protein, whey protein isolate, caseinate, casein and/or gelatin.

46. The method according to embodiment 44 or 45, further comprising adjusting the pH of said combined solution is acidified and wherein said combined solution does not form a gel.

47. A composition comprising a crosslinked protein carbohydrate conjugate (CPPC), said composition comprising said CPPC exhibiting improved thermal stability and forming a clear solution at a pH of about 7 or about 3.

48. The composition according to embodiment 47, wherein said composition is heat stable when treated at 138° C. for at least one minute.

49. The composition according to embodiment 47, wherein said composition is a clear solution at a pH of 7 in the presence of 50 mM NaCl or at a pH of about 3 at a protein concentration of 15% (w/v).

50. A method of making a protein-carbohydrate conjugate (PCC) comprising:
a) combining proteins and a carbohydrate in an aqueous solution and said aqueous solution comprises protein in an amount of about 5% to about 20% (w/v);
b) spray drying or freeze drying said aqueous solution to form a powdered composition comprising said proteins and said carbohydrate; and
c) forming a bond between said carbohydrate and said protein to form a protein-carbohydrate conjugate (PCC).

51. The method according to embodiments 50, wherein said aqueous solution comprises between 0 mM and about 100 mM sodium chloride.

52. The method according to embodiment 50 or 51, wherein said aqueous solution has a pH of about 7.0.

53. The method according to embodiment 50, 51 or 52, wherein said protein is soy protein, whey protein, whey protein isolate, caseinate, casein and/or gelatin.

54. The method according to embodiments 50-53, wherein said carbohydrate is glyceraldehyde; arabinose; ribose; xylose; galactose, glucose, mannose; fructose; lactose; maltose; galactomannan; dextran; maltodextrin; chitosan; alginic acid; agar; carrageenan; dextran sulfate; konjac mannan; xyloglucan; starch; modified starch; pectin; polydextrose, wheat dextrin or oat bran concentrate.

55. The method according to embodiments 50-54, where in said bond is formed via a Maillard reaction between said carbohydrate and said protein.

56. The method according to embodiment 50-54, wherein said bond is formed between said sugar and said protein by a linker molecule.

57. The method according to embodiment 50-54, wherein the proteins are whey proteins and the carbohydrate is maltodextrin.

58. The method according to embodiment 44-46 or 50-57, wherein said PCCs or CPCCs are loaded with a lipophilic substance and loading of said PCCs or CPCCs comprises forming an emulsion comprising PCCs or CPCCs and said lipophilic substance and spray drying PCCs or CPCCs loaded with said lipophilic substance.

59. The method according to embodiment 44-46 or 50-57, further comprising loading said PCCs or CPCCs with a substance.

60. The method according to embodiment 59, wherein said substance is/are a nutritional supplement, a flavoring substance, a polyunsaturated fatty acid, a vitamin, a mineral, a carbohydrate, a steroid, a trace element, a protein, microbial oils, algal oils, fungal oils, plant oils, lipophilic pharmaceuticals, essential oils, moisturizers, skin-whitening agents, hair restoration agents, hormone drugs, antiaging agents, an anticancer agent, antiallergic agents, antithrombotic agents, immunosuppressive agents, therapeutic agents for skin diseases, antifungal agents anti-inflammatory agents, lipophilic anti-microbials, nutraceuticals or colorants.

61. The method according to embodiment 40-44 or 50-60, wherein said the ratio of protein to carbohydrate about 10:1 to about 1:10.

62. The method according to embodiment 61, wherein the protein:carbohydrate ratio is 10:1, 9:1, 8:1, 7:1, 6:1, 5:1, 4:1, 3:1, 2:1, 1:1, 1:2, 1:3, 1:4, 1:5, 1:6, 1:7, 1:8, 1:9 or 1:10.

Example 1

Materials and Methods

Materials

WPI sample (product 9400) was from Hilmar Cheese Company (Hilmar, Calif.). Maltodextrin M180, with a dextrose equivalence of 16.5-19.5, was a product of Grain Processing Company (Muscatine, Iowa). TGase (product Activa TG-TI) was supplied by Ajinomoto Food Ingredients LLC (Chicago, Ill.). The TGase sample had a specific activity of 1,100 U/g powder, measured based on a Sigma Method (for product T5398). One unit is defined as the formation rate of 1 μmol hydroxamate/min from substrates of N-carbobenzoxyglutaminyl-glycine and hydroxylamine at pH 6.0 and 37° C. Other chemicals were purchased from Fisher Scientific (Pittsburgh, Pa.).

Conjugation

Conjugation by the Maillard reaction was achieved using a literature dry method (Akhtar et al., 2007) with a slight modification. Briefly, WPI and maltodextrin were dissolved at a ratio of 1:2 in deionized water to enable good mixing of the two moieties. The solution was then spray dried at an inlet temperature of 160° C. (model B-290 Mini Spray Dryer, BÜCHI Labortechnik AG, Postfach, Switzerland) to obtain a powdered product that was incubated in an oven (model 1300M, Precision Scientific, Chicago, Ill.) at 90° C. for 2 h for the Maillard reaction. The final product was stored at −20° C.

Sample Preparations

Because protein is the cause of aggregation during heating, all solutions were constituted to have 5% w/v of WPI. Specifically, three groups of solutions were prepared in a 50 mM sodium phosphate buffer: 15% w/v conjugates, 5% w/v WPI, and a mixture of 5% w/v WPI and 10% w/v maltodextrin (WPI+MD). The solutions were then treated by the following methods before heat stability tests.

Enzymatic Cross-Linking.

Cross-linking of (conjugated or non-conjugated) protein in the above solutions was performed at two TGase levels: 22 or 55 U/g WPI. The solution was adjusted to pH 7.5 and subsequently incubated in a water bath at 50° C. for 4 h.

Preheating.

To compare to enzymatic treatments, the solutions were adjusted to pH 7.5 for preheating at 80° C. for 15 min. After heating, the solution was cooled in a room-temperature water bath immediately.

Sequential Steps of Preheating and Enzymatic Cross-Linking.

In this group of treatments, the solutions were preheated as above, cooled to room temperature, and added with 22 or 55 U TGase per gram WPI. The solution was readjusted to pH 117.5 for cross-linking at 50° C. for 4 h.

Heat Stability Tests

The above treated samples, after cooling in a room-temperature water bath, were adjusted to pH 7.0, 5.0, and 3.0 using 1 N HCl and 0, 50, and 100 mM NaCl. Two mL of solution was placed in a 4 mL vial for heating in a 80° C. water bath for 15 min. After heating, the vials were cooled in a room-temperature water bath immediately. Samples were then tested for absorbance at 420 ($Abs_{420}$) and 600 ($Abs_{600}$) nm using a UV/vis spectrophotometer (BioMate 5, Thermo Electron Corporation, Woburn, Mass.). Untreated samples were also prepared to the same WPI concentration and adjusted similarly to corresponding pH and salt conditions. Two replicates were tested for each sample.

Results and Discussion

Samples without Pretreatments

Before heating, samples were all clear at pH 3.0 and 7.0. At pH 5.0, samples with unconjugated WPI were turbid (photographs not shown), due to the aggregation of whey proteins near the isoelectric point, but the conjugate samples were clear, as reported in the literature (Akhtar et al., 2007).

Figure 1:
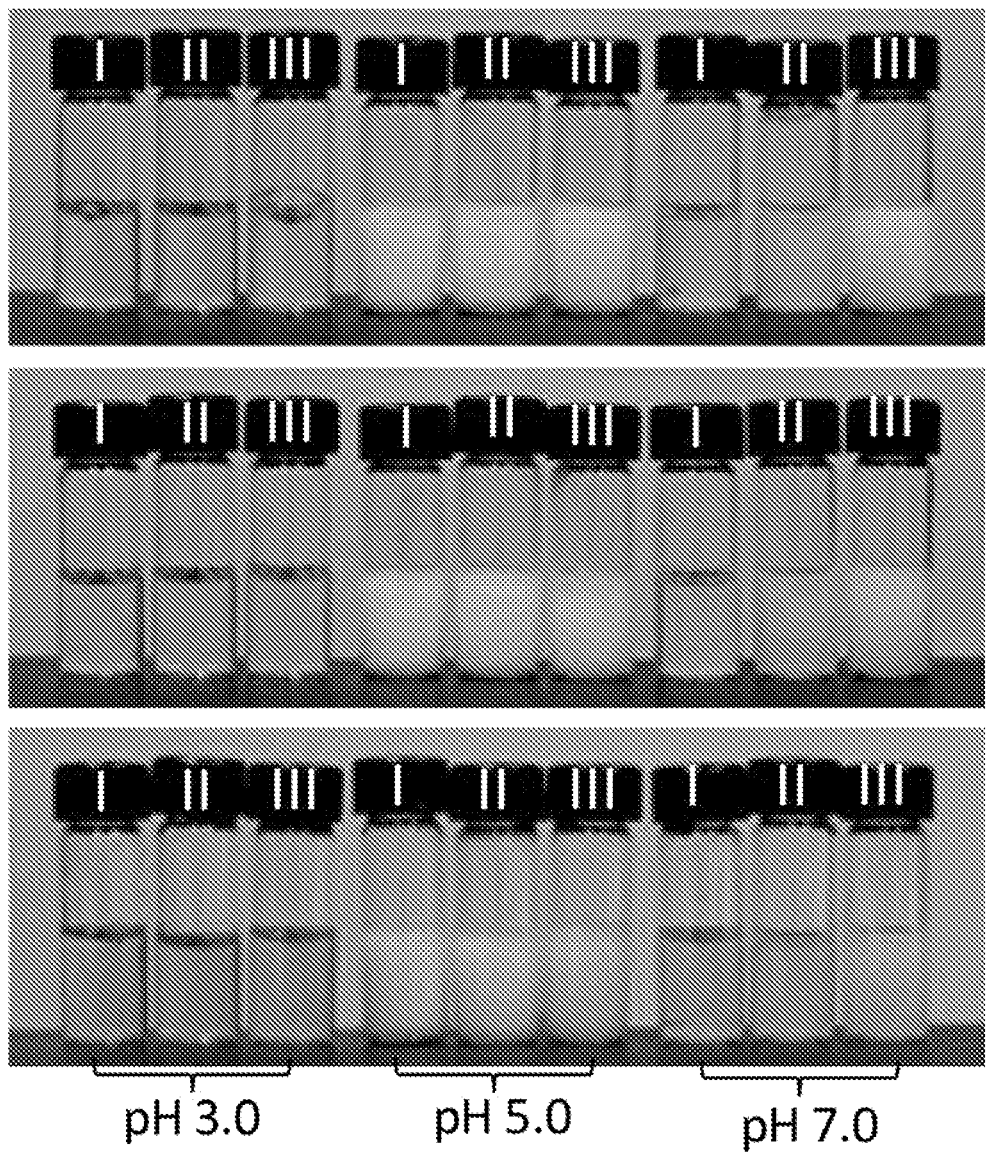
FIG. 1. Photographs of untreated 5% whey protein isolate (top), mixture of 5% whey protein isolate and 10% maltodextrin (middle), and 15% of whey protein-maltodextrin (1:2) conjugate (bottom) samples after heating at 80° C. for 15 min. Vials labeled with I, II, and III indicate 0, 50, and 100 mM NaCl, respectively.
Figure 2A:
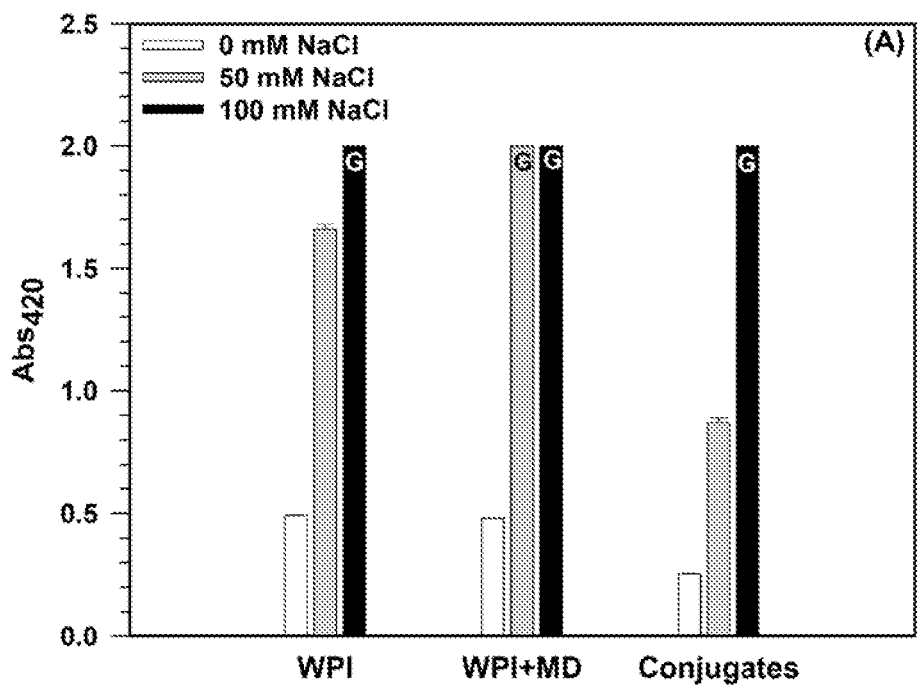
FIGS. 2A-2D. Absorbance at 420 and 600 nm for untreated samples of 5% whey protein isolate (WPI), mixture of 5% whey protein isolate and 10% maltodextrin (WPI+MD), and 15% of whey protein-maltodextrin (1:2) conjugate samples after heating at 80° C. for 15 min. Sample pH was 7.0 for (A) and (B) and 3.0 for (C) and (D). Samples labeled with a letter "G" indicate formation of gels. Error bars are standard deviations from two replicates.
Figure 2B:
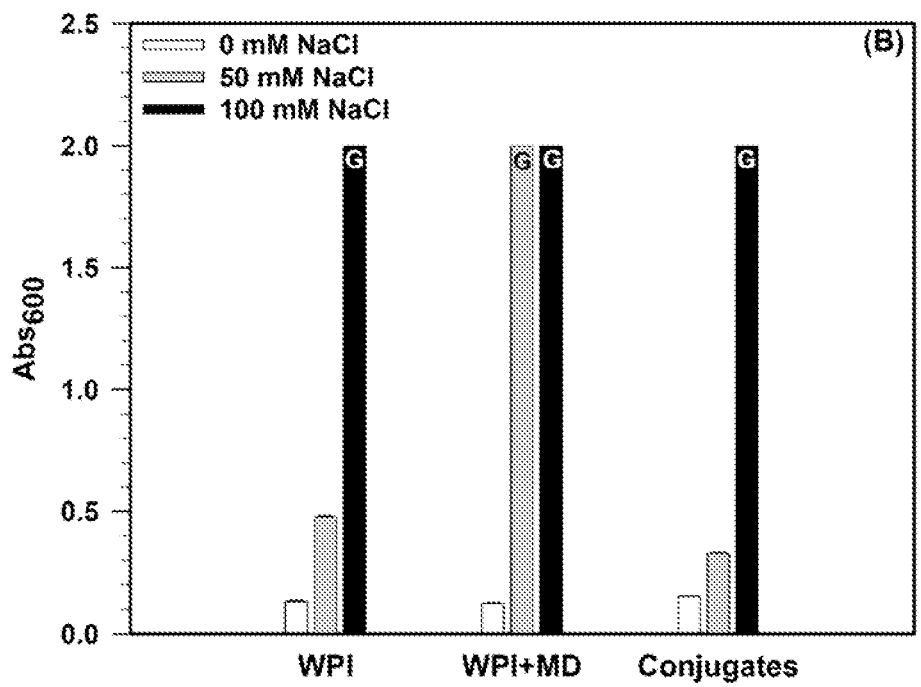
Figure 2C:
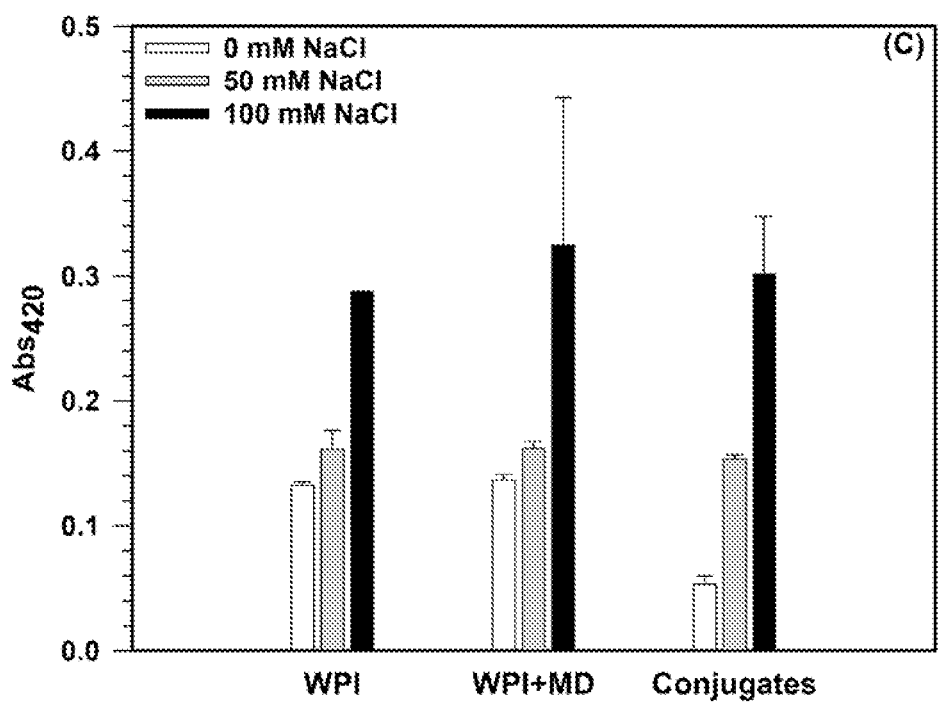
Figure 2D:
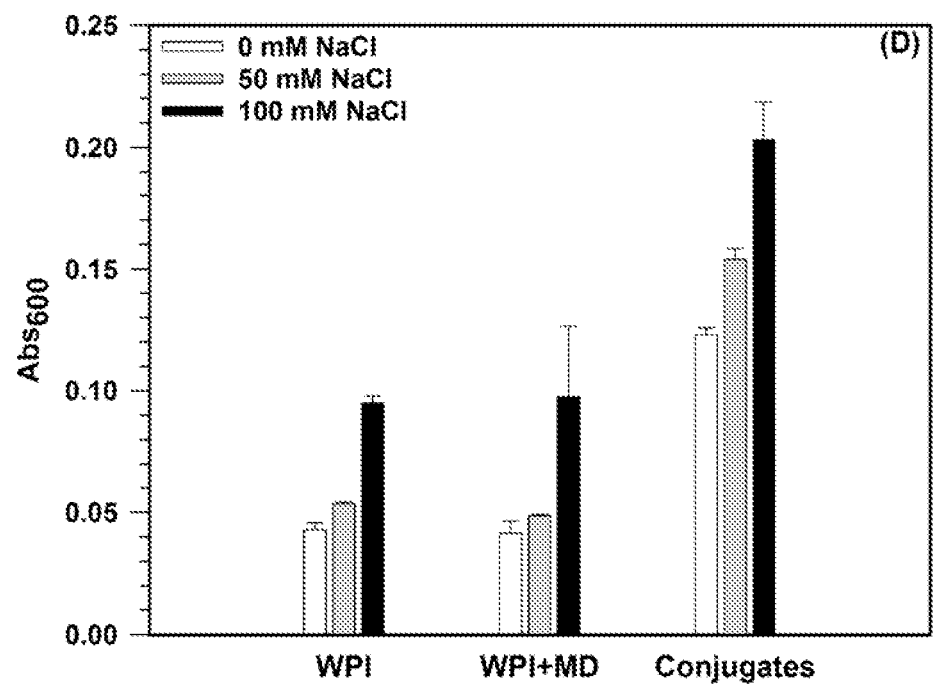
Figure 3A:
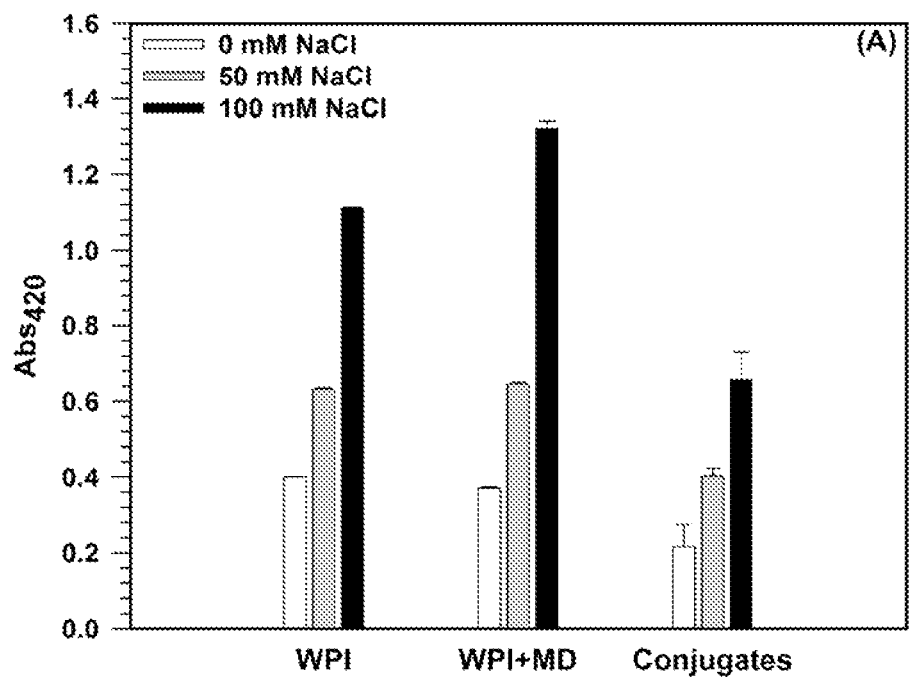
FIGS. 3A-3D. Absorbance at 420 and 600 nm for preheated samples of 5% whey protein isolate (WPI), mixture of 5% whey protein isolate and 10% maltodextrin (WPI+MD), and 15% of whey protein-maltodextrin (1:2) conjugate samples after heating at 80° C. for 15 min. Sample pH was 7.0 for (A) and (B) and 3.0 for (C) and (D). Samples labeled with a letter "G" indicate formation of gels. Error bars are standard deviations from two replicates.
Figure 3B:
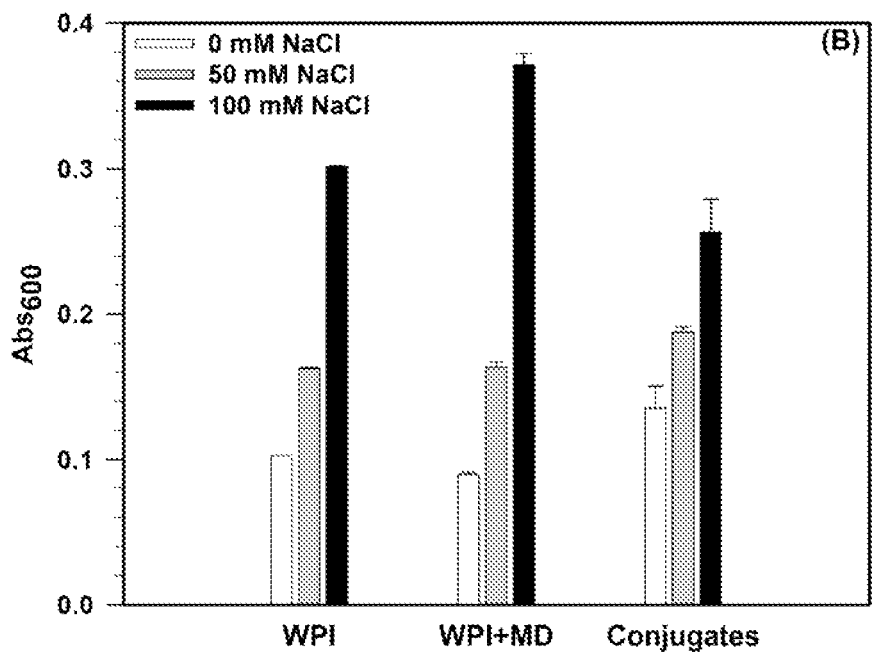
Figure 3C:
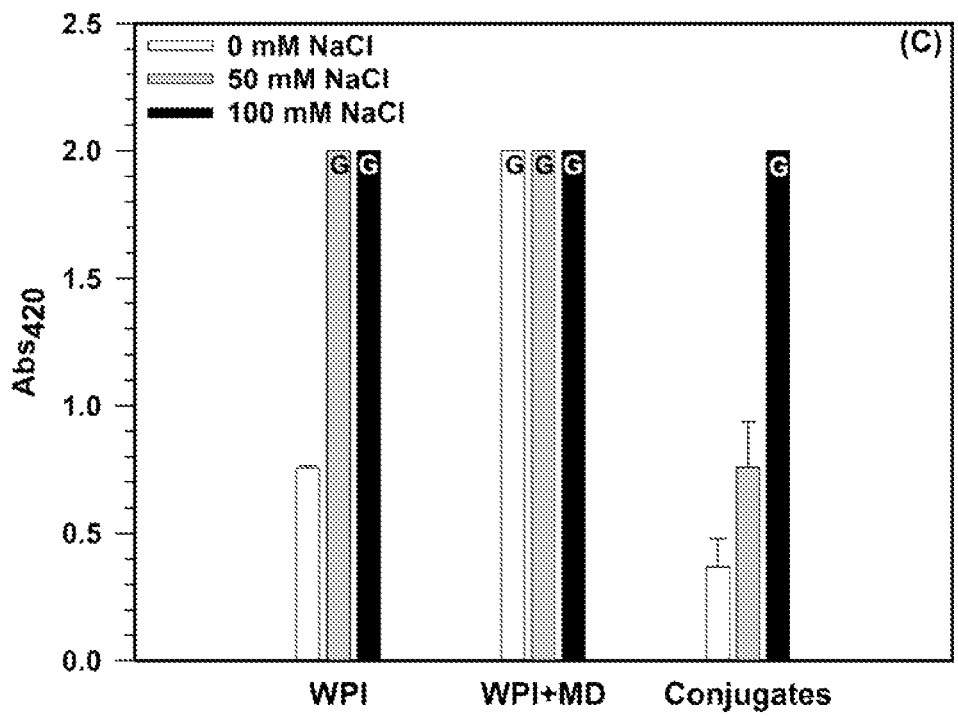
Figure 3D:
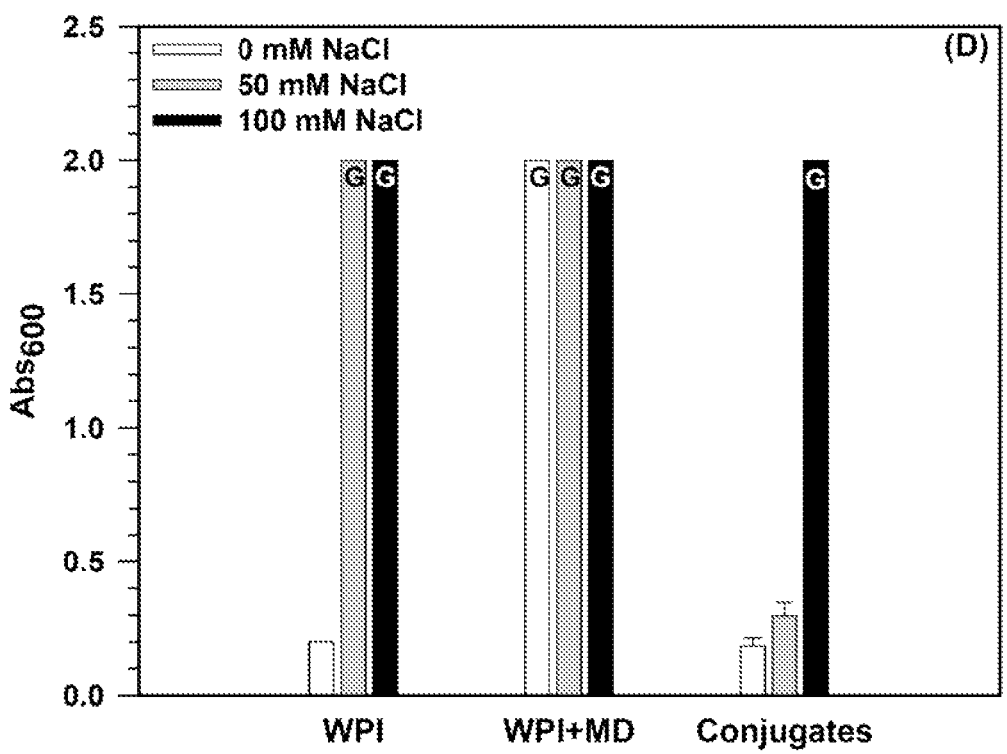
Figure 4A:
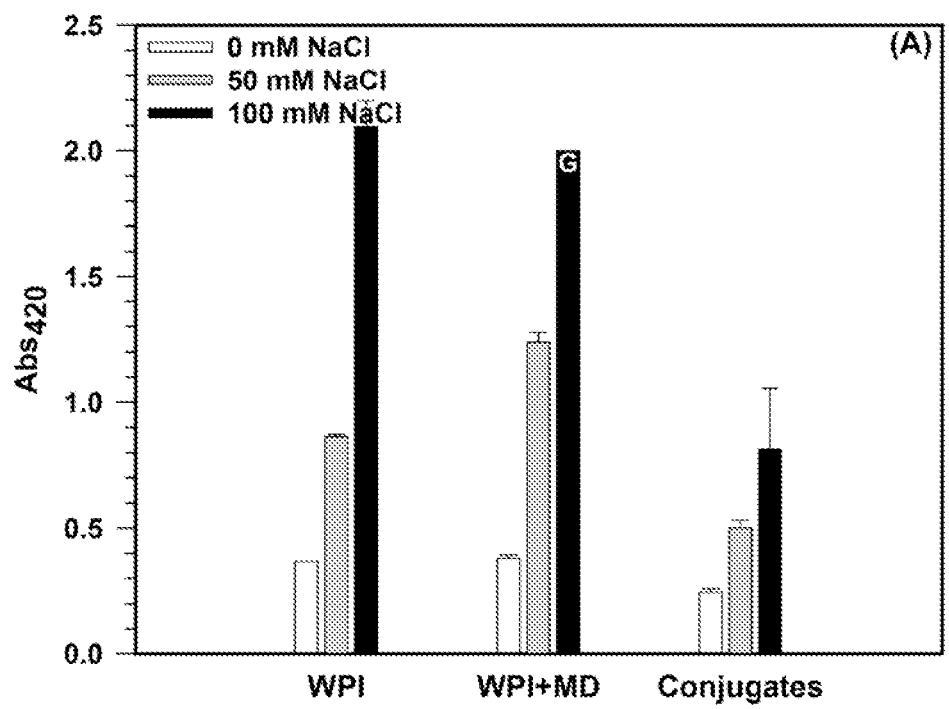
FIGS. 4A-4D. Absorbance at 420 and 600 nm for enzymatically pretreated samples of 5% whey protein isolate (WPI), mixture of 5% whey protein isolate and 10% maltodextrin (WPI+MD), and 15% of whey protein-maltodextrin (1:2) conjugate samples after heating at 80° C. for 15 min. Transglutaminase was used at 22 U/g WPI. Sample pH was 7.0 for (A) and (B) and 3.0 for (C) and (D). Samples labeled with a letter "G" indicate formation of gels. Error bars are standard deviations from two replicates.
Figure 4B:
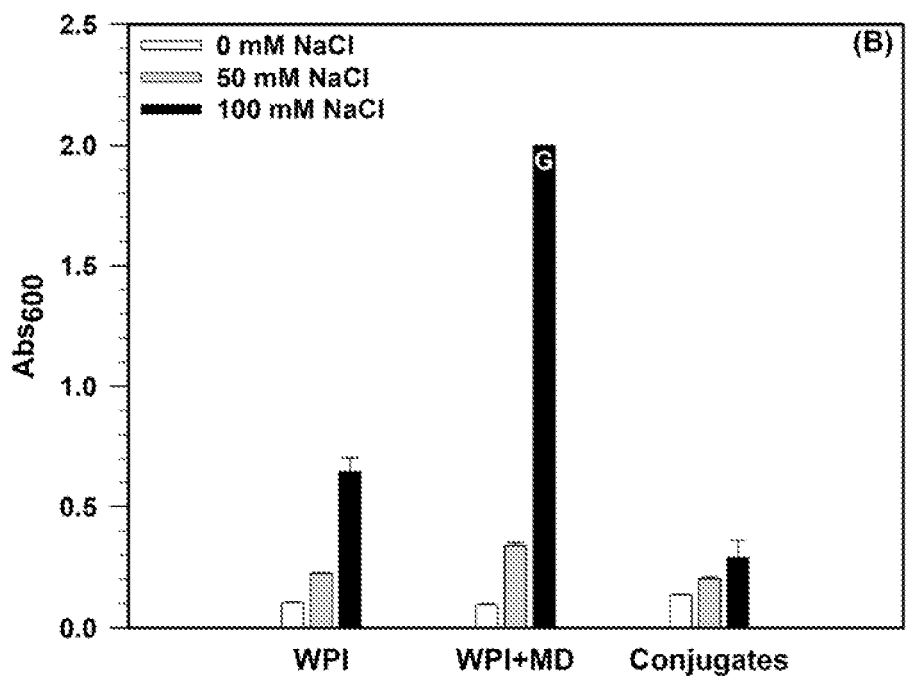
Figure 4C:
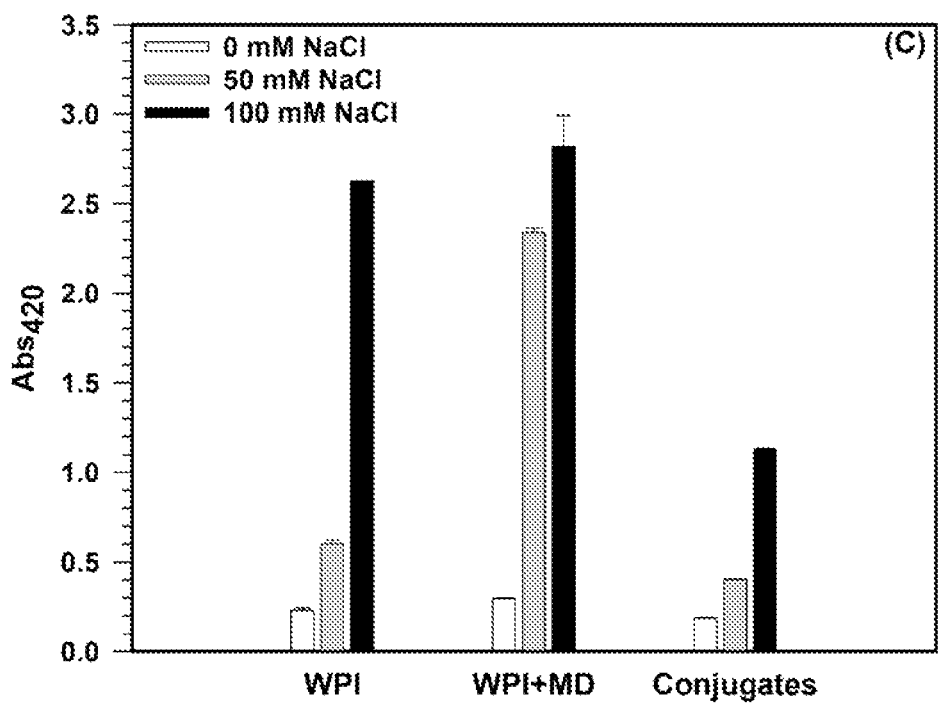
Figure 4D:
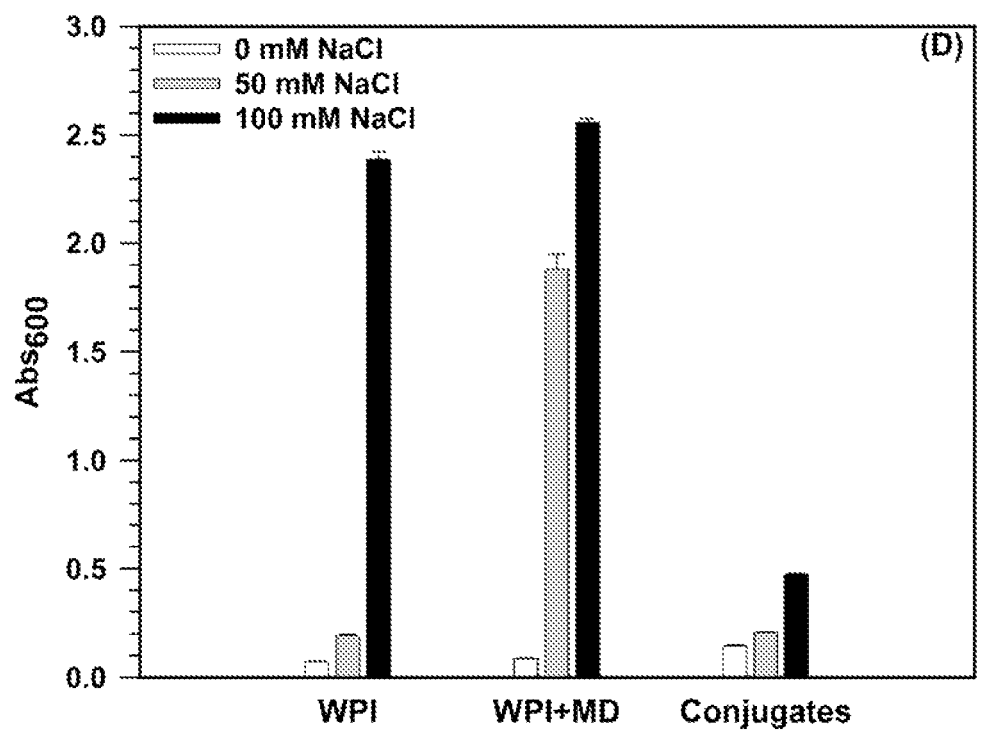
Figure 5A:
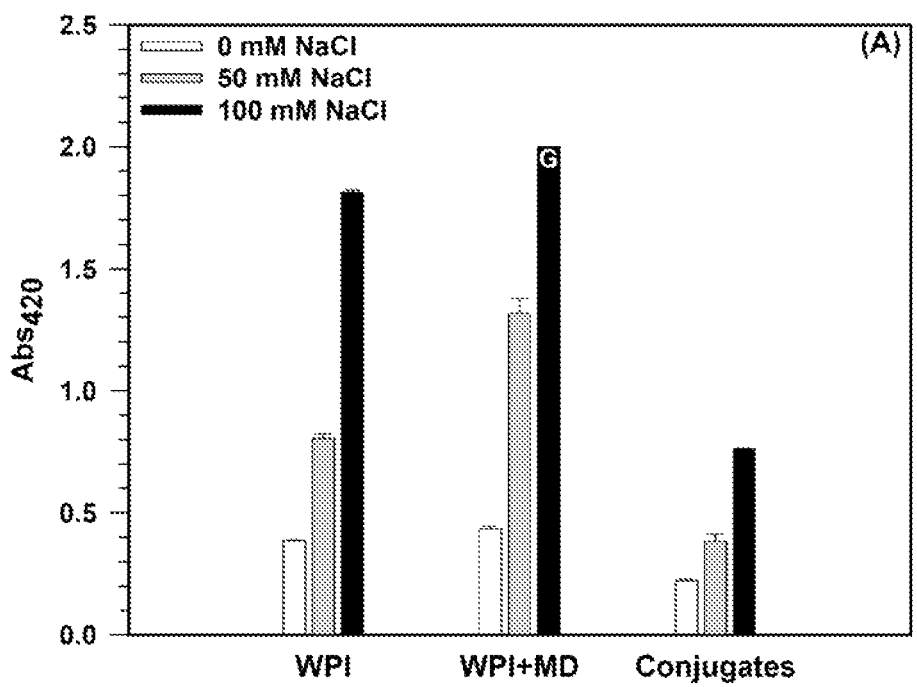
FIGS. 5A-5D. Absorbance at 420 and 600 nm for enzymatically pretreated samples of 5% whey protein isolate (WPI), mixture of 5% whey protein isolate and 10% maltodextrin (WPI+MD), and 15% of whey protein-maltodextrin (1:2) conjugate samples after heating at 80° C. for 15 min. Transglutaminase was used at 55 U/g WPI. Sample pH was 7.0 for (A) and (B) and 3.0 for (C) and (D). Samples labeled with a letter "G" indicate formation of gels. Error bars are standard deviations from two replicates.
Figure 5B:
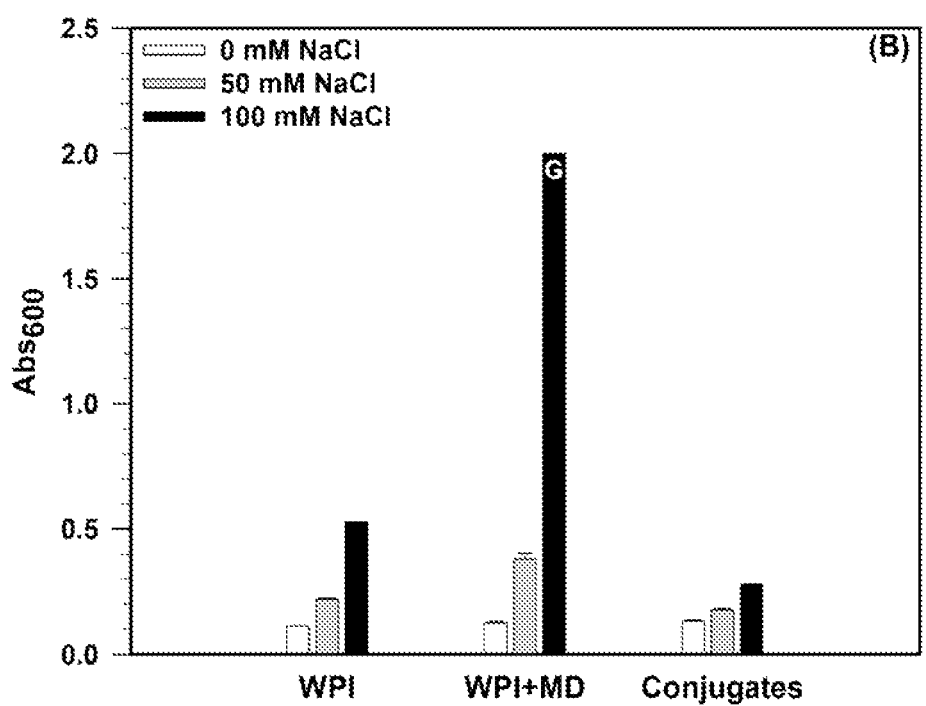
Figure 5C:
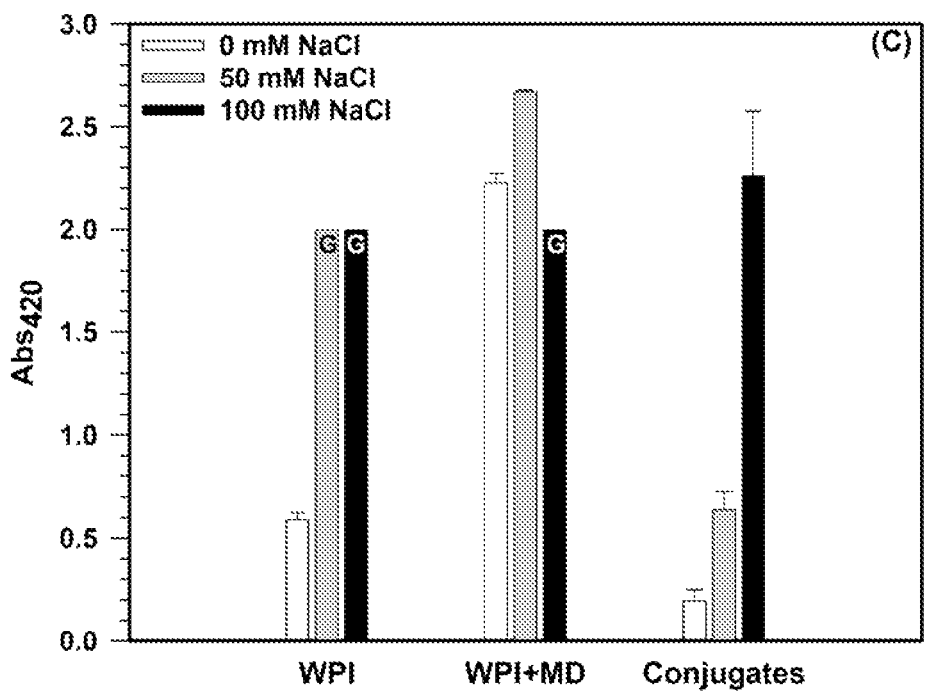
Figure 5D:
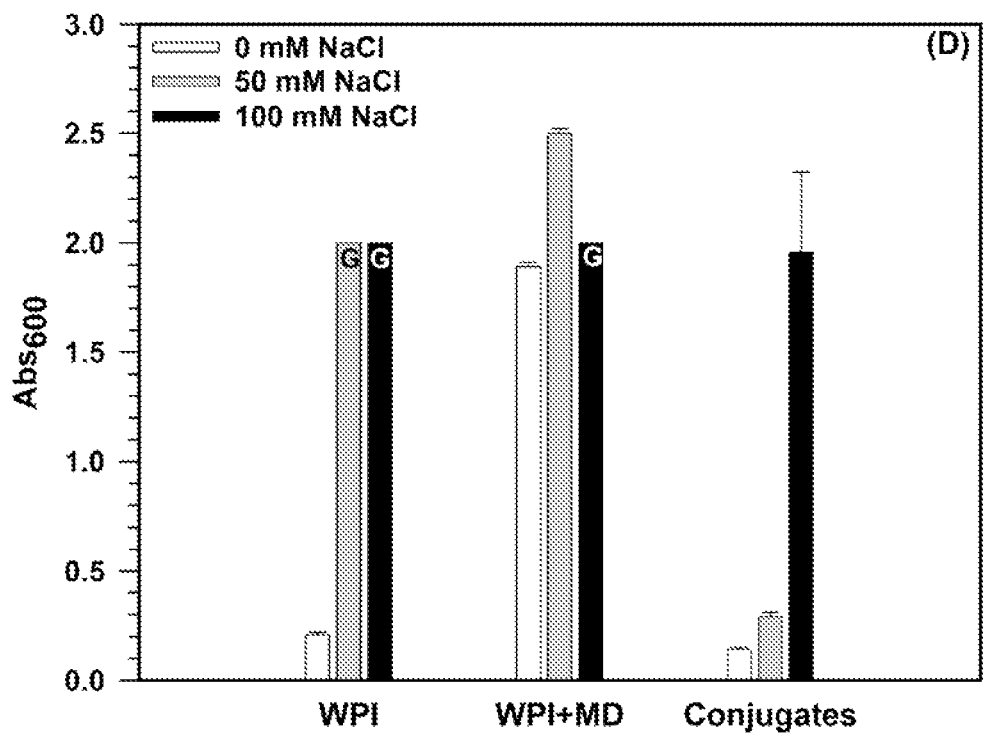

After heating at 80° C. for 15 min, photographs and absorbance values of untreated samples are shown in FIGS. 1 and 2, respectively. Samples were mostly clear at pH 3.0, regardless of ionic strength, corresponding to $Abs_{420}$ lower than 0.4 and $Abs_{600}$ lower than 0.25 at 600 nm. At pH 5.0, all samples formed turbid gels. At pH 7.0 and 0 mM NaCl, samples were mostly clear, with $Abs_{420}$ lower than 0.5 and $Abs_{600}$ lower than 0.2. At pH 7.0 and 50 mM NaCl, the WPI sample became a turbid, viscous solution, with a much higher Abs420 than Abs600, the mixture of WPI and MD became a gel, while the conjugate sample had better clarity than the WPI sample. At 100 mM NaCl, all samples formed turbid gels. Visual appearance was consistent with turbidity measurements that showed a large absorbance value for a visually more turbid sample.

Samples after Preheating at 80° C. For 15 Min

After adjusting pH and salt concentration, the preheated samples were clear at pH 7.0 but became turbid when pH was 5.0 or even formed gels for the mixture of WPI and MD (photos not shown). At pH 3.0, the preheated samples were generally more turbid than samples at pH 7.0, which is well-known in the literature for acid-induced aggregation of preheated WPI (Alting et al., 2004).

After heating at 80° C. for 15 min, all samples at pH 5.0 formed gels (results not shown). The absorbance of other samples after heating is shown in FIG. 3. At pH 7.0, the preheated samples had improved heat stability when compared to the untreated samples (FIGS. 1 and 2), especially for conjugate samples, and showed increased turbidity at a higher salt concentration. At pH 3.0, the preheated conjugate sample were clearer than the preheated WPI and WPI+MD samples when NaCl was not added; at 50 mM NaCl, the preheated conjugate sample did not form a gel, while other two samples formed gels; when NaCl was 100 mM, all preheated samples formed gels. Preheating thus improved heat stability of WPI at pH 7.0 but worsened the heat stability at pH 3.0. In the case that repeated heating is needed for certain applications, conjugates may be a viable option at pH 3.0.

Samples Pretreated by Enzymatic Cross-Linking

Samples in this group were pretreated by 22 or 55 U/g WPI TGase. After pretreatment at the lower enzyme level, all samples (images not shown) had similar clarity to untreated samples. After heating at 80° C. for 15 min, all enzymatically cross-linked samples at pH 5.0 formed gels (FIG. 4). At pH 7.0 and 3.0, sample clarity followed the order of conjugates>WPI>WPI+MD (FIG. 4). Comparing FIG. 7 to FIG. 5, enzymatic treatment improved heat stability of conjugates better than the preheat treatment. Similar results were observed at the higher level of TGase used in cross-linking (FIG. 5).

Samples Sequentially Treated by Heat and Enzyme

Figure 6A:
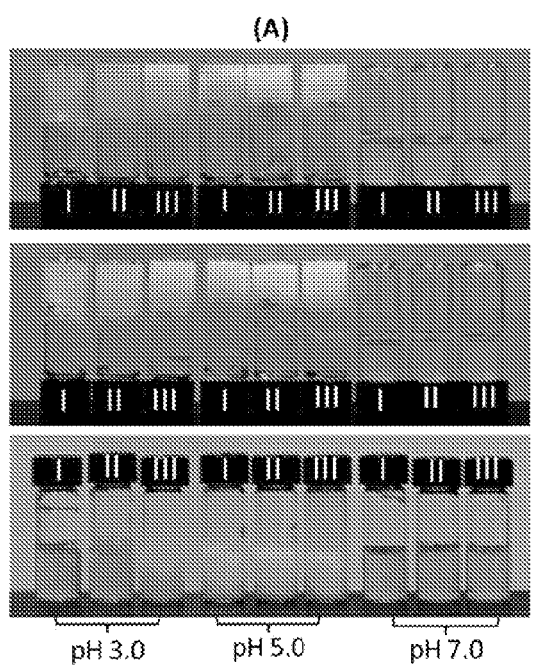
FIGS. 6A-6B. Photographs of sequentially treated samples of 5% whey protein isolate (top), mixture of 5% whey protein isolate and 10% maltodextrin (middle), and 15% of whey protein-maltodextrin (1:2) conjugate (bottom) samples after heating at 80° C. for 15 min. Sequential treatments were performed by preheating at 80° C. for 15 min followed by 22 (A) or 55 (B) U/g WPI of transglutaminase. Vials labeled with I and II indicate 0, 50, and 100 mM NaCl, respectively, while labels of 1 and 5 indicate the heating duration.
Figure 6B:
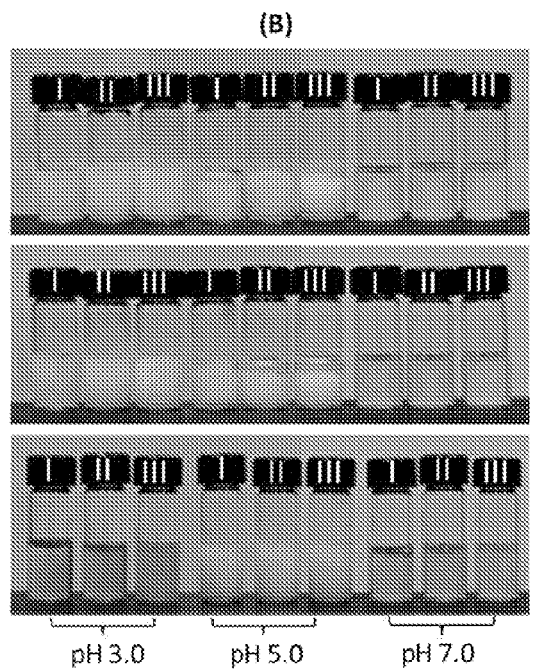
Figure 7A:
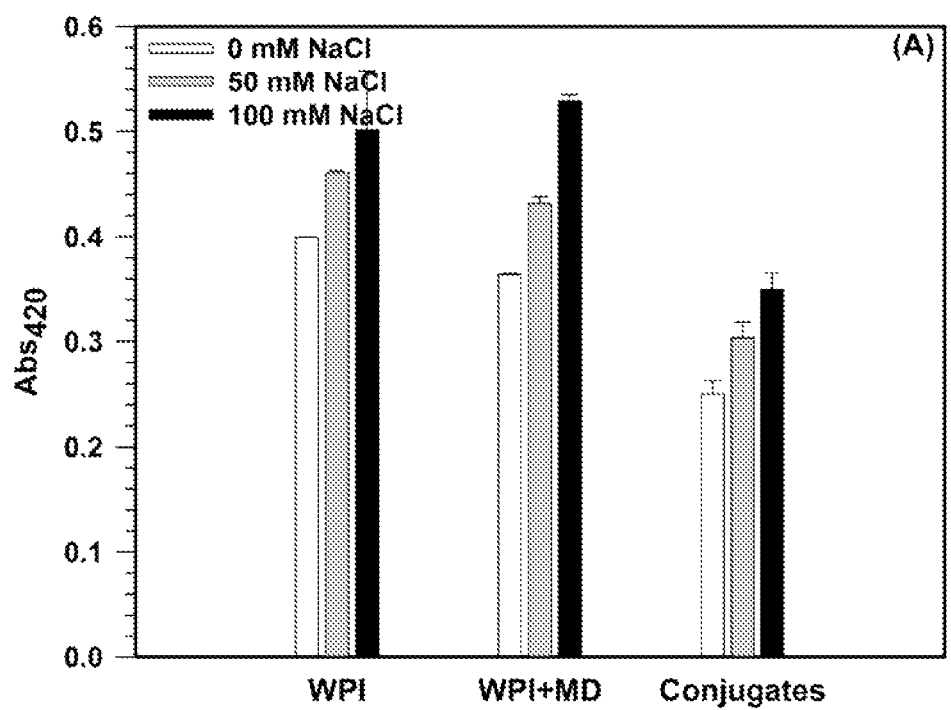
FIGS. 7A-7D. Absorbance at 420 and 600 nm for sequentially pretreated samples of 5% whey protein isolate (WPI), mixture of 5% whey protein isolate and 10% maltodextrin (WPI+MD), and 15% of whey protein-maltodextrin (1:2) conjugate samples after heating at 80° C. for 15 min. Sequential treatments were performed by preheating at 80° C. for 15 min followed by 22 U/g WPI of transglutaminase. Sample pH was 7.0 for (A) and (B) and 3.0 for (C) and (D). Samples labeled with a letter "G" indicate formation of gels. Error bars are standard deviations from two replicates.
Figure 7B:
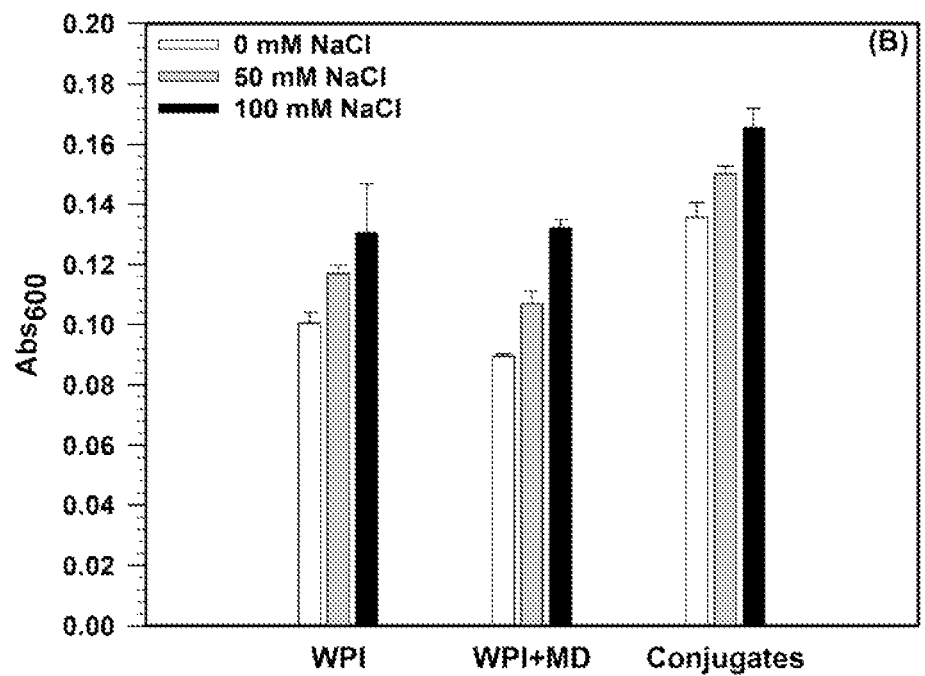
Figure 7C:
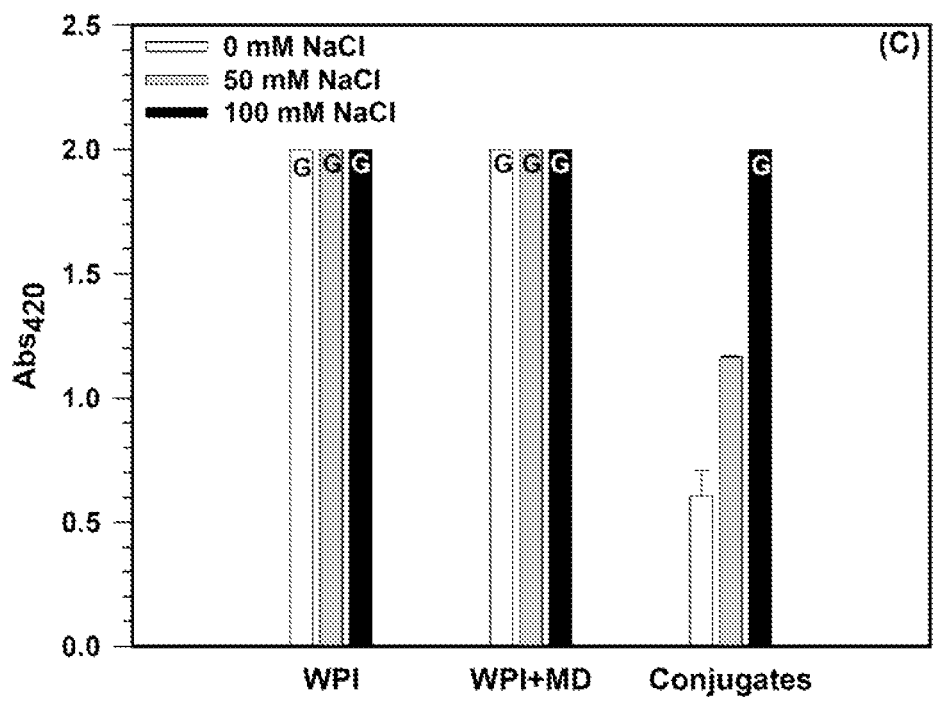
Figure 7D:
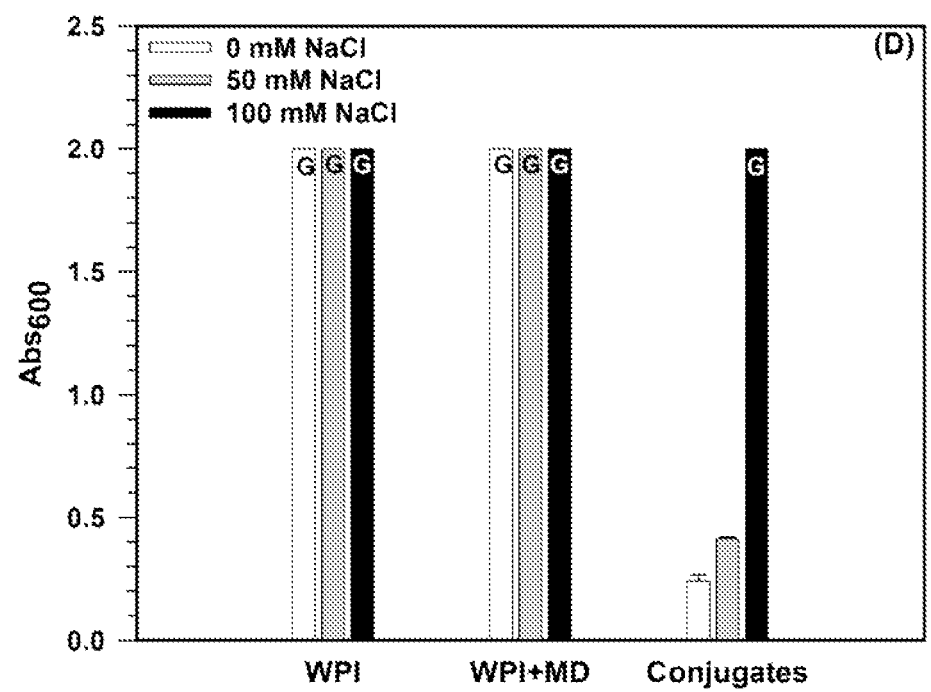
Figure 8A:
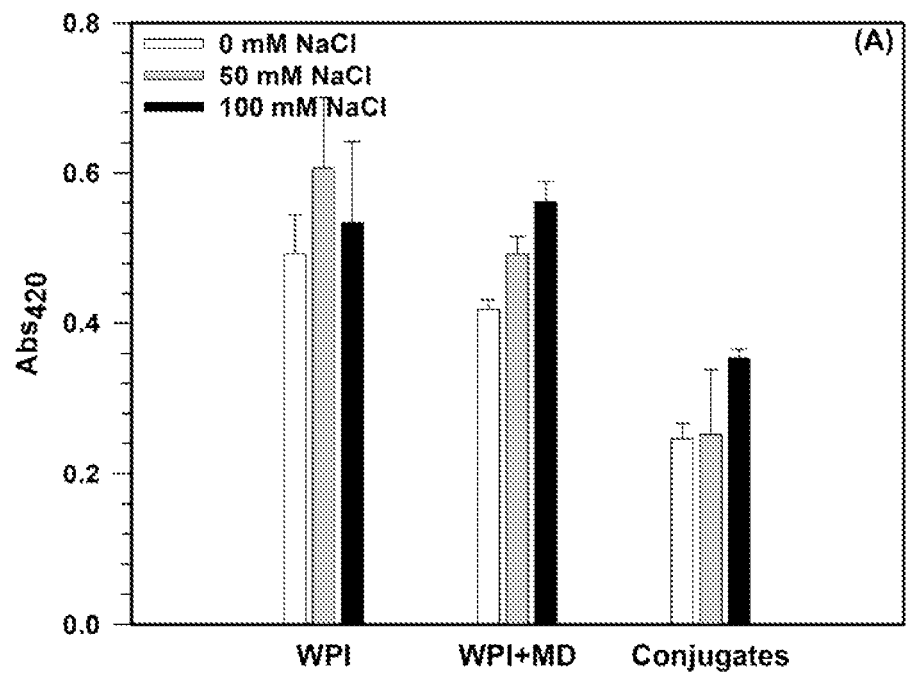
FIGS. 8A-8D. Absorbance at 420 and 600 nm for sequentially pretreated samples of 5% whey protein isolate (WPI), mixture of 5% whey protein isolate and 10% maltodextrin (WPI+MD), and 15% of whey protein-maltodextrin (1:2) conjugate samples after heating at 80° C. for 15 min. Sequential treatments were performed by preheating at 80° C. for 15 min followed by 55 U/g WPI of transglutaminase. Sample pH was 7.0 for (A) and (B) and 3.0 for (C) and (D). Samples labeled with a letter "G" indicate formation of gels. Error bars are standard deviations from two replicates.
Figure 8B:
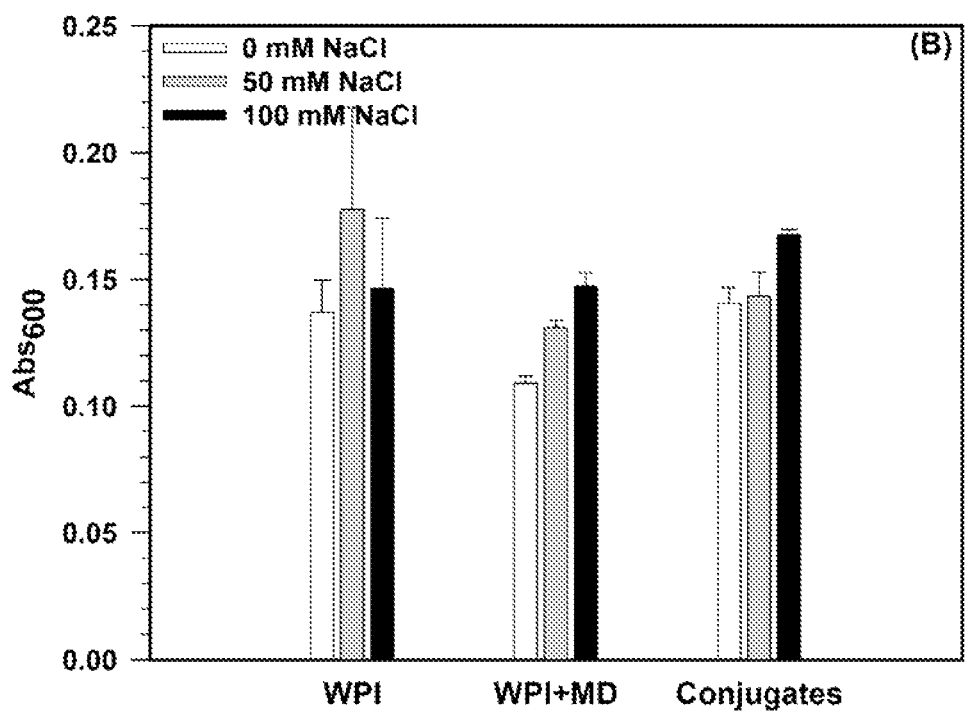
Figure 8C:
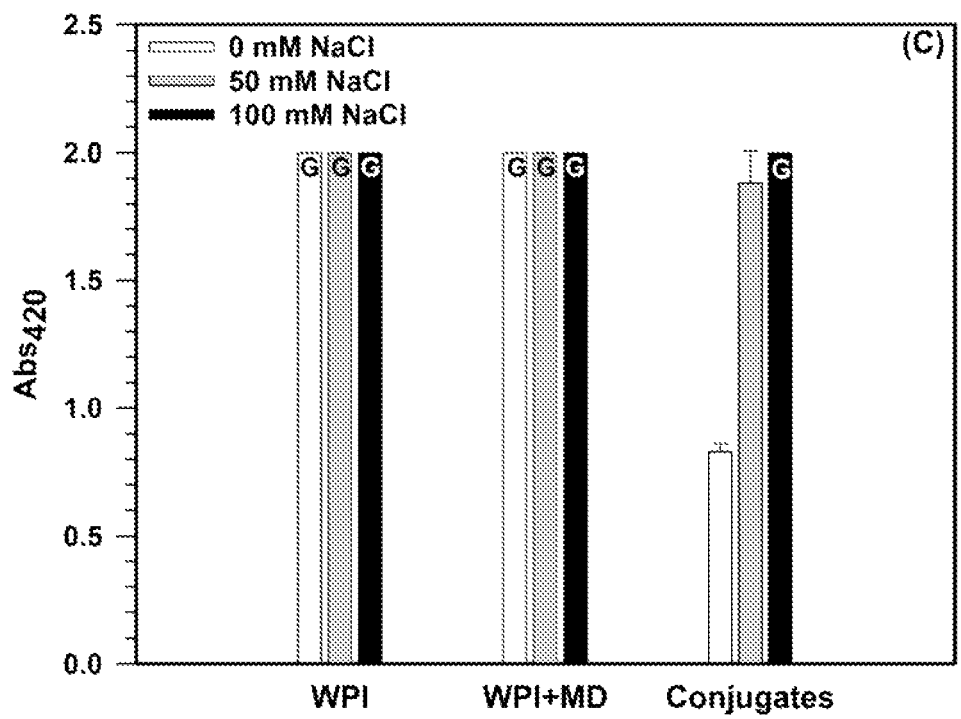
Figure 8D:
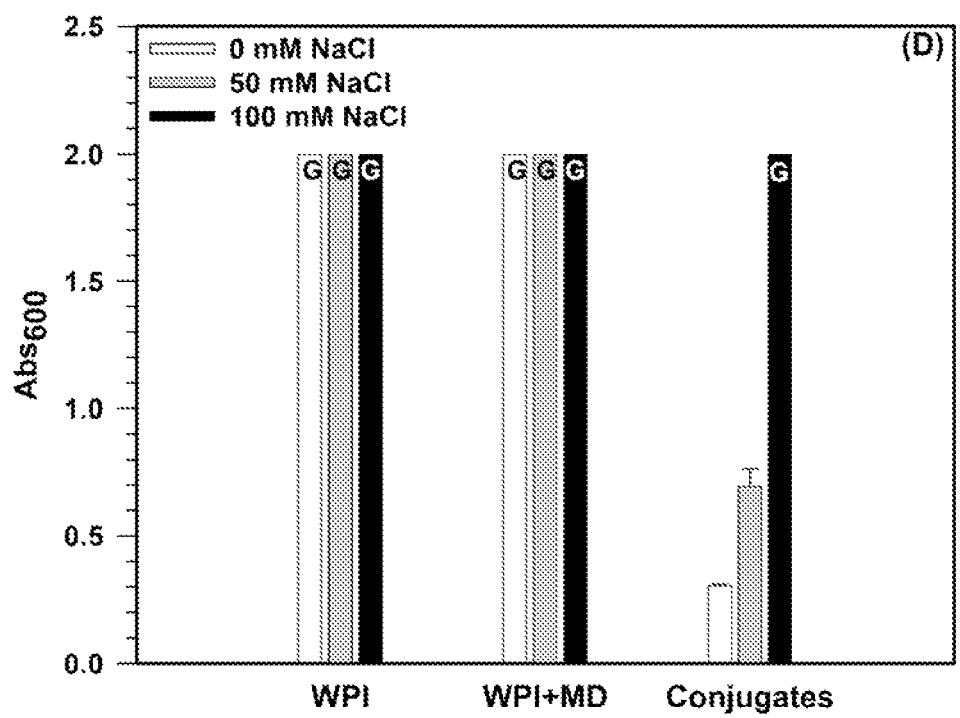
Figure 9:
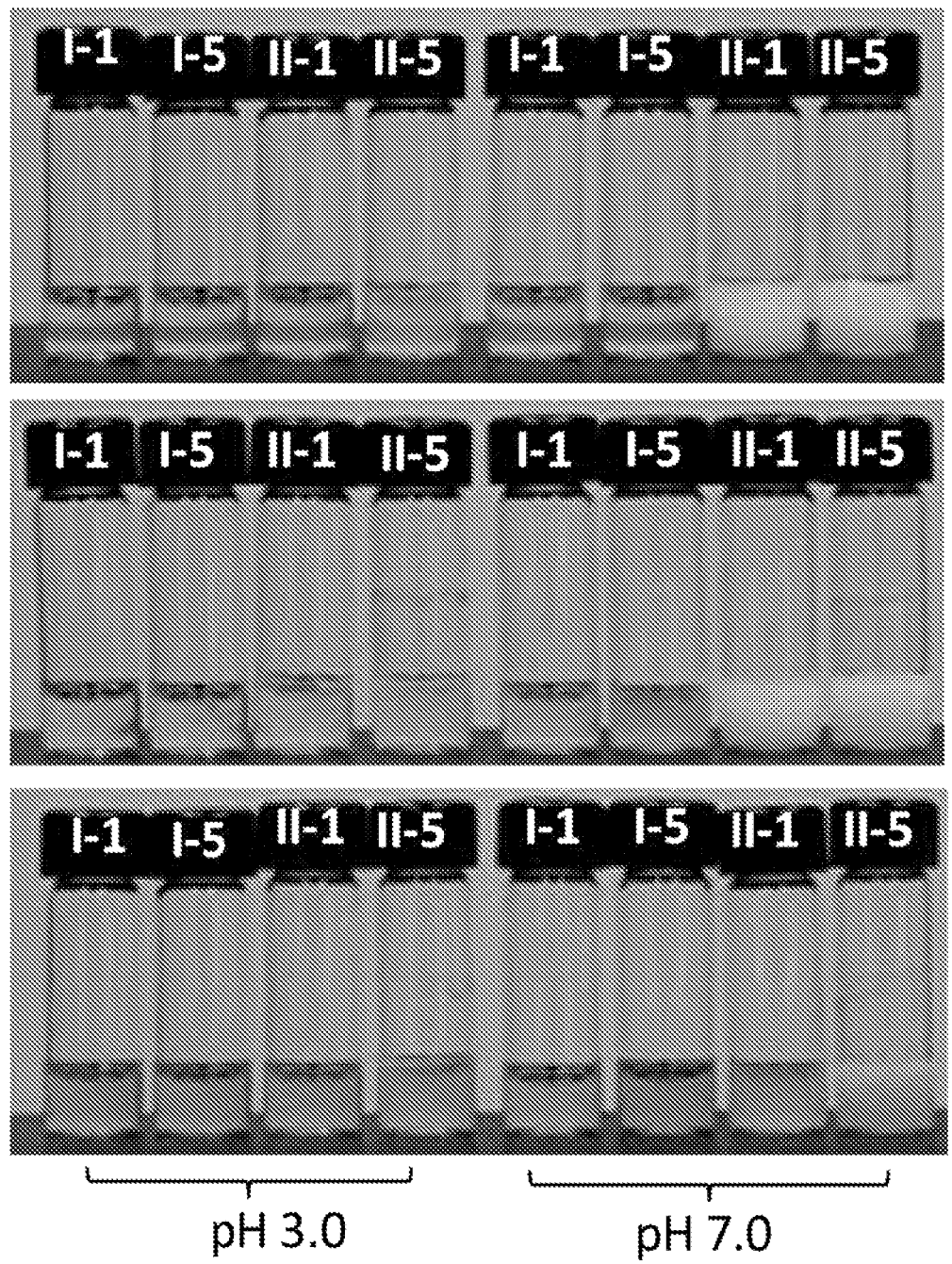
FIG. 9. Photographs of untreated samples after heating. Photographs of untreated 5% whey protein isolate (top), mixture of 5% whey protein isolate and 10% maltodextrin (middle), and 15% of whey protein-maltodextrin (1:2) conjugate (bottom) samples after heating at 138° C. for 1 or 5 min. Vials labeled with I and II indicate 0 and 50 mM NaCl, respectively, while labels of 1 and 5 indicate the heating duration.
Figure 10A:
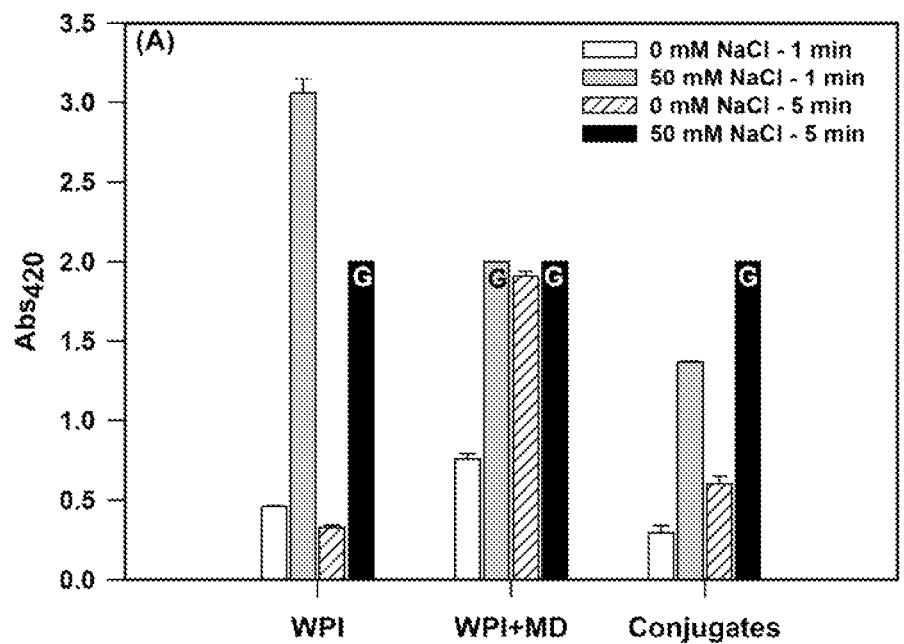
FIGS. 10A-10D. Absorbance at 420 and 600 nm for untreated samples of 5% whey protein isolate (WPI), mixture of 5% whey protein isolate and 10% maltodextrin (WPI+MD), and 15% of whey protein-maltodextrin (1:2) conjugate samples after heating at 138° C. for 1 or 5 min. Sample pH was 7.0 for (A) and (B) and 3.0 for (C) and (D). Samples labeled with a letter "G" indicate formation of gels. Error bars are standard deviations from two replicates.
Figure 10B:
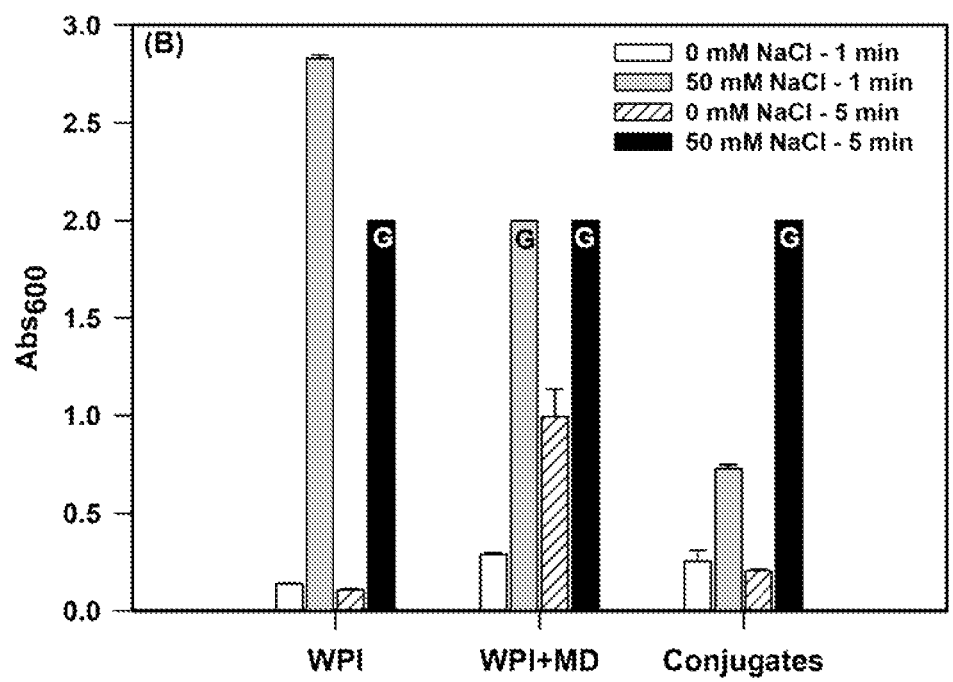
Figure 10C:
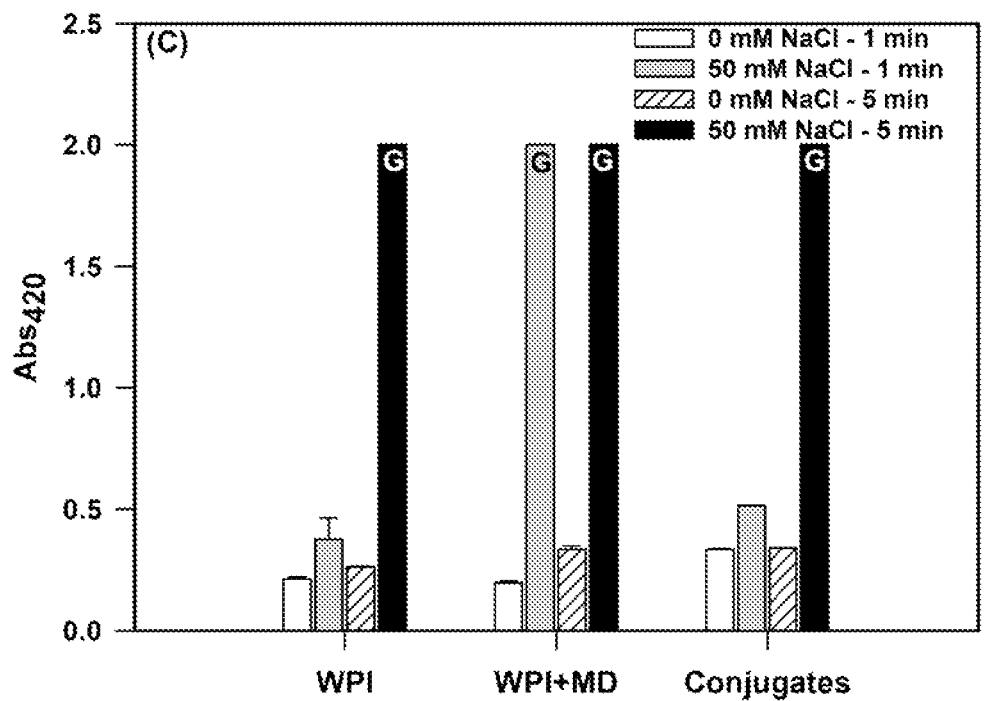
Figure 10D:
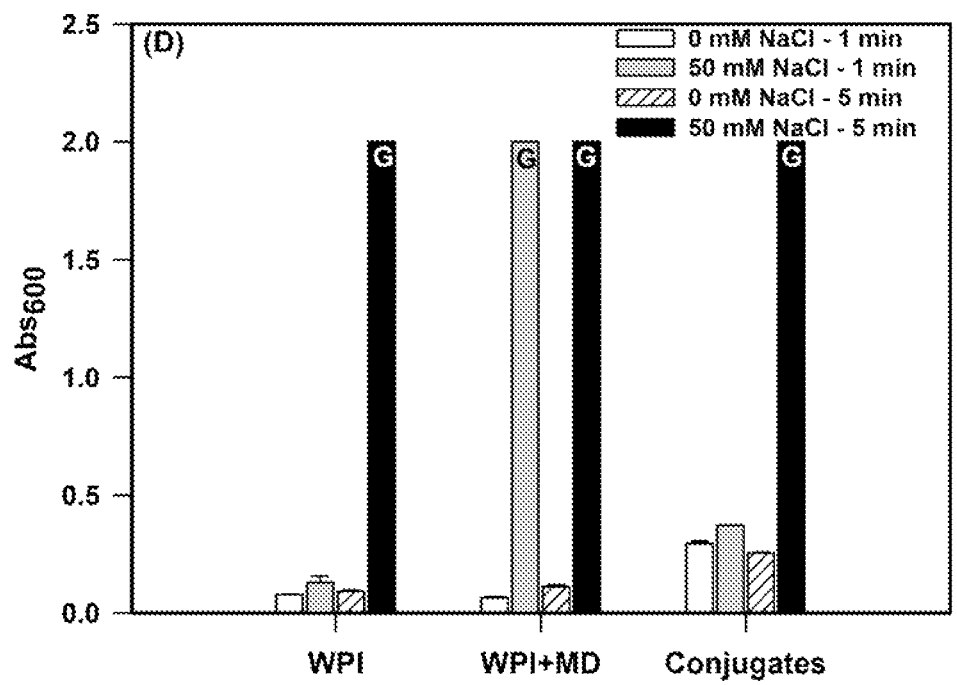
Figure 11A:
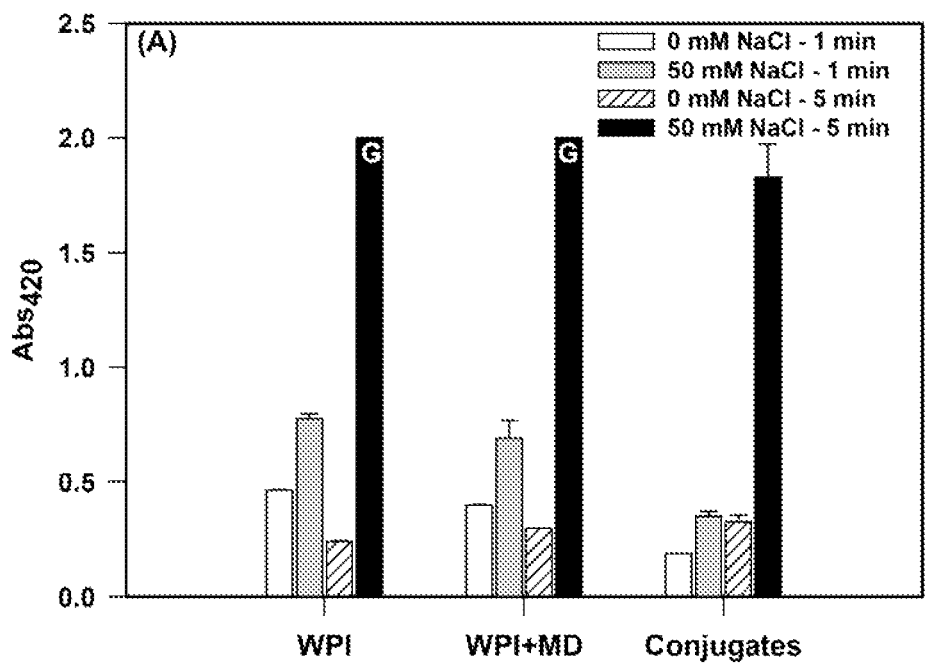
FIGS. 11A-11D. Absorbance at 420 and 600 nm for preheated samples of 5% whey protein isolate (WPI), mixture of 5% whey protein isolate and 10% maltodextrin (WPI+MD), and 15% of whey protein-maltodextrin (1:2) conjugate samples after heating at 138° C. for 1 or 5 min. Sample pH was 7.0 for (A) and (B) and 3.0 for (C) and (D). Samples labeled with a letter "6" indicate formation of gels. Error bars are standard deviations from two replicates.
Figure 11B:
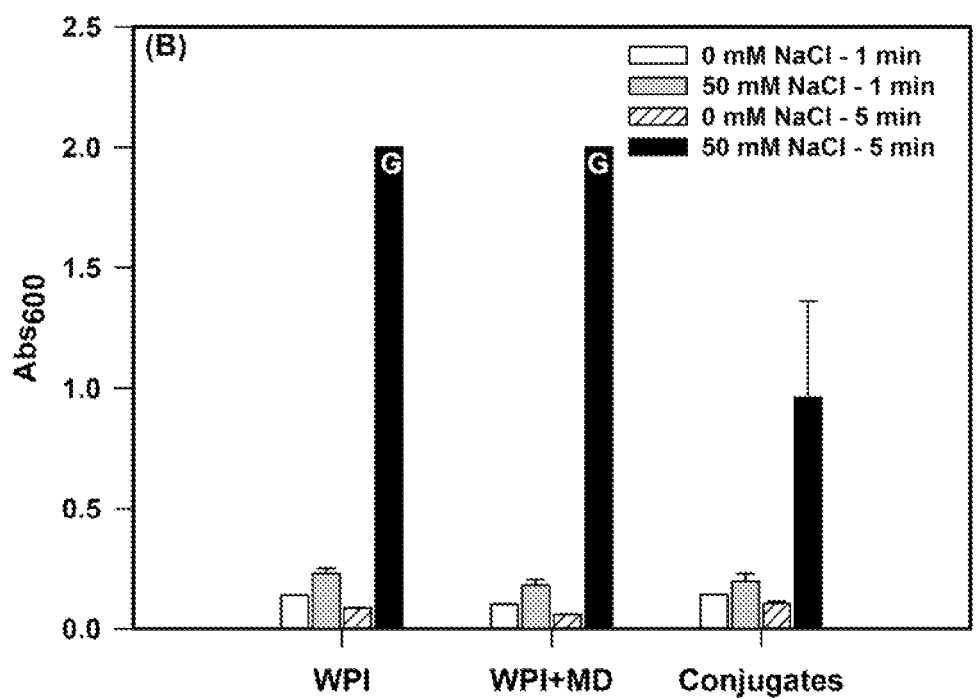
Figure 11C:
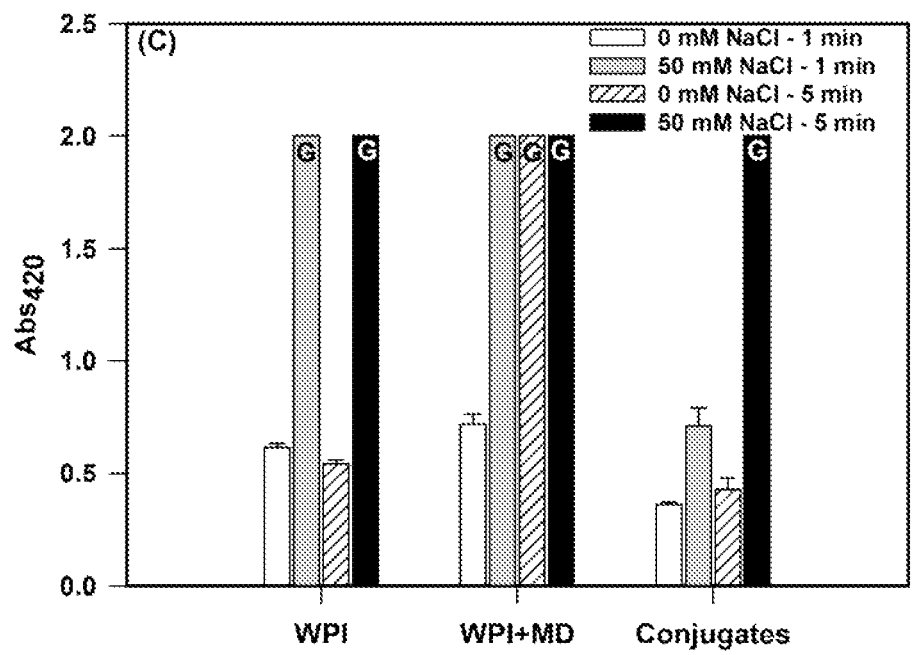
Figure 11D:
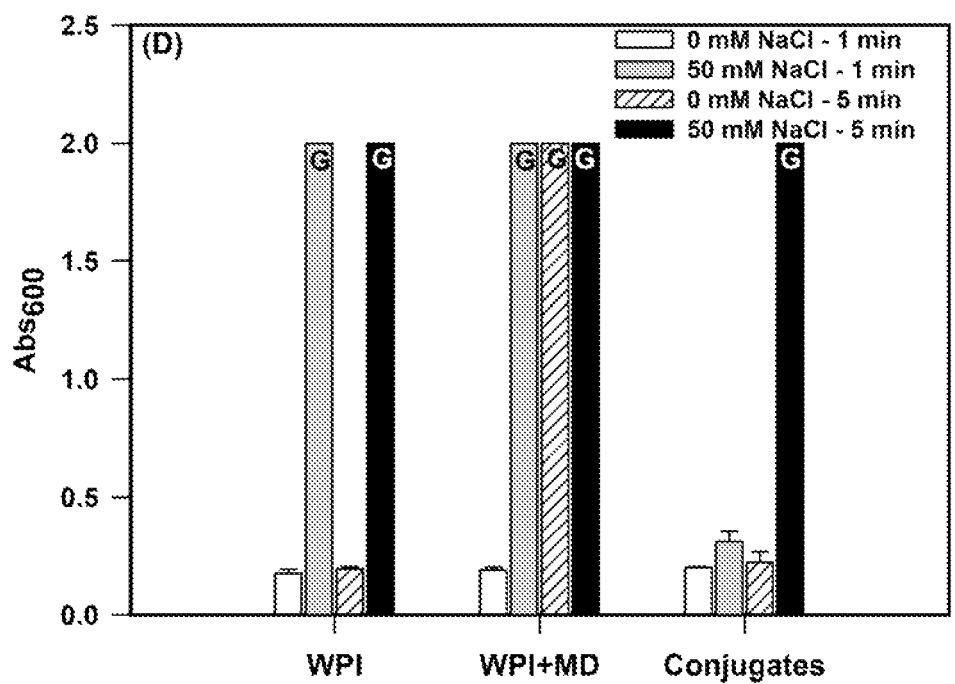
Figure 12A:
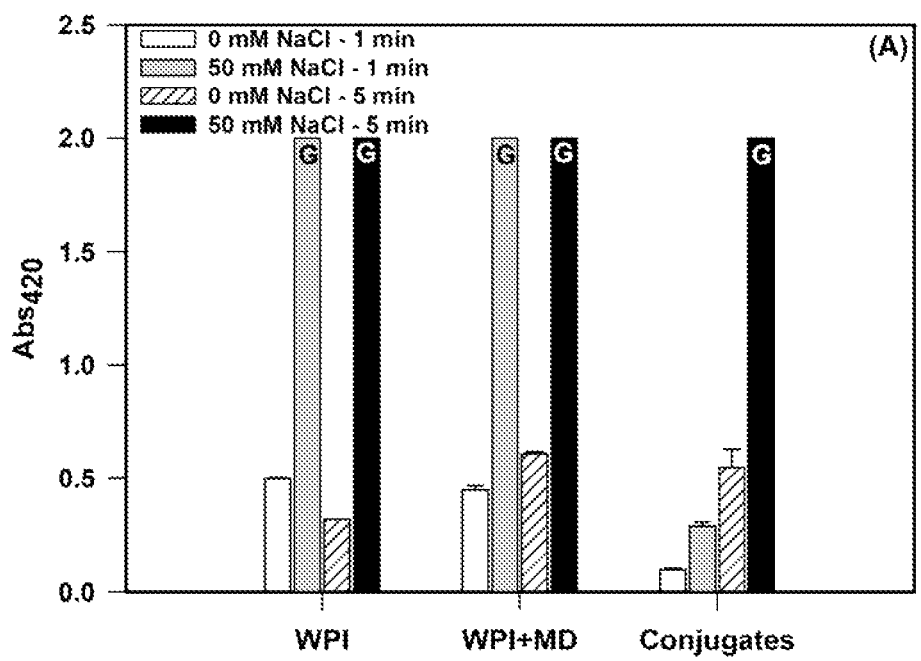
FIGS. 12A-12D. Absorbance at 420 and 600 nm for enzymatically pretreated samples of 5% whey protein isolate (WPI), mixture of 5% whey protein isolate and 10% maltodextrin (WPI+MD), and 15% of whey protein-maltodextrin (1:2) conjugate samples after heating at 138° C. for 1 or 5 min. Transglutaminase was used at 22 U/g WPI. Samples were adjusted to pH 7.0 for (A) and (B) and 3.0 for (C) and (D). Samples labeled with a letter "G" indicate formation of gels. Error bars are standard deviations from two replicates.
Figure 12B:
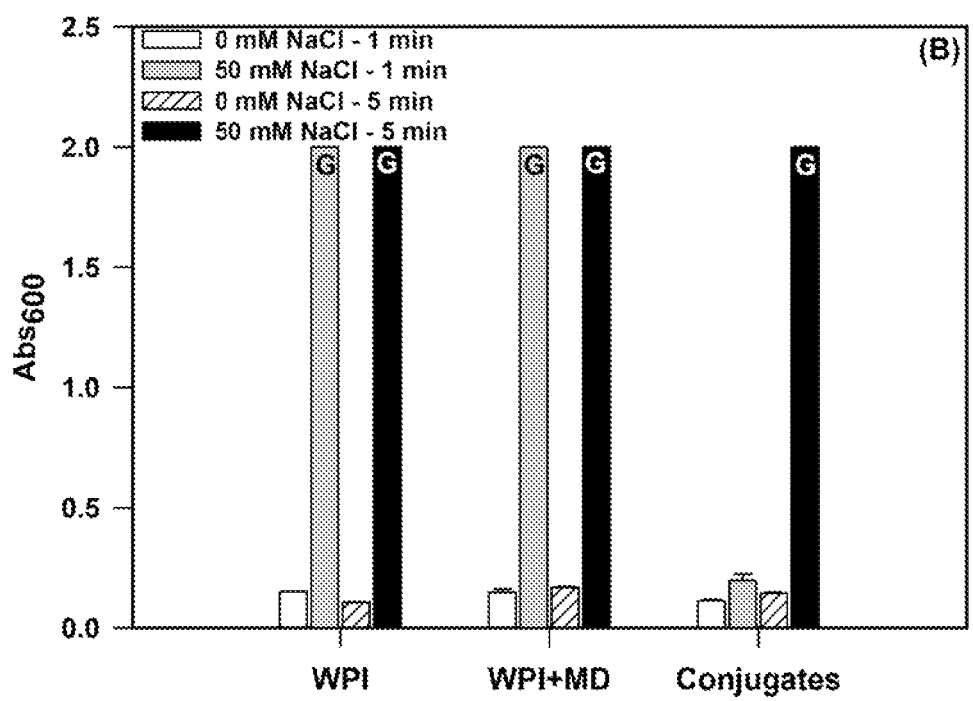
Figure 12C:
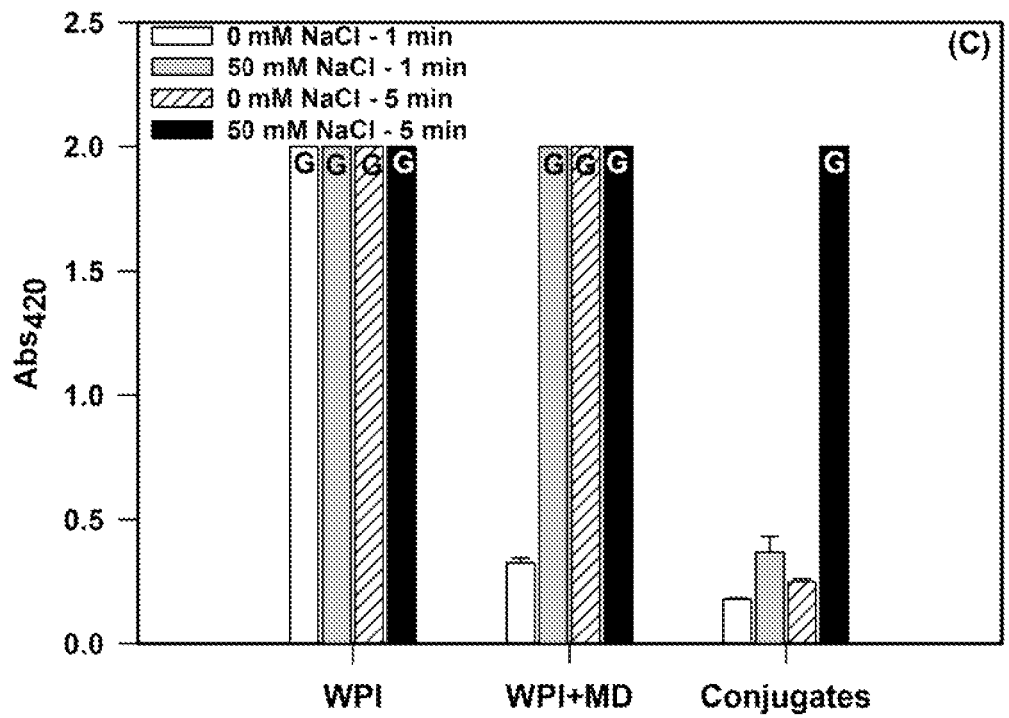
Figure 12D:
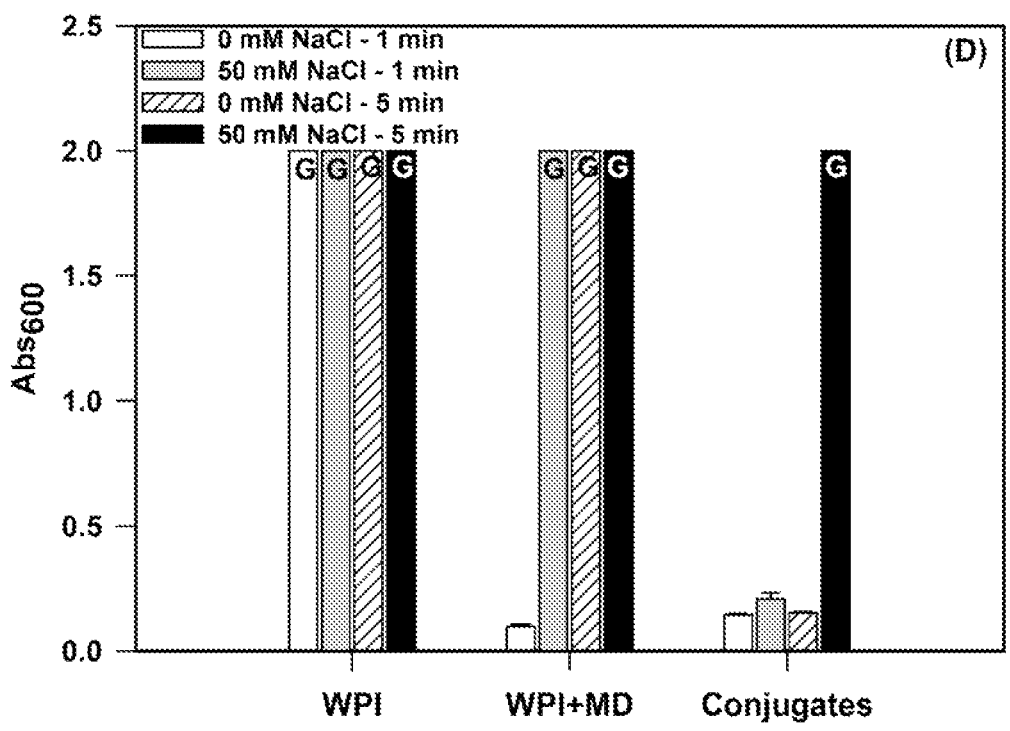
Figure 13A:
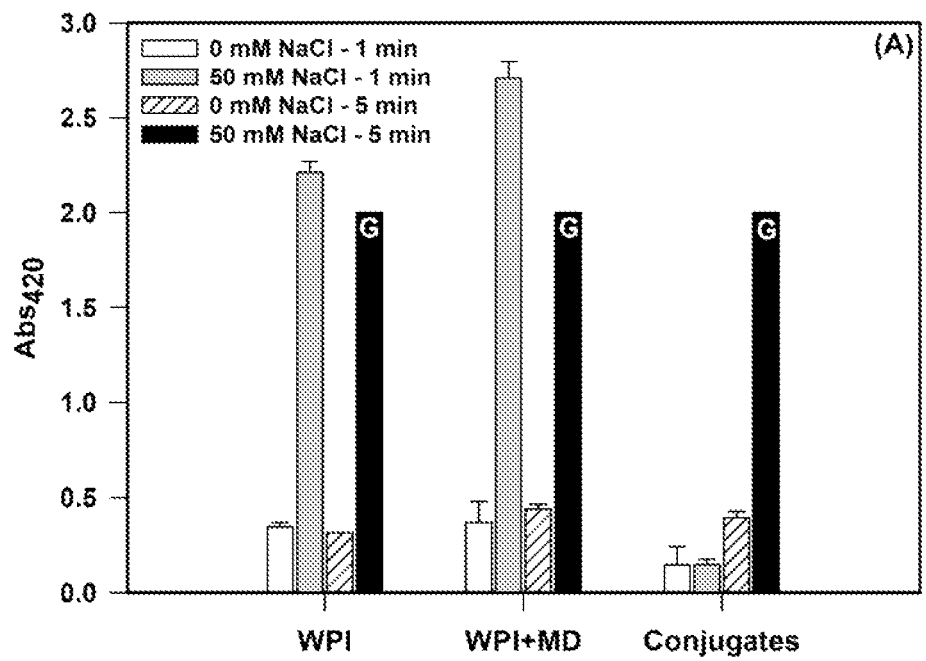
FIGS. 13A-13D. Absorbance at 420 and 600 nm for enzymatically pretreated samples of 5% whey protein isolate (WPI), mixture of 5% whey protein isolate and 10% maltodextrin (WPI+MD), and 15% of whey protein-maltodextrin (1:2) conjugate samples after heating at 138° C. for 1 or 5 min. Transglutaminase was used at 55 U/g WPI. Samples were adjusted to pH 7.0 for (A) and (B) and 3.0 for (C) and (D). Samples labeled with a letter "G" indicate formation of gels. Error bars are standard deviations from two replicates.
Figure 13B:
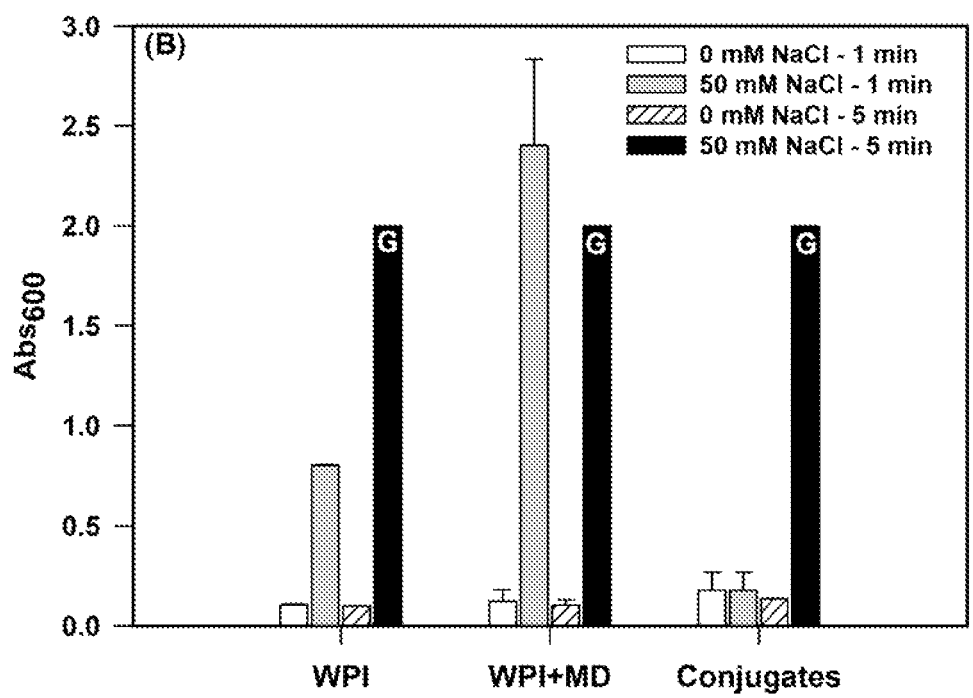
Figure 13C:
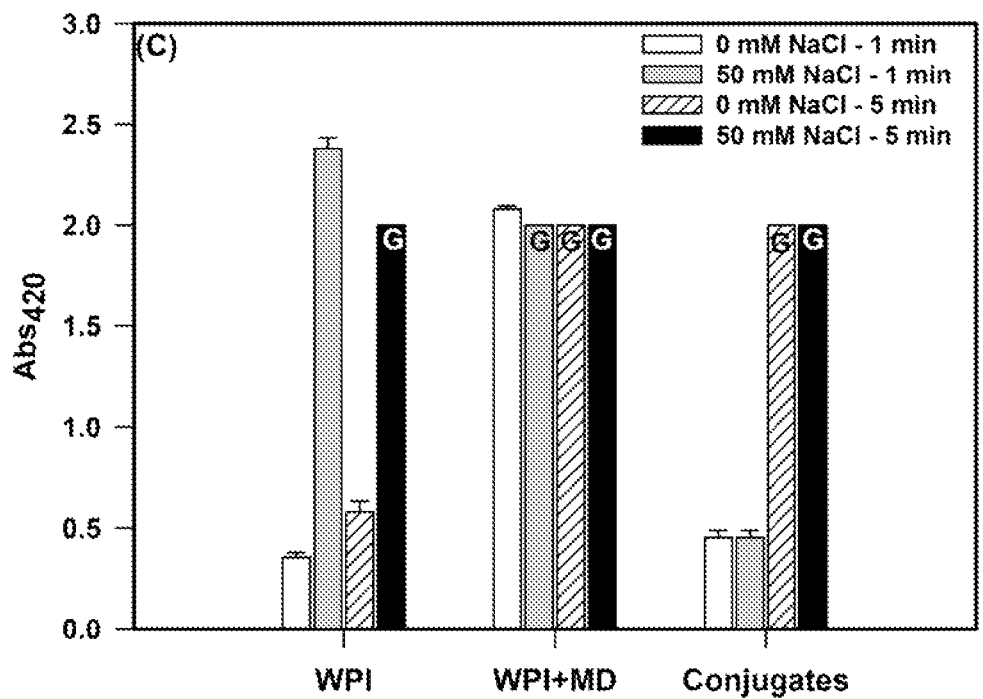
Figure 13D:
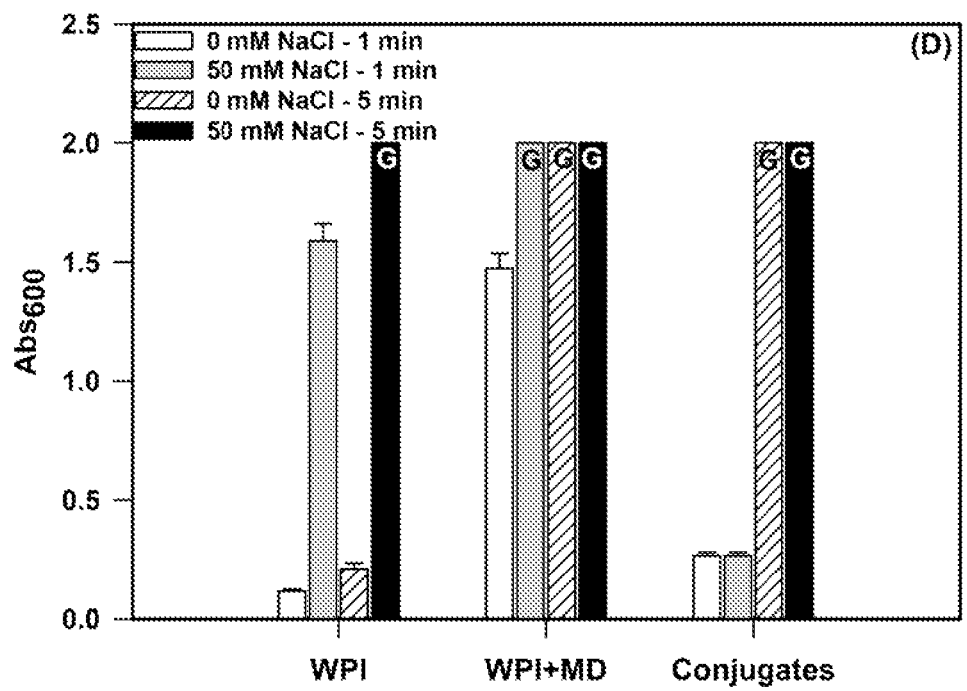
Figure 14A:
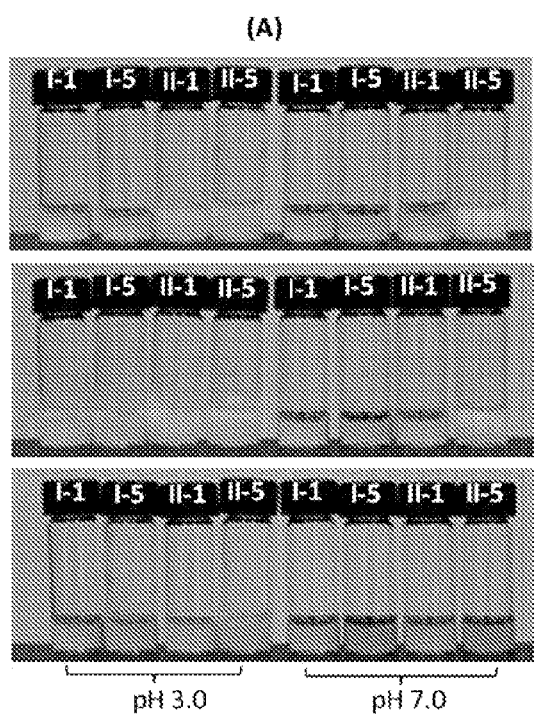
FIGS. 14A-14B. Photographs of sequentially treated samples of 5% whey protein isolate (top), mixture of 5% whey protein isolate and 10% maltodextrin (middle), and 15% of whey protein-maltodextrin (1:2) conjugate (bottom) samples after heating at 138° C. for 1 or 5 min. Sequential treatments were performed by preheating at 80° C. for 15 min followed by 22 (A) or 55 (B) U/g WPI of transglutaminase. Vials labeled with I and II indicate 0 and 50 100 mM NaCl, respectively, while labels of 1 and 5 indicate the heating duration.
Figure 14B:
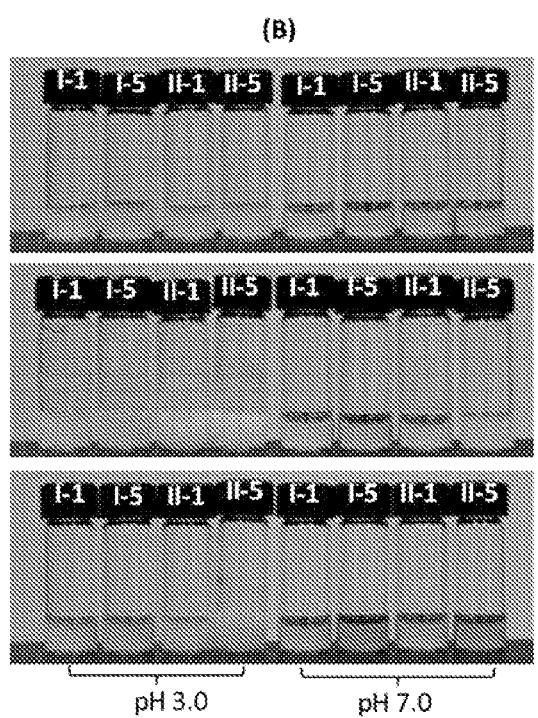
Figure 15A:
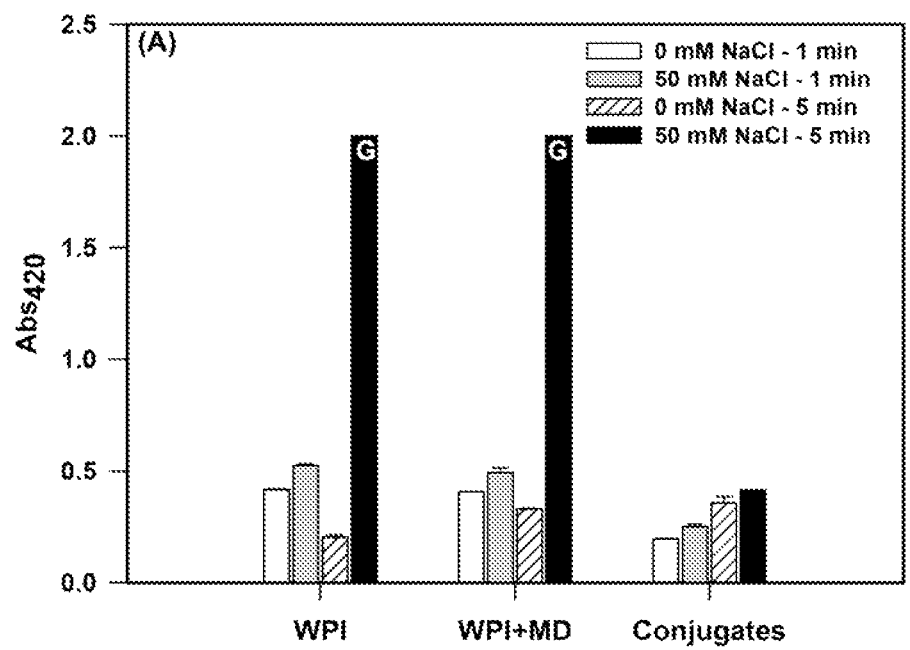
FIGS. 15A-15D. Absorbance at 420 and 600 nm for sequentially pretreated samples of 5% whey protein isolate (WPI), mixture of 5% whey protein isolate and 10% maltodextrin (WPI+MD), and 15% of whey protein-maltodextrin (1:2) conjugate samples after heating at 138° C. for 1 or 5 min. Sequential treatments were performed by preheating at 80° C. for 15 min followed by 22 U/g WPI of transglutaminase. Sample pH was 7.0 for (A) and (B) and 3.0 for (C) and (D). Samples labeled with a letter "G" indicate formation of gels. Error bars are standard deviations from two replicates.
Figure 15B:
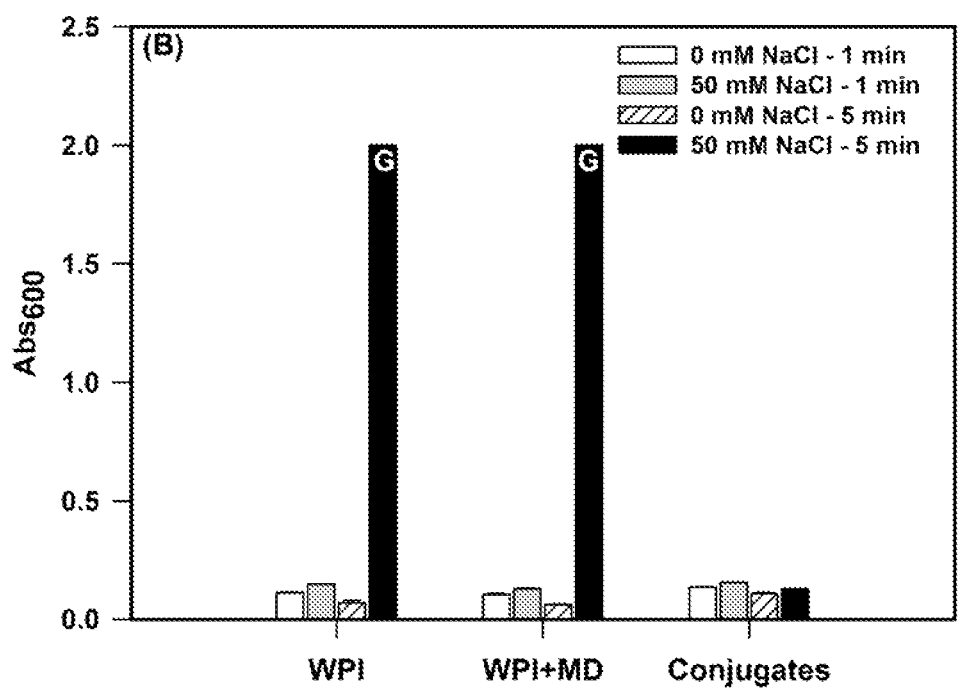
Figure 15C:
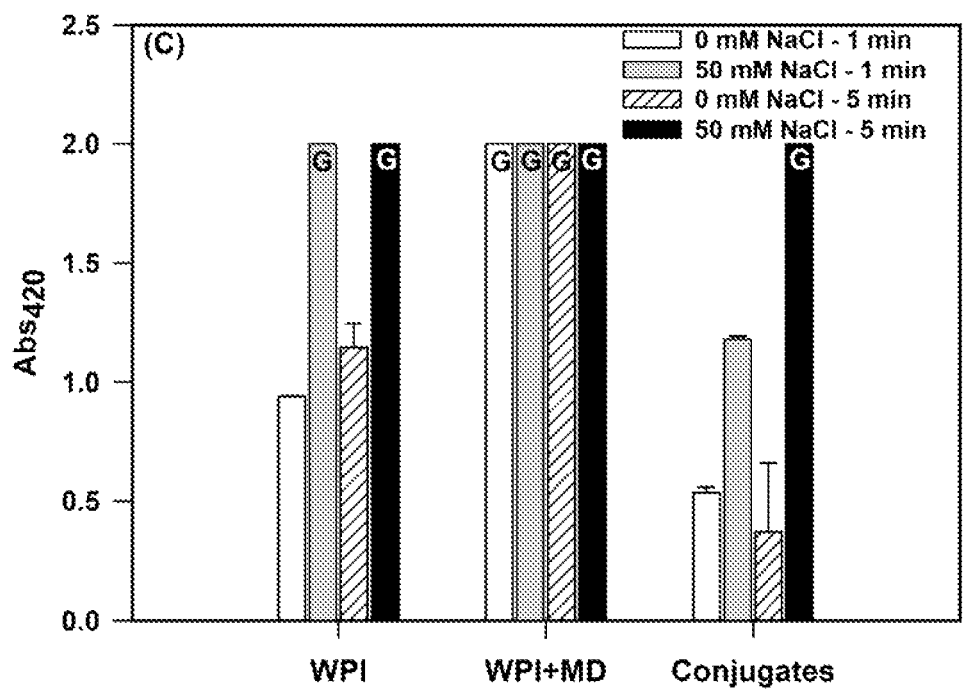
Figure 15D:
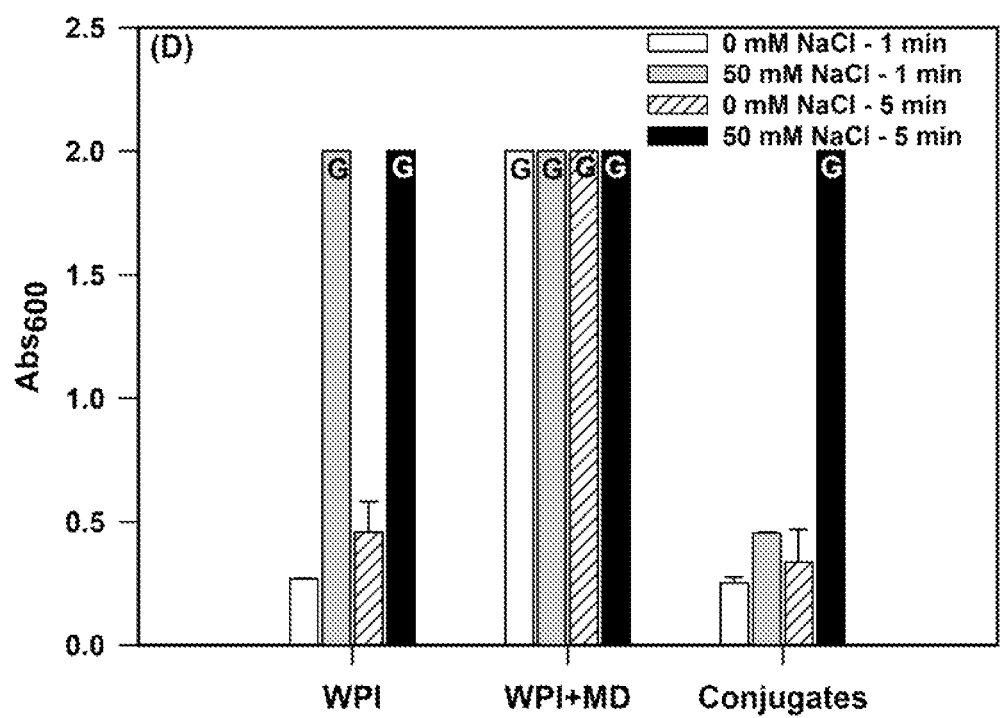
Figure 16A:
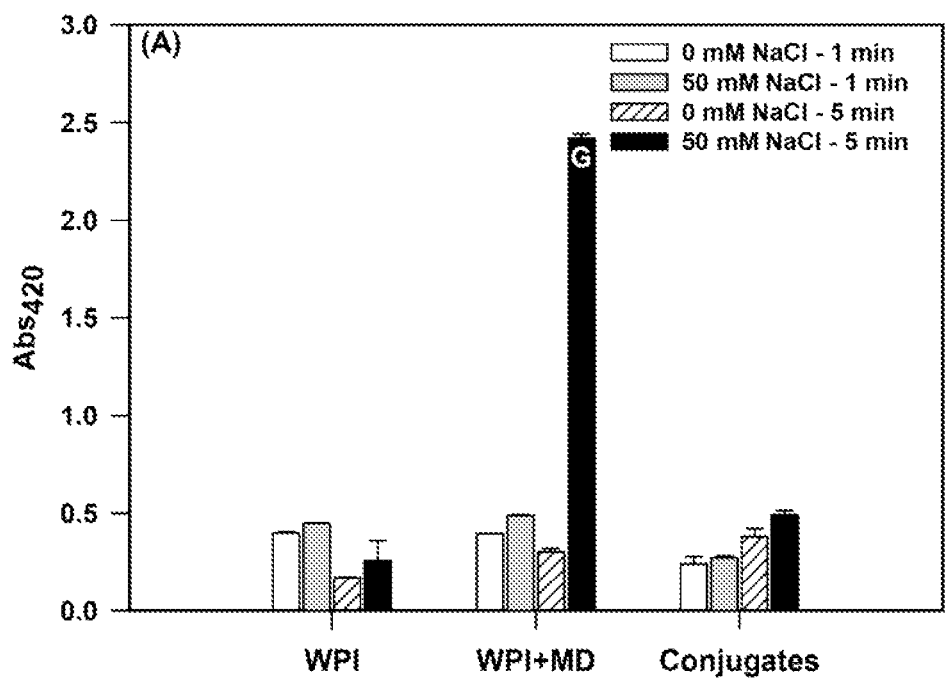
FIGS. 16A-16D. Absorbance at 420 and 600 nm for sequentially pretreated samples of 5% whey protein isolate (WPI), mixture of 5% whey protein isolate and 10% maltodextrin (WPI+MD), and 15% of whey protein-maltodextrin (1:2) conjugate samples after heating at 138° C. for 1 or 5 min.
Figure 16B:
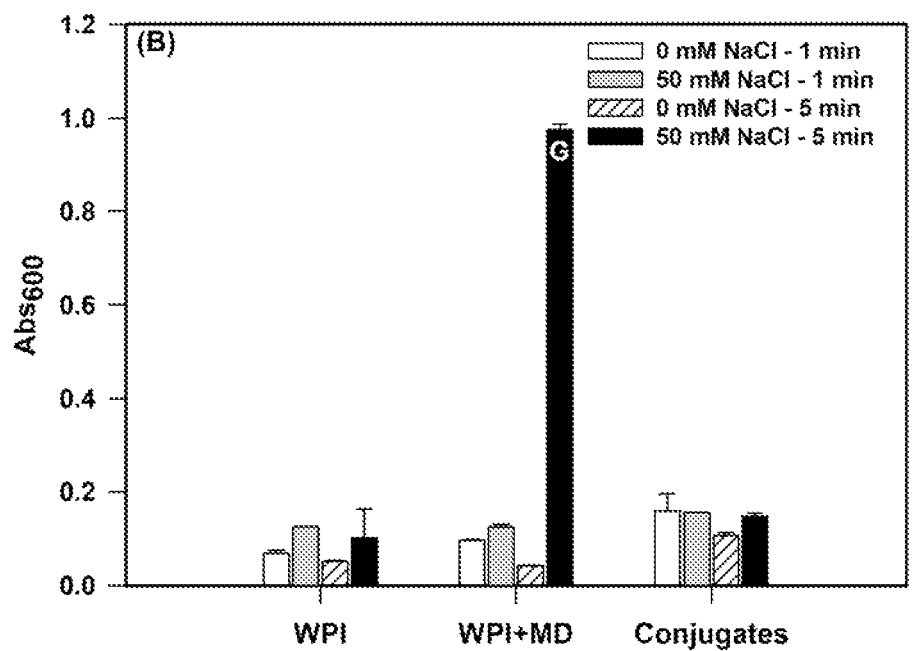
Figure 16C:
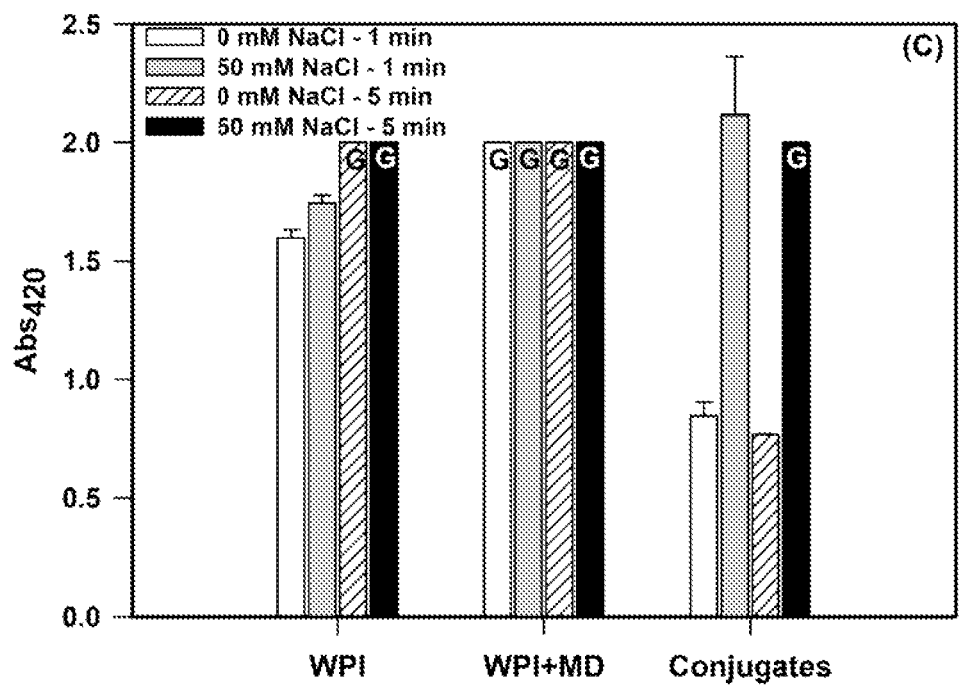
Figure 16D:
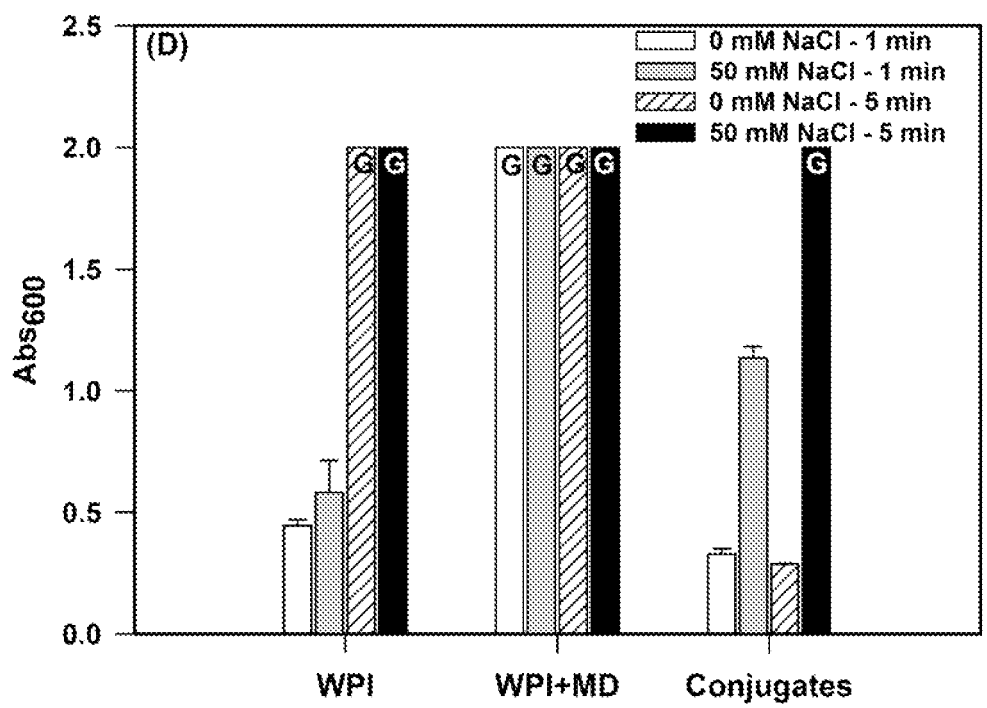

Samples in this group were first preheated at 80° C. for 15 min. The preheated sample was added with TGase equivalent to 22 or 55 U/g WPI for cross-linking at 50° C. for 4 h. After sequential pretreatments, samples from native WPI formed gels after adjusting to pH 5.0, further strengthened after heating at 80° C. for 15 min (FIGS. 6-8). At pH 3.0, pretreated conjugates had better clarity before and after heating than the other two samples that formed gels after being heated at 80° C. for 15 min (FIGS. 6-8). At pH 7.0, all pretreated samples showed good clarity after heating, and conjugates had lower absorbance at 420 nm but higher absorbance at 600 nm than the other two samples. Therefore, sequential treatments improved thermal stability of WPI and conjugates at pH 7, especially at increased salt concentrations.

Example 2

Sterilization Stability of Mixture and Conjugates of Whey Protein Isolate and Maltodextrin Pretreated by Heat and Enzyme Materials WPI sample (product 9400) was from Hilmar Cheese Company (Hilmar, Calif.). Maltodextrin M180, with a dextrose equivalence of 16.5-19.5, was a product of Grain Processing Company (Muscatine, Iowa). TGase (product Activa TG-TI) was supplied by Ajinomoto Food Ingredients LLC (Chicago, Ill.). The TGase sample had a specific activity of 1,100 U/g powder, measured based on a Sigma Method (for product T5398). One unit is defined as the formation rate of 1 μmol hydroxamate/min from substrates of N-carbobenzoxy-glutaminyl-glycine and hydroxylamine at pH 6.0 and 37° C. Other chemicals were purchased from Fisher Scientific (Pittsburgh, Pa.).

Conjugation

Conjugation by the Maillard reaction was achieved using a literature dry method (Akhtar & Dickinson, 2007) with a slight modification. Briefly, WPI and maltodextrin were dissolved at a ratio of 1:2 in deionized water to enable good mixing of the two moieties. The solution was then spray dried at an inlet temperature of 160° C. (model B-290 Mini Spray Dryer, BÜCHI Labortechnik AG, Postfach, Switzerland) to obtain a powdered product that was incubated in an oven (model 1300M, Precision Scientific, Chicago, Ill.) at 90° C. for 2 h for the Maillard reaction. The final product was stored at −20° C.

Sample Preparations

Because protein is the cause of aggregation during heating, all solutions were constituted to have 5% w/v of WPI. Specifically, three groups of solutions were prepared in a 50 mM sodium phosphate buffer: 15% w/v conjugates, 5% w/v WPI, and a mixture of 5% w/v WPI and 10% w/v maltodextrin (WPI+MD). The solutions were then treated by the following methods before heat stability tests.

Enzymatic Cross-Linking.

Cross-linking of (conjugated or non-conjugated) protein in the above solutions was performed at two TGase levels: 22 or 55 U/g WPI. The solution was adjusted to pH 7.5 and subsequently incubated in a water bath at 50° C. for 4 h.

Preheating.

To compare to enzymatic treatments, the solutions were adjusted to pH 7.5 for preheating at 80° C. for 15 min. After heating, the solution was cooled in a room-temperature water bath immediately.

Sequential Steps of Preheating and Enzymatic Cross-Linking.

In this group of treatments, the solutions were preheated as above, cooled to room temperature, and added with 22 or 55 U TGase per gram WPI. The solution was readjusted to pH 7.5 for cross-linking at 50° C. for 4 h.

Heat Stability Tests

For dairy products, sterilization is achieved at 138° C. for 8 s (McGarrahan, 1982). To test sterilization stability of samples, the above solutions at pH 7.0 and 3.0 and 0 or 50 mM NaCl were heated in a 138° C. glycerol bath for 1 or 5 min. For these tests, only 1 mL solution was used to reduce thermal come-up time. After heating, the vials were cooled in a room-temperature water bath immediately. Samples were then tested for absorbance at 420 ($Abs_{420}$) and 600 ($Abs_{600}$) nm using a UV/vis spectrophotometer (BioMate 5, Thermo Electron Corporation, Woburn, Mass.). Untreated samples were also prepared to the same WPI concentration and adjusted similarly to corresponding pH and salt conditions. Two replicates were tested for each sample. Results for this example are provided in FIGS. 9-16. As will be noted in these Figures, samples containing transglutaminase crosslinked whey protein were stable (provided clear non-turbid solutions) at pH values of 7 and 3 (protein:carbohydrate ratio of about 1:1). Conjugates also demonstrated heat stability (the ability to tolerate 138° C. for one or five minutes) at pH=7 in a solution containing 50 mM NaCl. It was also noted that at 15% (w/v) whey protein, only CPCCs demonstrated heat stability (the ability to tolerate 138° C. for one or five minutes) at a pH=3.

Improved heat stability of whey protein isolate (WPI) by enzymatic cross-linking was reported at relatively low protein concentrations (e.g., 1%) and low ionic strengths (<50 mM NaCl). This work reinvestigated effects of enzymatic cross-linking on heat stability of 5% WPI at pH 7.0, 5.0, 3.0 and 0, 50 and 100 mM NaCl. The 5% WPI in 50 mM sodium phosphate at pH 7.5, with and without preheating at 80° C. for 15 min, was treated for 1, 4, and 15 h at 50° C. by transglutaminase (TGase) at 22, 55, and 110 U/g WPI. After enzymatic treatments, the WPI solutions were adjusted to the above pH and NaCl conditions and heated at 80° C. for 15 min to evaluate heat stability. At pH 3.0, the untreated WPI had the best heat stability. At pH 5.0, all samples formed gels, regardless of NaCl concentrations and treatment levels. At pH 7.0 and 0 mM Nacl, all samples were clear after heating. At pH 7.0, the untreated WPI formed a viscous solution at 50 mM NaCl and a gel at 100 mM NaCl. For samples without preheating, heat stability of WPI at pH 7.0 was enhanced better at a longer TGase treatment and a higher level of TGase, and clear samples were observed for all samples after cross-linking for 15 h. Preheating alone significantly improved heat stability of WPI at pH 7.0, but a viscous, translucent solution was observed for the 100 mM NaCl sample. For preheated samples at pH 7.0, samples after TGase treatments were all visually clear after heating and had absorbance values below 0.4 at 600 nm.

Example 3

Heat Stable Whey Protein Isolate Pretreated by Enzymatic Cross-Linking

Materials

WPI sample (product 9400) was from Hilmar Cheese Company (Hilmar, Calif.). TGase (product Activa TG-TI) was supplied by Ajinomoto Food Ingredients LLC (Chicago, Ill.). The TGase sample had a specific activity of 1,100 U/g powder, measured based on a Sigma Method (for product T5398). One unit is defined as the formation rate of 1 μmol hydroxamate/min from substrates of N-carbobenzoxy-glutaminyl-glycine and hydroxylamine at pH 6.0 and 37° C. Other chemicals were purchased from Fisher Scientific (Pittsburgh, Pa.).

Sample Preparations

Samples were prepared with 5% w/v of WPI in a 50 mM sodium phosphate buffer and then treated by the following methods before heat stability tests.

Enzymatic Cross-Linking.

Cross-linking of (conjugated or non-conjugated) protein in the above solutions was performed at three TGase levels corresponding to 2, 5 or 10% of WPI, or 22, 55, or 110 U/g WPI. The solution was adjusted to pH 7.5 and subsequently incubated in a water bath at 50° C. for 1, 4, 8 or 15 h.

Preheating.

To compare to enzymatic treatments, the solutions were adjusted to pH 7.5 for preheating at 80° C. for 15 min. After heating, the solution was cooled in a room-temperature water bath immediately.

Sequential Steps of Preheating and Enzymatic Cross-Linking.

In this group of treatments, the solutions were preheated as above, cooled to room temperature, and added with 2, 5 or 10% of WPI, or 22, 55, or 110 U/g WPI. The solution was readjusted to pH 7.5 for cross-linking at 50° C. for 1, 4, 8 or 15 h.

Heat Stability Tests

The above treated samples, after cooling in a room-temperature water bath, were adjusted to pH 7.0, 5.0, and 3.0 using 1 N HCl and 0, 50, and 100 mM NaCl. Two mL of solution was placed in a 4 mL vial for heating in an 80° C. water bath for 15 min. After heating, the vials were cooled in a room-temperature water bath immediately. Samples were then tested for absorbance at 400 ($Abs_{400}$) and 600 ($Abs_{600}$) nm using a UV/vis spectrophotometer (BioMate 5, Thermo Electron Corporation, Woburn, Mass.). Untreated samples were also prepared to the same WPI concentration and adjusted similarly to corresponding pH and salt conditions. Two replicates were tested for each sample. Results for these tests are provided in FIGS. 17-22.

Many food systems contain both proteins and carbohydrates, and carbohydrates may improve or worsen heat stability of whey protein isolate (WPI). This work compared heat stability of 15% w/v mixtures and conjugates of WPI and maltodextrin at a 1:2 mass ratio for solutions (in 50 mM sodium phosphate) adjusted to pH 7.0, 5.0, and 3.0 and 0, 50, and 100 mM NaCl after heating at 80 C for 15 min or 138 C for 1 or 5 min. Effects of preheating (80 C for 15 min) only, transglutaminase (TGase) treatment only (22 or 55 U/g WPI at 50 C for 4 h) and sequential preheating and TGase treatments on heat stability were also evaluated. All samples at pH 5.0 formed gels after heating. All untreated samples at pH 3.0 were clear after heating at 80 C for 15 min. At pH 3.0, the untreated mixture and conjugate with 0 mM NaCl were clear after heating at 138 C for 1 or 5 min; when NaCl was 50 mM, the mixture formed gels after heating at 138 C for 1 or 5 min, while the conjugate formed a gel only after 5-min heating. At pH 7.0, the untreated mixture was only clear when there was no NaCl and heating was at 85 C for 15 min or 138 C for 1 min, while gels formed for the untreated conjugate with 100 mM NaCl after heating at 85 C for 15 min and that with 50 mM NaCl after heating at 138 C for 5 min. Better stability of conjugates than mixtures was also observed for pretreated samples, varying with pretreatment conditions. Particularly, sequentially-treated conjugates at pH 7.0 were clear at all tested salt and thermal conditions. Our novel findings suggest that sequentially-treated conjugates may provide solutions to high quality functional beverages.

Example 4

Materials

WPI sample (product 9400) was from Hilmar Cheese Company (Hilmar, Calif.). TGase (product Activa TG-TI) was supplied by Ajinomoto Food Ingredients LLC (Chicago, Ill.). The TGase sample had a specific activity of 1,100 U/g powder, measured based on a Sigma Method (for product T5398). One unit is defined as the formation rate of 1 μmol hydroxamate/min from substrates of N-carbobenzoxy-glutaminyl-glycine and hydroxylamine at pH 6.0 and 37° C. Other chemicals were purchased from Fisher Scientific (Pittsburgh, Pa.).

Sample Preparations

Samples were prepared with 5% w/v of WPI in a 50 mM sodium phosphate buffer and then treated by the following methods before heat stability tests.

Enzymatic Cross-Linking.

Cross-linking of (conjugated or non-conjugated) protein in the above solutions was performed at three TGase levels corresponding to 2, 5 or 10% mass of WPI, or 22, 55, or 110 U/g WPI. The solution was adjusted to pH 7.5 and subsequently incubated in a water bath at 50° C. for 1, 4, 8 or 15 h.

Preheating.

To compare to enzymatic treatments, the solutions were adjusted to pH 7.5 for preheating at 80° C. for 15 min. After heating, the solution was cooled in a room-temperature water bath immediately.

Sequential Steps of Preheating and Enzymatic Cross-Linking.

In this group of treatments, the solutions were preheated as above, cooled to room temperature, and added with 2, 5 or 10% of WPI, or 22, 55, or 110 U/g WPI. The solution was readjusted to pH 7.5 for cross-linking at 50° C. for 1, 4, 8 or 15 h.

Heat Stability Tests

For dairy products, sterilization is achieved at 138° C. for 8 s (McGarrahan, 1982). To test sterilization stability of samples, the above solutions at pH 7.0 and 3.0 and 0, 50, and 100 mM NaCl were heated in a 138° C. glycerol bath for 1 or 5 min. For these tests, only 1 mL solution was used to reduce thermal come-up time. After heating, the vials were cooled in a room-temperature water bath immediately. Samples were then tested for absorbance at 400 ($Abs_{420}$) and 600 ($Abs_{600}$) nm using a UV/vis spectrophotometer (BioMate 5, Thermo Electron Corporation, Woburn, Mass.). Untreated samples were also prepared to the same WPI concentration and adjusted similarly to corresponding pH and salt conditions. Two replicates were tested for each sample. The results are illustrated in FIGS. 23-26.

Shelf-stable protein beverages are highly demanded, but the information is lacking about heat stability of whey protein isolate (WPI) at commercial sterility conditions (138 C for 8 s or longer). Further, novel WPI ingredients are needed to maintain clarity after heating when the WPI content is >5%, particularly with salt. In this work, WPI (5% w/v in 50 mM sodium phosphate, pH 7.5) was cross-linked by transglutaminase (TGase) at 22 or 55 U/g WPI for 4 h at 50 C, followed by adjusting pH (to 7.0 and 3.0) and NaCl (0 or 50 mM) for heat stability tests at 138 C for 1 or 5 min. Separate WPI samples were preheated at 80 C for 15 min before cross-linking by TGase. For native WPI, clear samples were observed at pH 7.0 and 3.0 without NaCl. At pH 3.0 and 50 mM NaCl, the native WPI sample was clear after 1-min heating but formed a gel after 5-min heating. At pH 7.0 and 50 mM NaCl, the native WPI sample became very turbid and viscous after heating for 1 min and formed a gel after 5-min heating. Preheating and/or TGase treatment reduced heat stability of WPI at pH 3.0. After TGase treatment only, heat stability of WPI at pH 7.0 was not improved. Preheated WPI with 50 mM NaCl at pH 7.0 was still clear after heating for 1 min but formed a gel after 5-min heating. After preheating and cross-linking with 22 U/g WPI, heat stability of WPI was similar to preheated samples. The best heat stability of WPI at pH 7.0 was achieved for samples sequentially preheated and cross-linked with 55 U/g WPI that were all clear, even for the 50 mM NaCl sample after 5-min heating. Findings from this work are applicable to produce shelf-stable protein beverages.

Example 5

Nanodispersing Lipophilic Bioactive Compounds Using Emulsion Evaporation

The principle of emulsion-evaporation is illustrated in FIG. 27. The processes include: (1) dissolving a lipophilic compound(s) in a volatile organic solvent, (2) emulsifying the oil phase into an aqueous phase with dissolved conjugates, and (3) spray drying the emulsion. Hexane can be used as an organic solvent because it is already used in production as a processing aid, e.g., for extraction of vegetable oils from milled oilseed flours.

Production of Capsules.

Conjugates of WPI and maltodextrin with ~18 glucose units at a mass ratio of 1:2 were used to load thymol using the emulsion-evaporation processes in FIG. 27, detailed below. Formulations used to prepare emulsions are listed in Table 1.

TABLE 1

Formulations used to prepare emulsions for spray drying.

| Sample # | Thymol % in hexane (w/v) | WPI-maltodextrin % in water (w/v) | Volume % of the organic phase | Theoretical thymol loading (% w/w) |
|---|---|---|---|---|
| 1 | 0.1 | 1 | 10 | 1.1 |
| 2 | 1.25 | 1 | 10 | 12.2 |
| 3 | 1.8 | 1 | 10 | 16.7 |
| 4 | 5.0 | 1 | 10 | 35.7 |
| 5 | 10.0 | 1 | 10 | 52.6 |
| 6 | 20.0 | 1 | 10 | 69.0 |
| 7 | 20.0 | 11.1 | 10 | 16.7 |
| 8 | 30.0 | 16.7 | 10 | 16.6 |
| 9 | 40.0 | 22.2 | 10 | 16.7 |
| 10 | 50.0 | 27.8 | 10 | 16.7 |
| 11 | 20.0 | 11.1 | 15 | 24.1 |
| 12 | 20.0 | 11.1 | 20 | 31.1 |
| 13 | 20.0 | 11.1 | 25 | 37.5 |
| 14 | 20.0 | 11.1 | 30 | 43.6 |
| C-3 | 1.8 | 0.33* | 10 | 37.7 |
| C-7 | 20.0 | 3.7* | 10 | 37.5 |

*This concentration of WPI (⅓ of conjugates) was used to have the same amount of WPI as in conjugates used to prepare samples 3 and 7 because only protein is surface active.

Transparency and Heat Stability.

Spray-dried powders were hydrated at 5% w/v in deionized water for 14 h and then adjusted to pH 7.0, 5.0, or 3.0 using 1 N NaOH or HCl, with or without additional 50 mM NaCl. Samples were then tested for heat stability by heating at 85° C. for 15 min. Representative photographs are shown in FIGS. 28-30, before and after heating.

For conjugate samples 1-14, samples varied in clarity before heating, especially at pH 5.0 (FIG. 28). At pH 5.0, near isoelectric points of whey proteins that have no or minimum net charge, electrostatic repulsion between proteins is reduced and hydrophobic attraction is strengthened. The presence of thymol strengthens hydrophobic attraction among particles and this caused aggregation for Samples 4-6 and 11-14. These samples theoretically had higher loading levels and were more turbid. After heating, Samples 1-14 at pH 7.0 and 3.0 were all clear, but only Samples 3 and 7 at pH 5.0 (with 0 or 50 mM NaCl) were clear.

Samples 3 and 7 were compared with two controls (Samples C-3 and C-7), where emulsions were prepared using the same amount of WPI (⅓ of conjugate mass). Control Samples C-3 and C-7 were more turbid at pH 5.0 than Samples 3 and 7 before heating and formed gels after heating (FIG. 29). This was the first time that whey protein-containing samples at pH 5.0 did not form a gel at this protein concentration or higher in our hands.

Thymol Encapsulation Efficiency.

Using the HPLC method, the concentration of thymol in powders of Samples 3 and 7 was determined to be 1.53 and 10.57%, respectively that corresponded to an encapsulation efficiency of 9.19 and 63.32%, respectively (Table 2). For Sample 7, when powders was dispersed at 5% w/v at room temperature of 20° C., the overall thymol concentration was 0.53%, which is much higher than the solubility of 0.1% w/v for pure thymol in deionized water. This was confirmed by a sample of thymol suspended at 0.53% in deionized water that showed insoluble particulates (FIG. 31). Transparent dispersion of Sample 7 demonstrated that capsules produced by emulsion-encapsulation enabled the dispersion of thymol as transparent systems well above the solubility limit.

At the spray-drying inlet temperature used (160° C.), thymol has a vapor pressure of 11 kPa (~0.1 atmospheric pressure) that may have contributed to an encapsulation efficiency lower than 10% for Samples 3, C-3 and C-7 (Table 2). Our results also showed that appropriate emulsions enabled the encapsulation of 63.3% volatile thymol for Sample 7.

TABLE 2

Encapsulation efficiencies of Samples 3, 7, C-3 and C-7 in Table 1.

| Sample # | Thymol % in spray-dried powder* | Thymol % in non-solvent mass of formulation (Table 1) | Encapsulation efficiency %* |
|---|---|---|---|
| 3 | 1.53 ± 0.55 | 16.7 | 9.19 ± 3.31 |
| 7 | 10.6 ± 1.26 | 16.7 | 63.3 ± 7.56 |
| C-3 | 2.51 ± 0.23 | 37.7 | 6.66 ± 0.61 |
| C-7 | 3.54 ± 0.25 | 37.5 | 9.44 ± 0.67 |

*Averages from two spray-dried replicates from separate batches, determined using Equation (2) below.

Particle Size Analysis.

The SEM showed that Sample 7 formed an empty shell after spray drying (FIG. 32), possibly formed from emulsion droplets after quick evaporation of hexane. Light scattering results showed that clear samples have an mean diameter mostly smaller than 200 nm. Example size distributions of dispersions are shown in FIG. 33 for Sample 7 at pH 3.0 and 7.0 with 50 mM NaCl before and after heating at 80° C. for 15 min. The hydrodynamic radius of β-lactoglobulin, α-lactalbumin, and bovine serum albumin is 2.6-4.9 (5), 2.0 (6), and 3.7 nm (7), respectively, and is much smaller than the dimension of structures in dispersions of Sample 7. This may imply that, during the hydration process, thymol within the spray-dried powder, within the shell shown in FIG. 32, attracted nearby whey proteins together by hydrophobic interactions to form a core-shell structure illustrated in FIG. 27.

Antimicrobial Properties.

The antimicrobial function of 5% dispersions of Samples 3 and 7 against $E.\ coli$ O157:H7 is shown in FIG. 34. Sample 3 was ineffective against $E.\ coli$ strain 43894 and was effective for 3 h against $E.\ coli$ strain 43889. While Sample 7 was effective against both strains and no growth at 35° C. was observed after 48 h.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted. w/v, in the context of this invention, relates to the amount of a substance, in grams, per 100 milliliters of liquid.

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

Akhtar, M., & Dickinson, E. (2007). Whey protein-maltodextrin conjugates as emulsifying agents: An alternative to gum arabic. *Food Hydrocolloids,* 21, 607-616.

Alting A. C., Weijers M., De Hoog E. H. A., van de Pijpekamp A. M., Stuart M. A. C., Hamer R. J., De Kruif C. G. and Visschers R. W. (2004) Acid-induced cold gelation of globular proteins: Effects of protein aggregate characteristics and disulfide bonding on rheological properties. *Journal of Agricultural and Food Chemistry* 52, 623-631.

McGarrahan, E. T. (1982). Considerations necessary to provide for sterilized milk and milk products in hermetically sealed, nonrefrigetated containers. *Journal of Dairy Science,* 65, 2023-2034.

Yong, Y. H. and Foegeding, E. A. 2008. *Effects of caseins on thermal stability of bovine beta-lactoglobulin,* J Agric Food Chem 56: 10352-10358

Vardhanabhuti, B, Yucel, U., Coupland, J. N., and Foegeding, E. A. 2009. Interactions between beta-lactoglobulin and dextran sulfate at near neutral pH and their effect on thermal stability. Food Hydrocolloids. 23(6): 1511-1520.

Zhang, W. and Q. Zhong. 2010. Microemulsions as nanoreactors to produce whey protein nanoparticles with enhanced heat stability by thermal pretreatment. *Food Chemistry.* 119(4): 1318-1325.

Zhang, W. and Q. Zhong. 2009. Microemulsions as Nanoreactors to produce whey protein nanoparticles with enhanced heat stability by sequential enzymatic cross-linking and thermal pretreatments. *Journal of Agricultural and Food Chemistry.* 57(19): 9181-9189.

I claim:

1. A method of making a protein-carbohydrate conjugate (PCC) comprising:
   a) combining proteins and a carbohydrate in an aqueous solution;

b) spray drying or freeze drying said aqueous solution to form a powdered composition comprising said proteins and said carbohydrate;
c) forming a bond between said carbohydrate and said protein to form a protein-carbohydrate conjugate (PCC) by heating the powder;
d) recovering the PCC(s), and
e) loading the PCC(s) with a lipophilic substance, wherein the loading of said PCCs comprises forming an emulsion comprising PCC(s) and said lipophilic substance and spray drying the PCC(s) loaded with said lipophilic substance.

2. The method according to claim 1, wherein said protein is soy protein, whey protein, whey protein isolate, caseinate, casein and/or gelatin.

3. The method according to claim 1, wherein said carbohydrate is glyceraldehyde; arabinose; ribose; xylose; galactose, glucose, mannose; fructose; lactose; maltose; galactomannan; dextran; maltodextrin; chitosan; alginic acid; agar; carrageenan; dextran sulfate; konjac mannan; xyloglucan; starch; modified starch; pectin; polydextrose, wheat dextrin or oat bran concentrate.

4. The method according to claim 1, wherein said bond is formed via a Maillard reaction between said carbohydrate and said protein.

5. The method according to claim 1, wherein said lipophilic substance is a polyunsaturated fatty acid, steroid, microbial oil, algal oil, fungal oil, plant oil, lipophilic pharmaceutical, lipophilic nutrient, essential oil, nutraceutical, colorant or a lipophilic anti-microbial.

6. The method according to claim 1, wherein said protein is whey protein and said carbohydrate is maltodextrin.

7. A method of making a protein-carbohydrate conjugate (PCC) comprising:
a) combining proteins and a carbohydrate in an aqueous solution and said aqueous solution comprises protein in an amount of about 5% to about 20% (w/v);
b) spray drying or freeze drying said aqueous solution to form a powdered composition comprising said proteins and said carbohydrate;
c) forming a bond between said carbohydrate and said protein to form a protein-carbohydrate conjugate (PCC) by heating the powder;
d) recovering the PCC(s), and
e) loading the PCC(s) with a lipophilic substance, wherein the loading of said PCCs comprises forming an emulsion comprising PCC(s) and said lipophilic substance and spray drying the PCC(s) loaded with said lipophilic substance.

8. The method according to claim 1, wherein said powder is heated to a temperature of between 40° C. and 140° C.

9. The method according to claim 8, wherein said powder is heated to a temperature of between 70° C. and 95° C.

10. The method according to claim 7, wherein said powder is heated to a temperature of between 40° C. and 140° C.

11. The method according to claim 10, wherein said powder is heated to a temperature of between 70° C. and 95° C.

12. The method according to claim 5, wherein said lipophilic substance is a plant oil or an essential oil.

13. The method according to claim 5, wherein said lipophilic substance is a polyunsaturated fatty acid, steroid, microbial oil, algal oil, fungal oil or a lipophilic anti-microbial.

14. The method according to claim 5, wherein said lipophilic substance is a nutraceutical or colorant.

15. The method according to claim 5, wherein said lipophilic substance is a polyunsaturated fatty acid, steroid, microbial oil, algal oil or fungal oil.

16. The method according to claim 5, wherein said lipophilic substance is a lipophilic pharmaceutical or a lipophilic nutrient.

* * * * *

UNITED STATES PATENT AND TRADEMARK OFFICE
CERTIFICATE OF CORRECTION

| | |
|---|---|
| PATENT NO. | : 8,846,863 B2 |
| APPLICATION NO. | : 13/098694 |
| DATED | : September 30, 2014 |
| INVENTOR(S) | : Qixin Zhong |

It is certified that error appears in the above-identified patent and that said Letters Patent is hereby corrected as shown below:

In the Specification

Column 4,
Line 23, "letter "6" indicate" should read --letter "G" indicate--.

Column 6,
Line 42, "15 men." should read --15 min.--.

Column 16,
Lines 60-61, "pH 117.5" should read --pH 7.5--.

Signed and Sealed this
Nineteenth Day of May, 2015

Michelle K. Lee
*Director of the United States Patent and Trademark Office*